US008691782B2

(12) United States Patent
Ohgi et al.

(10) Patent No.: US 8,691,782 B2
(45) Date of Patent: *Apr. 8, 2014

(54) SINGLE-STRANDED NUCLEIC ACID MOLECULE HAVING NITROGEN-CONTAINING ALICYCLIC SKELETON

(75) Inventors: Tadaaki Ohgi, Kurume (JP); Hirotake Hayashi, Kurume (JP); Hisao Shirohzu, Kurume (JP); Tomohiro Hamasaki, Kurume (JP); Akihiro Itoh, Kurume (JP); Hiroshi Suzuki, Kurume (JP)

(73) Assignee: BONAC Corporation, Fukuoka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/254,159

(22) PCT Filed: Jul. 28, 2011

(86) PCT No.: PCT/JP2011/067292
§ 371 (c)(1),
(2), (4) Date: Aug. 31, 2011

(87) PCT Pub. No.: WO2012/017919
PCT Pub. Date: Feb. 9, 2012

(65) Prior Publication Data
US 2012/0035246 A1    Feb. 9, 2012

(30) Foreign Application Priority Data

Aug. 3, 2010  (JP) ................................ 2010-174915
Oct. 13, 2010  (JP) ................................ 2010-230806
Dec. 2, 2010  (JP) ................................ 2010-269823
Jul. 8, 2011  (JP) ................................ 2011-152381

(51) Int. Cl.
*A01N 43/04* (2006.01)
*C07H 19/044* (2006.01)
*C12Q 1/68* (2006.01)
*C12N 15/63* (2006.01)
*C07H 21/04* (2006.01)

(52) U.S. Cl.
USPC ............ 514/44; 435/6; 435/91.1; 435/91.31; 435/455; 536/23.1; 536/24.31; 536/24.5; 536/28.6

(58) Field of Classification Search
USPC ......... 435/6, 91.1, 91.31, 455, 458; 536/23.1, 536/24.5, 24.31, 28.6; 514/44
See application file for complete search history.

(56) References Cited

U.S. PATENT DOCUMENTS

| | | |
|---|---|---|
| 3,687,808 A | 8/1972 | Merigan, Jr. |
| 2002/0156261 A1 | 10/2002 | Malvy et al. |
| 2003/0059789 A1 | 3/2003 | Efimov et al. |
| 2004/0058886 A1 | 3/2004 | Scaringe |
| 2010/0137407 A1 | 6/2010 | Abe et al. |
| 2011/0052666 A1 | 3/2011 | Kaemmerer et al. |
| 2011/0055965 A1 | 3/2011 | Abe et al. |
| 2012/0135521 A1* | 5/2012 | Eshleman et al. ............ 435/375 |

FOREIGN PATENT DOCUMENTS

| | | |
|---|---|---|
| EP | 1669450 A1 | 6/2006 |
| EP | 2233573 A1 | 9/2010 |
| EP | 2562257 A1 | 2/2013 |
| JP | 2005-521393 A | 7/2005 |
| JP | 2008-278784 | 11/2008 |
| WO | 95/29241 A2 | 11/1995 |
| WO | 98/16550 A1 | 4/1998 |
| WO | 03/068798 A2 | 8/2003 |
| WO | 2003/079757 A2 | 10/2003 |
| WO | 2004/015075 | 2/2004 |
| WO | WO2004/058886 | 7/2004 |
| WO | 2004/090108 | 10/2004 |
| WO | 2005/019453 | 3/2005 |
| WO | 2006/074108 A2 | 7/2006 |
| WO | 2006/088490 A2 | 8/2006 |
| WO | 2008/116094 | 9/2008 |
| WO | 2008/140126 | 11/2008 |
| WO | WO 2009/000520 | * 12/2008 |
| WO | 2009/073809 | 6/2009 |
| WO | 2009/076321 A2 | 6/2009 |
| WO | 2009/102081 | 8/2009 |
| WO | 2011/132672 A1 | 10/2011 |

OTHER PUBLICATIONS

Hamazaki et al, Helvetica Chimica Acta, vol. 85, pp. 2183-2194 (2002).*
Nilsson et al., Science, vol. 265, pp. 2085-2088 (1994).*
Clustel et al., Nucleic Acids Res., vol. 21, No. 15, pp. 3405-3411 (1993).*
Abe et al., FEBS Letters, vol. 425, pp. 91-96 (1998).*
Supplemental structure search results accompanying WO 2009/000520.*
Confalone, et al., "Design and Synthesis of Potential DNA Cross-linking Reagents Based on the Anthramycin Class of Minor Groove Binding Compounds", J. Org. Chem., 1988, vol. 53, pp. 482-487.
Oliveira, et al., "Efficient and Expeditious Protocols for the Synthesis of Racemic and Enantiomerically Pure Endocyclic Enecarbamates from N-Acyl Lactams and N-Acyl Pyrrolidines", J. Org. Chem., 1999, vol. 64, pp. 6646-6652.

(Continued)

Primary Examiner — Jane Zara
(74) Attorney, Agent, or Firm — Morgan, Lewis & Bockius LLP

(57) ABSTRACT

Provided is a novel nucleic acid molecule that can be produced easily and efficiently and can inhibit the expression of a gene. The nucleic acid molecule is a single-stranded nucleic acid molecule including an expression inhibitory sequence that inhibits expression of a target gene. The single-stranded nucleic acid molecule includes: a region (X); a linker region (Lx); and a region (Xc). The linker region (Lx) is linked between the regions (Xc) and (Xc). The region (Xc) is complementary to the region (X). At least one of the regions (X) and (Xc) includes the expression inhibitory sequence. The linker region (Lx) has a non-nucleotide structure including at least one of a pyrrolidine skeleton and a piperidine skeleton. According to this single-stranded nucleic acid molecule, it is possible to inhibit the expression of the target gene.

37 Claims, 16 Drawing Sheets

(56) References Cited

OTHER PUBLICATIONS

Püschl, et al., "Pyrrolidine PNA: A Novel Conformationally Restricted PNA Analogue", Org. Lett., 2000, vol. 2, No. 6, pp. 4161-4163.
Fire et al., "Potent and specific genetic interference by double-stranded RNA in *Caenorhabditis elegans*", Nature, 1998, vol. 391, pp. 806-811.
Limbach et al., "Summary: the modified nucleosides of RNA", Nucleic Acids Research, 1994, vol. 22, No. 12, pp. 2183-2196.
Nykanen et al., "ATP Requirements and Small Interfering RNA Structure in the RNA Interference Pathway", Cell, 2001, vol. 107, pp. 309-321.
Teramoto et al., "Predication of siRNA functionality using generalized string kernel and support vector machine", FEBS Letters, 2005, Vol, 579, pp. 2878-2882.
Elbashir et al., "Functional anatomy of siRNAs for mediating efficient RNAi in *Drosophila melanogaster* embryo lysate", The EMBO Journal, 2001, vol. 20, No. 23, pp. 6877-6888.
Cheng et al., "TGF-B1 Gene Silencing for Treating Liver Fibrosis", Molecular Pharmaceutics, 2009, vol. 6, Iss.3, pp. 772-779.
Teramoto et al., "Prediction of siRNA functionality using generalized string kernel and support vector machine", FEBS Letters, 2005, vol. 579, pp. 2878-2882.
Cheng et al., "TGF-β1 Gene Silencing for Treating Liver Fibrosis", Molecular Pharmaceutics, 2009, vol. 6, Iss.3, pp. 772-779.
Anderson et al., "Bispecific Short Hairpin siRNA Constructs Targeted to CD4, CXCR4, and CCR5 Confer HIV-1 Resistance," Oligonucleotides, 13: 303-312 (2003).
Kumar et al, "Pyrrolidine Nucleic Acids: DNA/PNA Oligomers with 2-Hydroxy/Aminomethyl-4-(thymin-1-yl)pyrrolidine-N-acetic acid," Organic Letters, 3: 1269-1272 (2001).
Lonkar et al.. "Design and synthesis of conformationally frozen peptide nucleic acid backbone: chiral piperidine PNA as a hexitol nucleic acid surrogate," Bioorganic & Medicinal Chemistry Letters, 14: 2147-2149 (2004).
Supplementary European Search Report issued in corresponding European Application No. 11746147.5 dated Mar. 26, 2012.
Office Action issued in corresponding Europe Application No. 11746147.5 dated Apr. 20, 2012.
Office Action issued in related European Application No. 11748250.5 dated May 29, 2012.
Supplementary European Search Report issued in related European Application No. 11748250.5 dated Apr. 5, 2012.
Office Action issued in corresponding European Patent Application No. 11746147.5 dated Mar. 25, 2013.
Yu et al., "RNA interference by expression of short-interfering RNAs and hairpin RNAs in mammalian cells," Proceedings of the National Academy of Sciences, 99: 6047-6052 (2002).
Paddison et al., "Short hairpin RNAs (shRNAs) induce sequence-specific silencing in mammalian cells," Genes & Development, 16: 948-958 (2002).
McAnuff et al., "Potency of siRNA Versus shRNA Mediated Knockdown In Vivo," Journal of Pharmaceutical Sciences, 96: 2922-2930 (2007).
Search Report issued in related International Patent Application No. PCT/JP2012/080461 dated Jan. 22, 2013.
Leirdal et al., "Gene silencing in mammalian cells by preformed small RNA duplexes", Biochem. Biophys. Res. Commun., 2002, vol. 295, pp. 744-748.
Bramsen et al., "Improved silencing properties using small internally segmented interfering RNAs", Nucleic Acids Res., 2007, vol. 35, No. 17, pp. 5886-5897.
Yamaka Wa et al., "Properties and Anti-HIV Activity of Nicked Dumbbell Oligonucleotides", Nucleosides & Nucleotides, 1996, vol. 15(1-3), pp. 519-529.
Hosoya et al., "Sequence-specific inhibition of a transcription factor by circular dumbbell DNA oligonucleotides", FEBS Lett., 1999, vol. 461, pp. 136-140.
Kunugiza et al., "Inhibitory effect of ribbon-type NF-kappaB decoy oligodeoxynucleotides on osteoclast induction and activity in vitro and in vivo", Arthritis Res. Ther., 2006, vol. 8, No. 4, R103, pp. 1-10.
Abe et al., "Dumbbell-Shaped Nanocircular RNAs for RNA Interference", J. Am. Chem. Soc., 2007, vol. 129, pp. 15108-15109.
Office Action issued in related European Patent Application No. 11746147.5 dated Sep. 26, 2012.
Bosi et al., "Antimycobacterial Activity of Ionic Fullerene Derivatives," Bioorganic & Medical Chemistry Letters, 10: 1043-1045 (2000).
Partial European Search Report issued in corresponding European Patent Application No. 13167541.5 dated Jul. 31, 2013.
Extended European Search Report issued in related European Patent Application No. 13184178.5 dated Oct. 24, 2013.

* cited by examiner

| Name | Xc/Yc | Sequence | SEQ ID |
|---|---|---|---|
| NK-0036 | 25/1 | 5'- aaccaugagaaguaugacaacagcccCCACACCGGCUGUUGUCAUACUUCUCAUGGUUCUUCg -3' | SEQ ID NO: 31 |
| NK-0025 | 24/1 | 5'- accaugagaaguaugacaacagcccCCACACCGGCUGUUGUCAUACUUCUCAUGGUUCUUCGg -3' | SEQ ID NO: 32 |
| NK-0037 | 23/2 | 5'- ccaugagaaguaugacaacagcccCCACACCGGCUGUUGUCAUACUUCUCAUGGUUCUUCGga -3' | SEQ ID NO: 33 |
| NK-0016 | 22/3 | 5'- caugagaaguaugacaacagcccCCACACCGGCUGUUGUCAUACUUCUCAUGGUUCUUCGgaa -3' | SEQ ID NO: 34 |
| NK-0038 | 21/4 | 5'- augagaaguaugacaacagcccCCACACCGGCUGUUGUCAUACUUCUCAUGGUUCUUCGgaac -3' | SEQ ID NO: 35 |
| NK-0026 | 20/5 | 5'- ugagaaguaugacaacagcccCCACACCGGCUGUUGUCAUACUUCUCAUGGUUCUUCGgaacc -3' | SEQ ID NO: 36 |
| NK-0027 | 18/7 | 5'- agaaguaugacaacagcccCCACACCGGCUGUUGUCAUACUUCUCAUGGUUCUUCGgaaccau -3' | SEQ ID NO: 37 |
| NK-0028 | 16/9 | 5'- aaguaugacaacagcccCCACACCGGCUGUUGUCAUACUUCUCAUGGUUCUUCGgaaccauga -3' | SEQ ID NO: 38 |
| NK-0029 | 14/11 | 5'- guaugacaacagcccCCACACCGGCUGUUGUCAUACUUCUCAUGGUUCUUCGgaaccaugaga -3' | SEQ ID NO: 39 |
| NK-0014 | 12/13 | 5'- augacaacagcccCCACACCGGCUGUUGUCAUACUUCUCAUGGUUCUUCGgaaccaugagaag -3' | SEQ ID NO: 40 |
| NK-0030 | 9/16 | 5'- acaacagcccCCACACCGGCUGUUGUCAUACUUCUCAUGGUUCUUCGgaaccaugagaaguau -3' | SEQ ID NO: 41 |
| NK-0031 | 7/18 | 5'- aacagcccCCACACCGGCUGUUGUCAUACUUCUCAUGGUUCUUCGgaaccaugagaaguauga -3' | SEQ ID NO: 42 |
| NK-0020 | 5/20 | 5'- cagcccCCACACCGGCUGUUGUCAUACUUCUCAUGGUUCUUCGgaaccaugagaaguaugaca -3' | SEQ ID NO: 43 |
| NK-0019 | 4/21 | 5'- agcccCCACACCGGCUGUUGUCAUACUUCUCAUGGUUCUUCGgaaccaugagaaguaugacaa -3' | SEQ ID NO: 44 |
| NK-0018 | 3/22 | 5'- gcccCCACACCGGCUGUUGUCAUACUUCUCAUGGUUCUUCGgaaccaugagaaguaugacaac -3' | SEQ ID NO: 45 |
| NK-0039 | 2/23 | 5'- cccCCACACCGGCUGUUGUCAUACUUCUCAUGGUUCUUCGgaaccaugagaaguaugacaaca -3' | SEQ ID NO: 46 |
| NK-0032 | 1/24 | 5'- ccCCACACCGGCUGUUGUCAUACUUCUCAUGGUUCUUCGgaaccaugagaaguaugacaacag -3' | SEQ ID NO: 47 |
| NK-0040 | 1/25 | 5'- cCCACACCGGCUGUUGUCAUACUUCUCAUGGUUCUUCGgaaccaugagaaguaugacaacagc -3' | SEQ ID NO: 48 |

NK-0047  26/27  5'- aaccaugagaaguaugacaacagccCCACACCGGCUGUUGUCAUACUUCUCAUGGUUCGUUCGc -3'   SEQ ID NO: 61
                                                                              *
NK-0025  25/26  5'- accaugagaaguaugacaacagccCCACACCGGCUGUUGUCAUACUUCUCAUGGUUCGUUCGg -3'    SEQ ID NO: 62
                                                                             *
NK-0048  24/25  5'- accaugagaaguaugacaacagcCCACACCGCUGUUGUCAUACUUCUCAUGGUUCGUUCGg -3'     SEQ ID NO: 63
                                                                           *
NK-0049  23/24  5'- ccaugagaaguaugacaacagcCCACACCGCUGUUGUCAUACUUCUCAUGGUUUUCGa -3'        SEQ ID NO: 64
                                                                         *
NK-0050  23/24  5'- accaugagaaguaugacaacagCCACACCGCUGUUGUCAUACUUCUCAUGGUUCUUCGg -3'       SEQ ID NO: 65

NK-0051  22/23  5'- ccaugagaaguaugacaacagCCACACCCUGUUGUCAUACUUCUCAUGGUUUUCGg -3'          SEQ ID NO: 66
                                                                      *
NK-0052  21/22  5'- caugagaaguaugacaacacCCACACCCUGUUGUCAUACUUCUCAUGGUUUUCGa -3'           SEQ ID NO: 67
                                                                     *
NK-0053  21/22  5'- caugagaaguaugacaacaCCACACCCUGUUGUCAUACUUCUCAUGGUUUUCGa -3'            SEQ ID NO: 68

NK-0054  20/21  5'- caugagaaguaugacaacaCCACACCGUUGUCAUACUUCUCAUGGUUUUCGa -3'              SEQ ID NO: 69
```

FIG. 22

SINGLE-STRANDED NUCLEIC ACID MOLECULE HAVING NITROGEN-CONTAINING ALICYCLIC SKELETON

TECHNICAL FIELD

The present invention relates to a single-stranded nucleic acid molecule that inhibits gene expression. In particular, the present invention relates to a single-stranded nucleic acid molecule having a nitrogen-containing alicyclic skeleton, a composition containing the single-stranded nucleic acid molecule, and the use of the single-stranded nucleic acid molecule.

BACKGROUND ART

As a technique for inhibiting gene expression, RNA interference (RNAi) is known, for example (Non-Patent Document 1). Inhibition of gene expression by RNA interference generally is carried out by administering a short double-stranded RNA molecule to a cell or the like, for example. The double-stranded RNA molecule generally is called siRNA (small interfering RNA). It has been reported that not only siRNA but also a circular RNA molecule that is rendered partially double-stranded by intermolecular annealing also can inhibit gene expression (Patent Document 1). However, the RNA molecules used in these techniques to induce the inhibition of the gene expression have the following problems.

First, in order to produce the siRNA, it is necessary to synthesize a sense strand and an antisense strand separately and to hybridize these strands at the end of the process. Thus, there is a problem of low manufacturing efficiency. Furthermore, when the siRNA is administered to a cell, it is necessary to administer the siRNA to the cell while inhibiting the dissociation to single-stranded RNAs, which requires a laborious task of setting the conditions for handling the siRNA. On the other hand, the circular RNA molecule has a problem in that its synthesis is difficult.

These RNA molecules basically are composed of nucleotide residues. At present, in order to impart some function to the RNA molecules or to label the RNA molecules, there is no other way but to modify any of the components, i.e., a base, a sugar residue, or a phosphate group, of the nucleotide residue(s). Therefore, in the development of pharmaceuticals and the like utilizing RNA interference, it is very difficult to alter the RNA molecules so as to impart a further function thereto or to label them while maintaining their function of inhibiting the gene expression.

CITATION LIST

Non-Patent Document(s)

Non-Patent Document 1: Fire. et al., Nature, Feb. 19, 1998; 391 (6669): pp. 806-811

Patent Document(s)

Patent Document 1: U.S. Patent Publication No. 2004-058886

BRIEF SUMMARY OF THE INVENTION

With the foregoing in mind, it is an object of the present invention to provide a novel nucleic acid molecule that can be produced easily and efficiently and can inhibit gene expression.

In order to achieve the above object, the present invention provides a single-stranded nucleic acid molecule including: an expression inhibitory sequence that inhibits expression of a target gene. The single-stranded nucleic acid molecule includes: a region (X); a linker region (Lx); and a region (Xc). The linker region (Lx) is linked between the regions (Xc) and (Xc). At least one of the regions (X) and (Xc) includes the expression inhibitory sequence. The linker region (Lx) has a non-nucleotide structure including at least one of a pyrrolidine skeleton and a piperidine skeleton.

The present invention also provides a composition for inhibiting the expression of a target gene. The composition contains the single-stranded nucleic acid molecule according to the present invention.

The present invention also provides a pharmaceutical composition containing the single-stranded nucleic acid molecule according to the present invention.

The present invention also provides a method for inhibiting the expression of a target gene. In this method, the single-stranded nucleic acid molecule according to the present invention is used.

The present invention also provides a method for treating a disease, including the step of administering the single-stranded nucleic acid molecule according to the present invention to a patient. The single-stranded nucleic acid molecule includes, as the expression inhibitory sequence, a sequence that inhibits expression of a gene causing the disease.

According to the single-stranded nucleic acid molecule of the present invention, it is possible to inhibit the expression of a gene. Furthermore, since the single-stranded nucleic acid molecule is not circular, it can be synthesized easily. Also, since it is a single strand, an annealing step required in the production of a double strand is not necessary, so that it can be produced efficiently. Moreover, since the linker region includes the non-nucleotide residue(s), not only conventional alterations to nucleotide residues, for example, but also alterations such as modification in the linker region become possible, for example.

It is the inventors of the present invention who first discovered that the gene expression can be inhibited according to the structure of the single-stranded nucleic acid molecule of the present invention. It is speculated that the gene inhibitory effect of the single-stranded nucleic acid molecule of the present invention is caused by a phenomenon similar to RNA interference. It is to be noted, however, that the inhibition of the gene expression in the present invention is not limited or restricted by RNA interference.

BRIEF DESCRIPTION OF DRAWINGS

FIG. 17 shows ssRNAs used in a reference example.

FIG. 22 shows ssRNAs used in still another reference example.

MODE FOR CARRYING OUT THE INVENTION

Figure 1A:
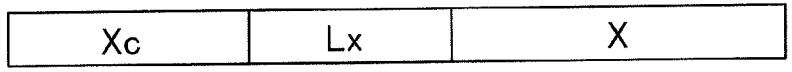
FIG. 1 shows schematic views illustrating an example of the single-stranded nucleic acid molecule of the present invention.

Terms used in the present specification each have a meaning generally used in the art, unless otherwise stated.

1. ssPN Molecule

The single-stranded nucleic acid molecule of the present invention is, as described above, a single-stranded nucleic acid molecule including: an expression inhibitory sequence that inhibits expression of a target gene. The single-stranded nucleic acid molecule includes: a region (X); a linker region (Lx); and a region (Xc). The linker region (Lx) is linked between the regions (Xc) and (Xc). At least one of the regions (X) and (Xc) includes the expression inhibitory sequence. The linker region (Lx) has a non-nucleotide structure including at least one of a pyrrolidine skeleton and a piperidine skeleton.

In the present invention, "inhibition of expression of a target gene" means disrupting the expression of the target gene, for example. The mechanism by which the inhibition is achieved is not particularly limited, and may be downregulation or silencing, for example. The inhibition of the expression of the target gene can be verified by: a decrease in the amount of a transcription product derived from the target gene; a decrease in the activity of the transcription product; a decrease in the amount of a translation product generated from the target gene; a decrease in the activity of the translation product; or the like, for example. The proteins may be mature proteins, precursor proteins before being subjected to processing or post-translational modification, or the like, for example.

The single-stranded nucleic acid molecule of the present invention hereinafter may also be referred to as the "ssPN molecule" of the present invention. The ssPN molecule of the present invention can be used to inhibit the expression of a target gene in vivo or in vitro, for example, so that it also can be referred to as an "ssPN molecule for inhibiting the expression of a target gene" or "inhibitor of the expression of a target gene". Furthermore, the ssPN molecule of the present invention can inhibit the expression of a target gene by, for example, RNA interference, so that it also can be referred to as an "ssPN molecule for RNA interference", "ssPN molecule for inducing RNA interference", or "RNA interference agent or RNA interference-inducting agent". Furthermore, according to the present invention, it is possible to inhibit a side effect such as interferon induction, for example.

In the ssPN molecule of the present invention, the 5' end and the 3' end are not linked to each other. Thus, the ssPN molecule of the present invention also can be referred to as a "linear single-stranded nucleic acid molecule".

In the ssPN molecule of the present invention, the expression inhibitory sequence is a sequence that exhibits an activity of inhibiting the expression of a target gene when the ssPN molecule of the present invention is introduced into a cell in vivo or in vitro, for example. The expression inhibitory sequence is not particularly limited, and can be set as appropriate depending on the kind of a target gene whose expression is to be inhibited. As the expression inhibitory sequence, a sequence involved in RNA interference caused by siRNA can be used as appropriate, for example. Generally, RNA interference is a phenomenon in which a long double-stranded RNA (dsRNA) is cleaved in a cell by Dicer to produce a double-stranded RNA (siRNA: small interfering RNA) composed of about 19 to 21 base pairs and having a protruding 3' end, and one of the single-stranded RNAs composing the siRNA binds to a target mRNA to degrade the mRNA, whereby the translation of the mRNA is inhibited. As the sequence of the single-stranded RNA of the siRNA binding to the target mRNA, various kinds of sequences for various kinds of target genes have been reported, for example. In the present invention, for example, the sequence of the single-stranded RNA of the siRNA can be used as the expression inhibitory sequence.

It should be noted that the point of the present invention is not the sequence information of the expression inhibitory sequence for the target gene. Actually, the present invention relates to the structure of a nucleic acid molecule for allowing a target gene inhibitory activity brought about by the expression inhibitory sequence to function in a cell, for example. Therefore, in the present invention, not only the sequences of the single-stranded RNA of the siRNA known at the time of the filing of the present application but also sequences that would be identified in the future can be used as the expression inhibitory sequence, for example.

The expression inhibitory sequence preferably is at least 90% complementary, more preferably 95% complementary, still more preferably 98% complementary, and particularly preferably 100% complementary to a predetermined region of the target gene, for example. When the expression inhibitory sequence satisfies the above-described complementarity, an off-target effect can be reduced sufficiently, for example.

Specific examples of the expression inhibitory sequence are as follows: when the target gene is the GAPDH gene, a 19-mer sequence shown in SEQ ID NO: 4 can be used, for example; when the target gene is the TGF-β1 gene, a 21-mer sequence shown in SEQ ID NO: 18 can be used, for example; when the target gene is the LAMA1 gene, a 19-mer sequence shown in SEQ ID NO: 6 can be used, for example; and when the target gene is the LMNA gene, a 19-mer sequence shown in SEQ ID NO: 30 can be used, for example.

```
                                              (SEQ ID NO: 4)
5'-GUUGUCAUACUUCUCAUGG-3'

(SEQ ID NO: 18)
5'-AAAGUCAAUGUACAGCUGCUU-3'

(SEQ ID NO: 6)
5'-AUUGUAACGAGACAAACAC-3'

(SEQ ID NO: 30)
5'-UUGCGCUUUUUGGUGACGC-3'
```

It is speculated that the inhibition of the expression of a target gene by the ssPN molecule of the present invention is achieved by RNA interference. It should be noted, however, that the present invention is by no means limited by this mechanism. Unlike the so-called siRNA, the ssPN molecule of the present invention is not introduced to a cell or the like in the form of dsRNA composed of two single-stranded RNAs, and it is not always necessary to cleave out the expression inhibitory sequence in the cell, for example. Thus, it can be said that the ssPN molecule of the present invention exhibits an RNA interference-like function, for example.

In the ssPN molecule of the present invention, the linker region (Lx) may have: a non-nucleotide structure containing the pyrrolidine skeleton; a non-nucleotide structure containing the piperidine skeleton; and both a non-nucleotide structure containing the pyrrolidine skeleton and a non-nucleotide structure containing the piperidine skeleton, for example. The ssPN molecule of the present invention can inhibit a side effect such as interferon induction in vivo and exhibits excellent nuclease resistance, for example.

In the ssPN molecule of the present invention, the pyrrolidine skeleton may be the skeleton of a pyrrolidine derivative obtained through substitution of at least one carbon constituting the 5-membered ring of pyrrolidine, for example. In the case of substitution, it is preferable to substitute the carbon(s) other than C-2, for example. The carbon may be substituted with nitrogen, oxygen, or sulfur, for example. The pyrrolidine skeleton may contain, for example, a carbon-carbon double bond or a carbon-nitrogen double bond in, for example, the 5-membered ring of pyrrolidine. In the pyrrolidine skeleton, carbons and nitrogen constituting the 5-membered ring of pyrrolidine each may have hydrogen bound thereto, or a substituent to be described below bound thereto, for example. The linker region (Lx) may be linked to the regions (X) and (Xc) via, for example, any group in the pyrrolidine skeleton, preferably any one carbon atom or nitrogen in the 5-membered ring, and more preferably the 2-position carbon (C-2) or nitrogen in the 5-membered ring. Examples of the pyrrolidine skeleton include proline skeletons and prolinol skeletons. The proline skeletons, the prolinol skeletons, and the like are excellent in safety because they are substances present in living organisms and reductants thereof, for example.

In the ssPN molecule of the present invention, the piperidine skeleton may be the skeleton of a piperidine derivative obtained through substitution of at least one carbon constituting the 6-membered ring of piperidine, for example. In the case of substitution, it is preferable to substitute the carbon(s) other than C-2, for example. The carbon may be substituted with nitrogen, oxygen, or sulfur, for example. The piperidine skeleton may contain, for example, a carbon-carbon double bond or a carbon-nitrogen double bond in, for example, the 6-membered ring of piperidine. In the piperidine skeleton, carbons and nitrogen constituting the 6-membered ring of piperidine each may have hydrogen bound thereto, or a substituent to be described below bound thereto, for example. The linker region (Lx) may be linked to the regions (X) and (Xc) via, for example, any group in the piperidine skeleton, preferably any one carbon atom or nitrogen in the 6-membered ring, and more preferably the 2-position carbon (C-2) or nitrogen in the 6-membered ring.

The linker region may be composed of the non-nucleotide residue(s) having the non-nucleotide structure only, or may contain the non-nucleotide residue(s) having the non-nucleotide structure and the nucleotide residue(s), for example.

In the ssPN molecule of the present invention, the linker region is represented by the following formula (I), for example.

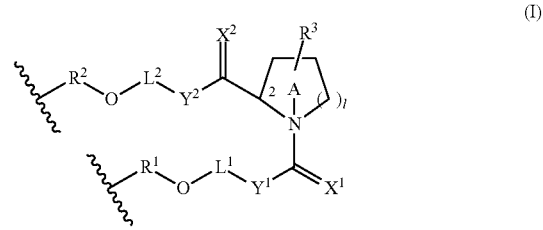

In the formula (I), for example, $X^1$ and $X^2$ are each independently $H_2$, O, S, or NH;

$Y^1$ and $Y^2$ are each independently a single bond, $CH_2$, NH, O, or S;

$R^3$ is a hydrogen atom or substituent that is bound to C-3, C-4, C-5, or C-6 on a ring A;

$L^1$ is an alkylene chain composed of n atoms, and a hydrogen atom(s) on an alkylene carbon atom(s) may or may not be substituted with OH, $OR^a$, $NH_2$, $NHR^a$, $NR^aR^b$, SH, or $SR^a$, or, $L^1$ is a polyether chain obtained by substituting at least one carbon atom on the alkylene chain with an oxygen atom, provided that: when $Y^1$ is NH, O, or S, an atom bound to $Y^1$ in $L^1$ is carbon, an atom bound to $OR^1$ in $L^1$ is carbon, and oxygen atoms are not adjacent to each other;

$L^2$ is an alkylene chain composed of m atoms, and a hydrogen atom(s) on an alkylene carbon atom(s) may or may not be substituted with OH, $OR^c$, $NH_2$, $NHR^c$, $NR^cR^d$, SH, or $SR^c$, or $L^2$ is a polyether chain obtained by substituting at least one carbon atom on the alkylene chain with an oxygen atom, provided that: when $Y^2$ is NH, O, or S, an atom bound to $Y^2$ in $L^2$ is carbon, an atom bound to $OR^2$ in $L^2$ is carbon, and oxygen atoms are not adjacent to each other;

$R^a$, $R^b$, $R^c$, and $R^d$ are each independently a substituent or a protecting group;

l is 1 or 2;

m is an integer in the range from 0 to 30;

n is an integer in the range from 0 to 30;

on the ring A, one carbon atom other than C-2 may be substituted with nitrogen, oxygen, or sulfur;

the ring A may contain a carbon-carbon double bond or a carbon-nitrogen double bond;

the regions (Xc) and (X) are each linked to the linker region (Lx) via —OR$^1$— or —OR$^2$—; and R$^1$ and R$^2$ may or may not be present, and when they are present, R$^1$ and R$^2$ are each independently a nucleotide residue or the structure of the formula (I).

In the formula (I), X$^1$ and X$^2$ are each independently H$_2$, O, S, or NH, for example. In the formula (I), "X$^1$ is H$_2$" means that X$^1$ forms CH$_2$ (a methylene group) together with a carbon atom to which X$^1$ binds. The same applies to X$^2$.

In the formula (I), Y$^1$ and Y$^2$ are each independently a single bond, CH$_2$, NH, O, or S.

In the formula (I), l in the ring A is 1 or 2. When l=1, the ring A is a 5-membered ring, which is, for example, the pyrrolidine skeleton. The pyrrolidine skeleton is, for example, a proline skeleton, a prolinol skeleton, or the like, and specific examples include divalent structures of the proline skeleton and the prolinol skeleton. When l=2, the ring A is a 6-membered ring, which is, for example, the piperidine skeleton. On the ring A, one carbon atom other than C-2 may be substituted with nitrogen, oxygen, or sulfur. Furthermore, the ring A may contain a carbon-carbon double bond or a carbon-nitrogen double bond. The ring A may be in either L-form or D-form, for example.

In the formula (I), R$^3$ is a hydrogen atom or substituent that is bound to C-3, C-4, C-5, or C-6 on the ring A. When R$^3$ is the substituent, there may be one substituent R$^3$, two or more substituents R$^3$, or no substituent R$^3$, and when there are a plurality of substituents R$^3$, they may be the same or different.

The substituent R$^3$ is, for example, a halogen, OH, OR$^4$, NH$_2$, NHR$^4$, NR$^4$R$^5$, SH, SR$^4$, an oxo group (=O), or the like.

R$^4$ and R$^5$ are each a substituent or a protecting group, and they may be the same or different. Examples of the substituent include halogens, alkyls, alkenyls, alkynyls, haloalkyls, aryls, heteroaryls, arylalkyls, cycloalkyls, cycloalkenyls, cycloalkylalkyls, cyclylalkyls, hydroxyalkyls, alkoxyalkyls, aminoalkyls, heterocyclylalkenyls, heterocyclylalkyls, heteroarylalkyls, silyls, and silyloxyalkyls. The same applies hereinafter. The substituent R$^3$ may be any of the above-listed substituents.

The protecting group is a functional group that inactivates a highly-reactive functional group, for example. Examples of the protecting group include known protecting groups. Regarding the protecting group, the description in the literature (J. F. W. McOmie, "Protecting Groups in Organic Chemistry", Plenum Press, London and New York, 1973) is incorporated herein by reference, for example. The protecting group is not particularly limited, and examples thereof include a tert-butyldimethylsilyl group (TBDMS), a bis(2-acetoxyethyloxy)methyl group (ACE), a triisopropylsilyloxymethyl group (TOM), a 1-(2-cyanoethoxy)ethyl group (CEE), a 2-cyanoethoxymethyl group (CEM), a tolylsulfonylethoxymethyl group (TEM), and a dimethoxytrityl group (DMTr). When R$^3$ is OR$^4$, the protecting group is not particularly limited, and examples thereof include a TBDMS group, an ACE group, a TOM group, a CEE group, a CEM group, and a TEM group. Other examples of the protecting group include silyl-containing groups represented by the formula to be shown in the paragraph [0275]. The same applies hereinafter.

In the formula (I), L$^1$ is an alkylene chain composed of n atoms. A hydrogen atom(s) on an alkylene carbon atom(s) may or may not be substituted with OH, OR$^a$, NH$_2$, NHR$^a$, NR$^a$R$^b$, SH, or SR$^a$, for example. Alternatively, L$^1$ may be a polyether chain obtained by substituting at least one carbon atom on the alkylene chain with an oxygen atom. The polyether chain is, for example, polyethylene glycol. When Y$^1$ is NH, O, or S, an atom bound to Y$^1$ in L$^1$ is carbon, an atom bound to OR$^1$ in L$^1$ is carbon, and oxygen atoms are not adjacent to each other. That is, for example, when Y$^1$ is O, this oxygen atom and the oxygen atom in L$^1$ are not adjacent to each other, and the oxygen atom in OR$^1$ and the oxygen atom in L$^1$ are not adjacent to each other.

In the formula (I), L$^2$ is an alkylene chain composed of m atoms. A hydrogen atom(s) on an alkylene carbon atom(s) may or may not be substituted with OH, OR$^c$, NH$_2$, NHR$^c$, NR$^c$R$^d$, SH, or SR$^c$, for example. Alternatively, L$^2$ may be a polyether chain obtained by substituting at least one carbon atom on the alkylene chain with an oxygen atom. When Y$^2$ is NH, O, or S, an atom bound to Y$^2$ in L$^2$ is carbon, an atom bound to OR$^2$ in L$^2$ is carbon, and oxygen atoms are not adjacent to each other. That is, for example, when Y$^2$ is O, this oxygen atom and the oxygen atom in L$^2$ are not adjacent to each other, and the oxygen atom in OR$^2$ and the oxygen atom in L$^2$ are not adjacent to each other.

n of L$^1$ and m of L$^2$ are not particularly limited, and the lower limit of each of them may be 0, for example, and the upper limit of the same is not particularly limited. n and m can be set as appropriate depending on a desired length of the linker region (Lx), for example. For example, from the view point of manufacturing cost, yield, and the like, n and m are each preferably 0 to 30, more preferably 0 to 20, and still more preferably 0 to 15. n and m may be the same (n=m) or different. n+m is, for example, 0 to 30, preferably 0 to 20, and more preferably 0 to 15.

R$^a$, R$^b$, R$^c$, and R$^d$ is, for example, each independently a substituent or a protecting group. The substituent and the protecting group are the same as described above, for example.

In the formula (I), hydrogen atoms each independently may be substituted with a halogen such as Cl, Br, F, or I, for example.

The regions (Xc) and (X) are each linked to the linker region (Lx) via —OR$^1$— or —OR$^2$—, for example. R$^1$ and R$^2$ may or may not be present. When R$^1$ and R$^2$ are present, R$^1$ and R$^2$ are each independently a nucleotide residue or the structure represented by the formula (I). When R$^1$ and/or R$^2$ is the nucleotide residue, the linker region (Lx) is composed of the non-nucleotide residue having the structure of the formula (I) excluding the nucleotide residue R$^1$ and/or R$^2$, and the nucleotide residue(s), for example. When R$^1$ and/or R$^2$ is the structure represented by the formula (I), the structure of the linker region (Lx) is such that, for example, two or more of the non-nucleotide residues having the structure of the formula (I) are linked to each other. The number of the structures of the formula (I) may be 1, 2, 3, or 4, for example. When the linker region (Lx) includes a plurality of the structures, the structures of the formula (I) may be linked either directly or via the nucleotide residue(s), for example. On the other hand, when R$^1$ and R$^2$ are not present, the linker region (Lx) is composed of the non-nucleotide residue having the structure of the formula (I) only, for example.

The combination of the regions (Xc) and (X) with —OR$^1$— and —OR$^2$— is not particularly limited, and may be either of the following conditions, for example.

Condition (1):
the regions (Xc) and (X) are linked to the structure of the formula (I) via —OR$^2$— and —OR$^1$—, respectively.

Condition (2):
the regions (Xc) and (X) are linked to the structure of the formula (I) via —OR$^1$— and —OR$^2$—, respectively.

Examples of the structure of the formula (I) include the structures of the following formulae (I-1) to (I-9). In the following formulae, n and m are the same as in the formula (I). In the following formulae, q is an integer from 0 to 10.

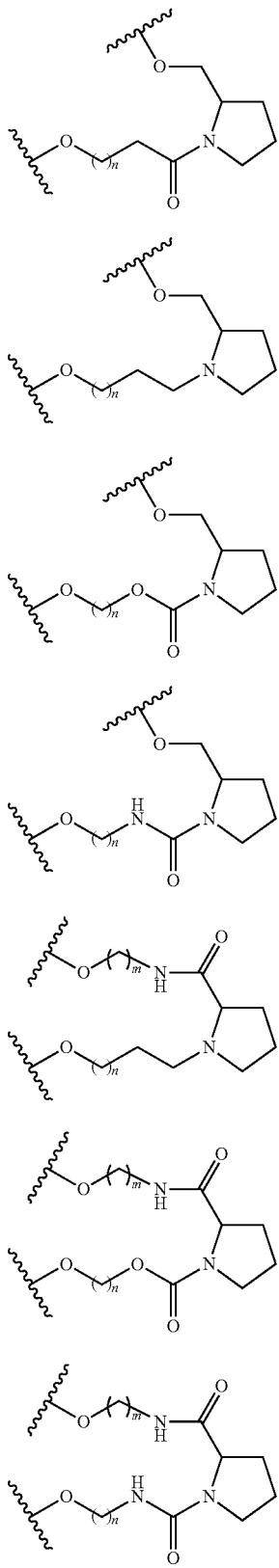

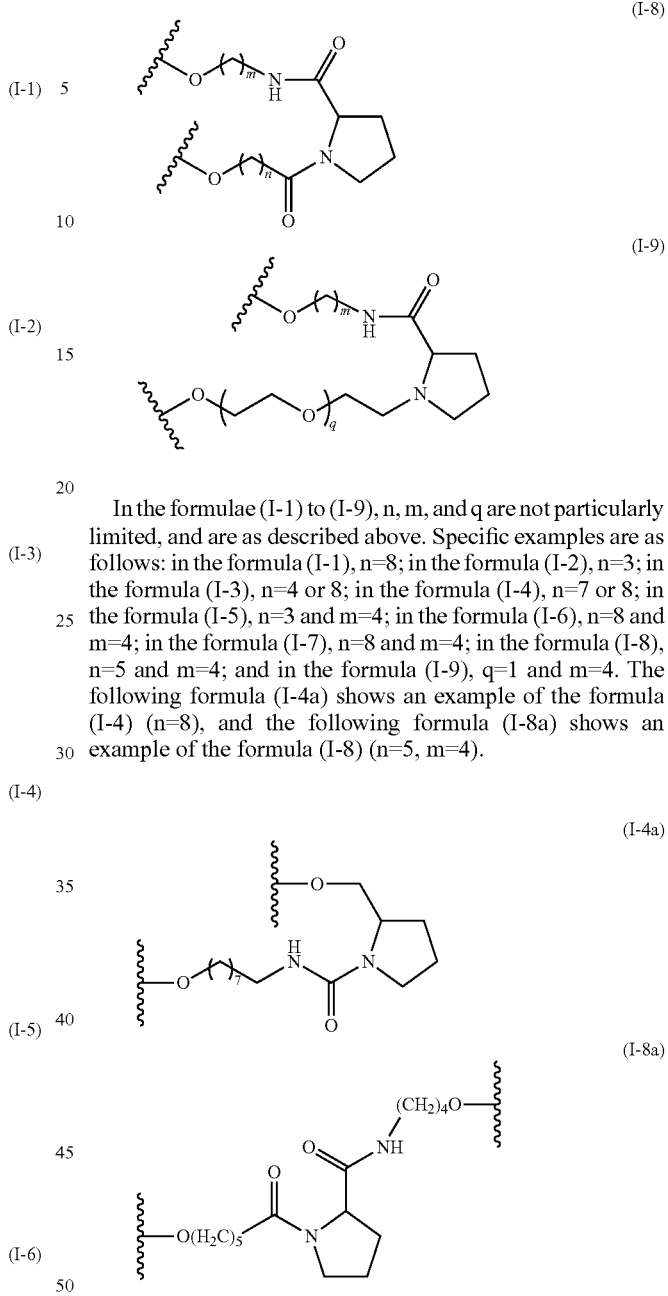

In the formulae (I-1) to (I-9), n, m, and q are not particularly limited, and are as described above. Specific examples are as follows: in the formula (I-1), n=8; in the formula (I-2), n=3; in the formula (I-3), n=4 or 8; in the formula (I-4), n=7 or 8; in the formula (I-5), n=3 and m=4; in the formula (I-6), n=8 and m=4; in the formula (I-7), n=8 and m=4; in the formula (I-8), n=5 and m=4; and in the formula (I-9), q=1 and m=4. The following formula (I-4a) shows an example of the formula (I-4) (n=8), and the following formula (I-8a) shows an example of the formula (I-8) (n=5, m=4).

In the ssPN molecule of the present invention, the region (Xc) is complementary to the region (X). Thus, in the ssPN molecule of the present invention, a double strand can be formed by fold-back of the region (Xc) toward the region (X) and self-annealing of the regions (Xc) and (X). The ssPN molecule of the present invention can form a double strand intramolecularly as described above. Thus, the structure of the ssPN molecule is totally different from the structre of a double-stranded RNA obtained through annealing of two separate single-stranded RNAs, such as siRNA conventionally used in RNA interference, for example.

In the ssPN molecule of the present invention, for example, only the region (Xc) may fold back to form a double strand with the region (X), or another double strand may be formed in another region. Hereinafter, the former ssPN molecule, i.e., the ssPN molecule in which double strand formation occurs at one location is referred to as a "first ssPN molecule", and the latter ssPN molecule, i.e., the ssPN molecule in which double strand formation occurs at two locations is referred to as a "second ssPN molecule". Examples of the first and second ssPN molecules are given below. It should be noted, however, that the present invention is not limited to these illustrative examples.

(1) First ssPN Molecule

The first ssPN molecule is a molecule including the region (X), the region (Xc), and the linker region (Lx), for example.

The first ssPN molecule may include the region (Xc), the linker region (Lx), and the region (X) in this order from the 5' side to the 3' side, or may include the region (Xc), the linker region (Lx), and the region (X) in this order from the 3' side to the 5' side, for example.

In the first ssPN molecule, the region (Xc) is complementary to the region (X). It is only necessary that the region (Xc) has a sequence complementary to the entire region or part of the region (X). Preferably, the region (Xc) includes or is composed of a sequence complementary to the entire region or part of the region (X). The region (Xc) may be perfectly complementary to the entire region or part of the region (X), or one or a few bases in the region (Xc) may be noncomplementary to the same, for example. Preferably, the region (Xc) is perfectly complementary to the same. The expression "one or a few bases" means, for example, 1 to 3 bases, preferably 1 base or 2 bases.

In the first ssPN molecule, the expression inhibitory sequence is included in at least one of the regions (Xc) and (X), as described above. The first ssPN molecule may include one expression inhibitory sequence, or two or more expression inhibitory sequences, for example.

In the latter case, the first ssPN molecule may include, for example: two or more identical expression inhibitory sequences for the same target gene; two or more different expression inhibitory sequences for the same target gene; or two or more different expression inhibitory sequences for different target genes. When the first ssPN molecule includes two or more expression inhibitory sequences, the positions of the respective expression inhibitory sequences are not particularly limited, and they may be in one region or different regions selected from the regions (X) and (Xc). When the first ssPN molecule includes two or more expression inhibitory sequences for different target genes, the first ssPN molecule can inhibit the expressions of two or more kinds of different target genes, for example.

Figure 1B:
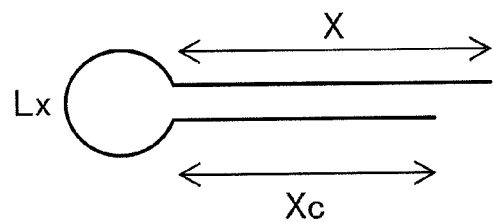

FIG. 1 shows schematic views illustrating an example of the first ssPN molecule. FIG. 1A is a schematic view showing the order of the respective regions in the ssPN molecule, as an illustrative example. FIG. 1B is a schematic view showing the state where a double strand is formed in the ssPN molecule. As shown in FIG. 1B, in the ssPN molecule, a double strand is formed between the regions (Xc) and (X), and the Lx region has a loop structure depending on its length. The schematic views shown in FIG. 1 merely illustrate the order in which the respective regions are linked and the positional relationship of the respective regions forming the double strand, and they do not limit the lengths of the respective regions, the shape of the linker region (Lx), and the like, for example.

In the first ssPN molecule, the number of bases in each of the regions (X) and (Xc) is not particularly limited. Examples of the lengths of the respective regions are given below. However, it is to be noted that the present invention is by no means limited thereto. In the present invention, "the number of bases" means the "length", for example, and it also can be referred to as the "base length". In the present invention, for example, the numerical range regarding the number of bases discloses all the positive integers falling within that range. For example, the description "1 to 4 bases" disclosed all of "1, 2, 3, and 4 bases" (the same applies hereinafter).

The region (Xc) may be perfectly complementary to the entire region of the region (X), for example. In this case, it means that, for example, the region (Xc) is composed of a base sequence complementary to the entire region extending from the 5' end to the 3' end of the region (X). In other words, it means that the region (Xc) has the same base length as the region (X), and all the bases in the region (Xc) are complementary to all the bases in the region (X).

Furthermore, the region (Xc) may be perfectly complementary to part of the region (X), for example. In this case, it means that, for example, the region (Xc) is composed of a base sequence complementary to the part of the region (X). In other words, it means that the region (Xc) is composed of a base sequence whose base length is shorter than the base length of the region (X) by one or more bases, and all the bases in the region (Xc) are complementary to all the bases in the part of the region (X). The part of the region (X) preferably is a region having a base sequence composed of successive bases starting from the base at the end (the 1st base) on the region (Xc) side, for example.

In the first ssPN molecule, the relationship between the number of bases (X) in the region (X) and the number of bases (Xc) in the region (Xc) satisfy the condition (3) or (5), for example. In the former case, specifically, the following condition (11) is satisfied, for example.

$$X > Xc \quad (3)$$

$$X - Xc = 1 \text{ to } 10, \text{ preferably } 1, 2, \text{ or } 3, \text{ more preferably } 1 \text{ or } 2 \quad (11)$$

$$X = Xc \quad (5)$$

When the region (X) and/or the region (Xc) includes the expression inhibitory sequence, the inner region (Z) may be a region composed of the expression inhibitory sequence only or a region including the expression inhibitory sequence, for example. The number of bases in the expression inhibitory sequence is, for example, 19 to 30, preferably 19, 20, or 21. In the region(s) including the expression inhibitory sequence, for example, the expression inhibitory sequence further may have an additional sequence on its 5' side and/or 3' side. The number of bases in the additional sequence is, for example, 1 to 31, preferably 1 to 21, and more preferably 1 to 11.

The number of bases in the region (X) is not particularly limited. When the region (X) includes the expression inhibitory sequence, the lower limit of the number of bases in the region (X) is, for example, 19, and the upper limit of the same is, for example, 50, preferably 30, and more preferably 25. Specifically, the number of bases in the region (X) is, for example, 19 to 50, preferably 19 to 30, and more preferably 19 to 25.

The number of bases in the region (Xc) is not particularly limited. The lower limit of the number of bases in the region (Xc) is, for example, 19, preferably 20, and more preferably 21, and the upper limit of the same is, for example, 50, more preferably 40, and still more preferably 30.

In the ssPN molecule of the present invention, the length of the linker region (Lx) is not particularly limited. The length of the linker region (Lx) preferably is such that, for example, the regions (X) and (Xc) can form a double strand. When the linker region (Lx) includes the nucleotide residue(s) in addition to the non-nucleotide residue(s), the lower limit of the number of bases in the linker region (Lx) is, for example, 1, preferably 2, and more preferably 3, and the upper limit of the same is, for example, 100, preferably 80, and more preferably 50.

The full length of the first ssPN molecule is not particularly limited. In the first ssPN molecule, the lower limit of the total number of bases (the number of bases in the full length ssPN molecule), is, for example, 38, preferably 42, more preferably 50, still more preferably 51, and particularly preferably 52, and the upper limit of the same is, for example, 300, preferably 200, more preferably 150, still more preferably 100, and particularly preferably 80. In the first ssPN molecule, the lower limit of the total number of bases excluding that in the linker region (Lx) is, for example, 38, preferably 42, more preferably 50, still more preferably 51, and particularly preferably 52, and the upper limit of the same is, for example, 300, preferably 200, more preferably 150, still more preferably 100, and particularly preferably 80.

(2) Second ssPN Molecule

The second ssPN molecule is a molecule that further includes a region (Y) and a region (Yc) that is complementary to the region (Y), in addition to the region (X), the linker region (Lx), and the region (Xc), for example. In the second ssPN molecule, an inner region (Z) is composed of the region (X) and the region (Y) that are linked to each other. The description regarding the first ssPN molecule also applies to the second ssPN molecule, unless otherwise stated.

The second ssPN molecule may include, for example, the region (Xc), the linker region (Lx), the region (X), the region (Y), and the region (Yc) in this order from the 5' side to the 3' side. In this case, the region (Xc) also is referred to as a "5' side region (Xc)"; the region (X) in the inner region (Z) also is referred to as an "inner 5' side region (X)"; the region (Y) in the inner region (Z) also is referred to as an "inner 3' region (Y)"; and the region (Yc) also is referred to as a "3' side region (Yc)". Alternatively, the second ssPN molecule may include, for example, the region (Xc), the linker region (Lx), the region (X), the region (Y), and the region (Yc) in this order from the 3' side to the 5' side. In this case, the region (Xc) also is referred to as a "3' side region (Xc)"; the region (X) in the inner region (Z) also is referred to as an "inner 3' side region (X)"; the region (Y) in the inner region (Z) also is referred to as an "inner 5' region (Y)"; and the region (Yc) also is referred to as a "5' side region (Yc)".

As described above, the inner region (Z) is composed of the regions (X) and (Y) that are linked to each other, for example. The regions (X) and (Y) are linked directly to each other with no intervening sequence therebetween, for example. The inner region (Z) is defined as being "composed of the regions (X) and (Y) that are linked to each other" merely to indicate the sequence context between the 5' side region (Xc) and the 3' side region (Xc). This definition does not intend to limit that, in the use of the ssPN molecule, the regions (Xc) and (Y) in the inner region (Z) are discrete independent regions. That is, for example, when the expression inhibitory sequence is included in the inner region (Z), the expression inhibitory sequence may be arranged so as to extend across the regions (X) and (Y) in the inner region (Z).

In the second ssPN molecule, the region (Xc) is complementary to the region (X). It is only necessary that the region (Xc) has a sequence complementary to the entire region or part of the region (X). Preferably, the region (Xc) includes or is composed of a sequence complementary to the entire region or part of the region (X). The region (Xc) may be perfectly complementary to the entire region or part of the region (X), or one or a few bases in the region (Xc) may be noncomplementary to the same, for example. Preferably, the region (Xc) is perfectly complementary to the same. The expression "one or a few bases" means, for example, 1 to 3 bases, preferably 1 base or 2 bases.

In the second ssPN molecule, the region (Yc) is complementary to the region (Y). It is only necessary that the region (Yc) has a sequence complementary to the entire region or part of the region (Y). Preferably, the region (Yc) includes or is composed of a sequence complementary to the entire region or part of the region (Y). The region (Yc) may be perfectly complementary to the entire region or part of the region (Y), or one or a few bases in the region (Yc) may be noncomplementary to the same, for example. Preferably, the region (Yc) is perfectly complementary to the same. The expression "one or a few bases" means, for example, 1 to 3 bases, preferably 1 base or 2 bases.

In the second ssPN molecule, at least one of the inner region (Z), which is composed of the regions (X) and (Y), and the region (Xc) includes the expression inhibitory sequence, for example. Furthermore, the region (Yc) also may include the expression inhibitory sequence. When the inner region (Z) includes the expression inhibitory sequence, either of the regions (X) and (Y) may include the expression inhibitory sequence, or the expression inhibitory sequence may be included so as to extend across the regions (X) and (Y), for example. The second ssPN molecule may include one expression inhibitory sequence, or two or more expression inhibitory sequences, for example.

When the second ssPN molecule includes two or more expression inhibitory sequences, the positions of the respective expression inhibitory sequences are not particularly limited. They may be in either one of the inner region (Z) and the region (Xc), or may be in one of the inner region (Z) and the region (Xc), and any region other than these regions.

In the second ssPN molecule, the regions (Yc) and (Y) may be linked to each other either directly or indirectly, for example. In the former case, the regions (Yc) and (Y) may be linked directly by phosphodiester linkage or the like, for example. In the latter case, the second ssPN molecule may be configured so that it has a linker region (Ly) between the regions (Yc) and (Y), and the regions (Yc) and (Y) are linked via the linker region (Ly), for example.

When the second ssPN molecule has the linker region (Ly), the linker region (Ly) may be a linker composed of the nucleotide residue(s), or a linker having a non-nucleotide structure containing at least one of a pyrrolidine skeleton and a piperidine skeleton such as described above, for example. In the latter case, the linker region (Ly) can be represented by the formula (I), for example, and all the descriptions regarding the formula (I) stated above in connection with the linker region (Lx) also apply to the linker region (Ly).

The regions (Yc) and (Y) are each linked to the linker region (Ly) via —$OR^1$— or —$OR^2$—, for example. In the linker region (Ly), $R^1$ and $R^2$ may or may not be present, as in the above-described linker region (Lx).

The combination of the regions (Xc) and (X) with —$OR^1$— and —$OR^2$—, and the combination of the regions (Yc) and (Y) with —$OR^1$— and —$OR^2$— are not particularly limited, and may be any of the following conditions, for example.

Condition (1):
the regions (Xc) and (X) are linked to the structure of the formula (I) via —$OR^2$— and —$OR^1$—, respectively; and
the regions (Yc) and (Y) are linked to the structure of the formula (I) via —$OR^1$— and —$OR^2$—, respectively.

Condition (2):
the regions (Xc) and (X) are linked to the structure of the formula (I) via —$OR^2$— and —$OR^1$—, respectively; and the regions (Yc) and (Y) are linked to the structure of the formula (I) via —$OR^2$— and —$OR^1$—, respectively.

Condition (3):

the regions (Xc) and (X) are linked to the structure of the formula (I) via —$OR^1$— and —$OR^2$—, respectively; and the regions (Yc) and (Y) are linked to the structure of the formula (I) via —$OR^1$— and —$OR^2$—, respectively.

Condition (4):

the regions (Xc) and (X) are linked to the structure of the formula (I) via —$OR^1$— and —$OR^2$—, respectively; and the regions (Yc) and (Y) are linked to the structure of the formula (I) via —$OR^2$— and —$OR^1$—, respectively.

Figure 2A:
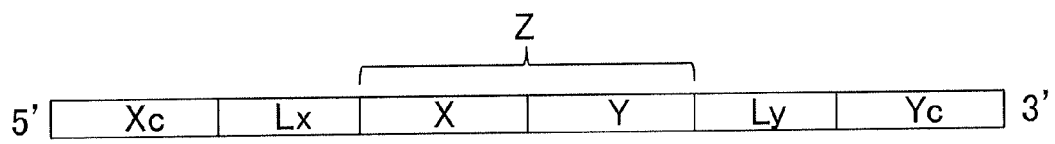
FIG. 2 shows schematic views illustrating another example of the single-stranded nucleic acid molecule of the present invention.
Figure 2B:
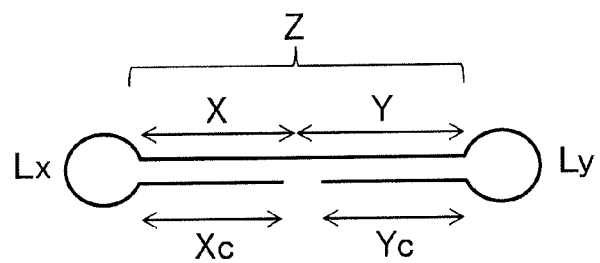
Figure 3A:
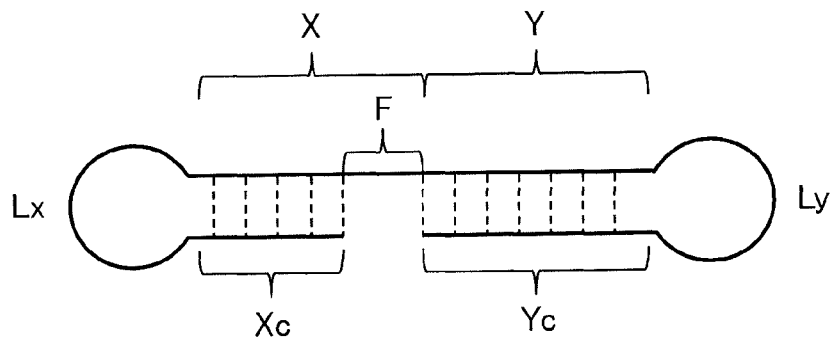
FIG. 3 shows schematic views illustrating other examples of the single-stranded nucleic acid molecule of the present invention.
Figure 3B:
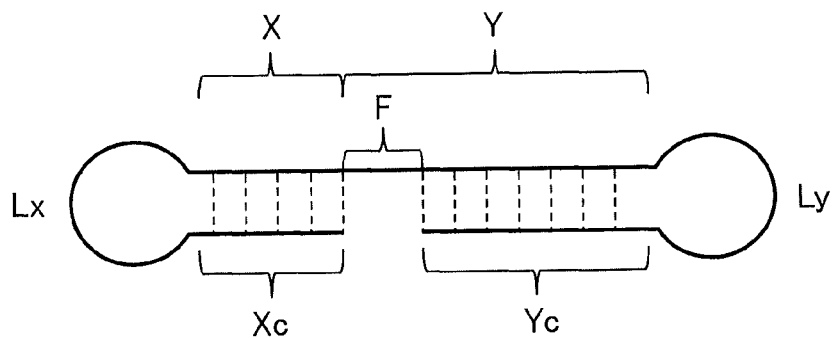
Figure 3C:
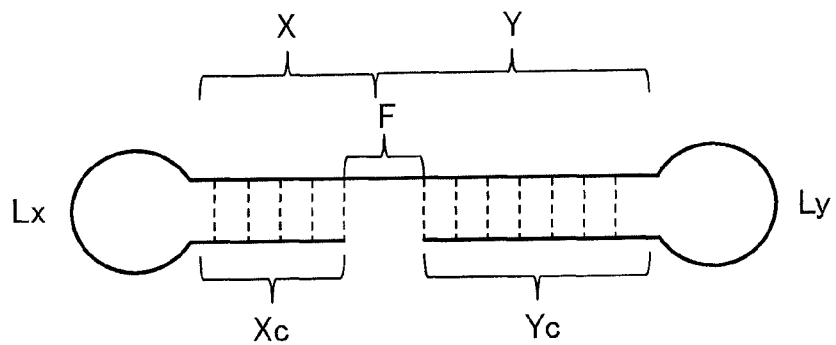
Figure 3D:
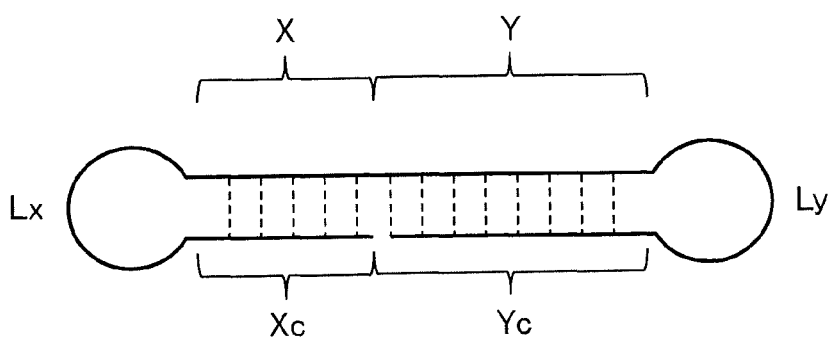

FIG. 2 shows schematic views illustrating an example of the second ssPN molecule having the linker region (Ly). FIG. 2A is a schematic view showing the order of the respective regions from the 5' side to the 3' side in the ssPN molecule, as an illustrative example. FIG. 2B is a schematic view showing the state where double strands are formed in the ssPN molecule. As shown in FIG. 2B, in the ssPN molecule, double strands are formed between the regions (Xc) and (X) and between the regions (Y) and (Yc), and the Lx region and the Ly region each have a loop structure depending on their lengths. The schematic views shown in FIG. 2 merely illustrates the order in which the respective regions are linked and the positional relationship of the respective regions forming the double strand, and they do not limit the lengths of the respective regions, the shape of the linker region, and the like, for example. Furthermore, although the region (Xc) in on the 5' side in FIG. 2, the position of the region (Xc) is not limited thereto, and the region (Xc) may be on the 3' side.

In the second ssPN molecule, the number of bases in each of the regions (Xc), (X), (Y), and (Yc) is not particularly limited. Examples of the lengths of the respective regions are given below. It is to be noted, however, that the present invention is by no means limited thereto.

As described above, the region (Xc) may be complementary to the entire region of the region (X), for example. In this case, it is preferable that, for example, the region (Xc) has the same base length as the region (X), and is composed of a base sequence complementary to the entire region of the region (X). It is more preferable that the region (Xc) has the same base length as the region (X), and all the bases in the region (Xc) are complementary to all the bases in the region (X), i.e., the region (Xc) is perfectly complementary to the region (X), for example. It is to be noted, however, that the configuration of the region (Xc) is not limited thereto, and one or a few bases in the region (Xc) may be noncomplementary to the corresponding bases in the region (X), for example, as described above.

Furthermore, as described above, the region (Xc) may be complementary to part of the region (X), for example. In this case, it is preferable that, for example, the region (Xc) has the same base length as the part of the region (X), i.e., the region (Xc) is composed of a base sequence whose base length is shorter than the base length of the region (X) by one or more bases. It is more preferable that the region (Xc) has the same base length as the part of the region (X) and all the bases in the region (Xc) are complementary to all the bases in the part of the region (X), i.e., the region (Xc) is perfectly complementary to the part of the region (X), for example. The part of the region (X) preferably is a region having a base sequence composed of successive bases starting from the base at the end (the 1st base) on the region (Xc) side in the region (X), for example.

As described above, the region (Yc) may be complementary to the entire region of the region (Y), for example. In this case, it is preferable that, for example, the region (Yc) has the same base length as the region (Y), and is composed of a base sequence complementary to the entire region of the region (Y). It is more preferable that the region (Yc) has the same base length as the region (Y), and all the bases in the region (Yc) are complementary to all the bases in the region (Y), i.e., the region (Yc) is perfectly complementary to the region (Y), for example. It is to be noted, however, that the configuration of the region (Yc) is not limited thereto, and one or a few bases in the region (Yc) may be noncomplementary to the corresponding bases in the region (Y), for example, as described above.

Furthermore, as described above, the region (Yc) may be complementary to part of the region (Y), for example. In this case, it is preferable that, for example, the region (Yc) has the same base length as the part of the region (Y), i.e., the region (Yc) is composed of a base sequence whose base length is shorter than the base length of the region (Y) by one or more bases. It is more preferable that the region (Yc) has the same base length as the part of the region (Y) and all the bases in the region (Yc) are complementary to all the bases in the part of the region (Y), i.e., the region (Yc) is perfectly complementary to the part of the region (Y), for example. The part of the region (Y) preferably is a region having a base sequence composed of successive bases starting from the base at the end (the 1st base) on the region (Yc) side in the region (Y), for example.

In the second ssPN molecule, the relationship of the number of bases (Z) in the inner region (Z) with the number of bases (X) in the region (X) and the number of bases (Y) in the region (Y), and the relationship of the number of bases (Z) in the inner region (Z) with the number of bases (X) in the region (X) and the number of bases (Xc) in the region (Xc) satisfy the conditions of Expressions (1) and (2), for example.

$$Z=X+Y \tag{1}$$

$$Z \geq Xc+Yc \tag{2}$$

In the second ssPN molecule, the length relationship between the number of bases (X) in the region (X) and the number of bases (Y) in the region (Y) is not particularly limited, and satisfy any of the conditions of the following expressions, for example.

$$X=Y \tag{19}$$

$$X<Y \tag{20}$$

$$X>Y \tag{21}$$

In the second ssPN molecule, the relationship between the number of bases (X) in the region (X) and the number of bases (Xc) in the region (Xc), and the relationship between the number of bases (Y) in the region (Y) and the number of bases (Yc) in the region (Yc) satisfy any of the following conditions (a) to (d), for example.

(a) Conditions of Expressions (3) and (4) are satisfied.

$$X>Xc \tag{3}$$

$$Y=Yc \tag{4}$$

(b) Conditions of Expressions (5) and (6) are satisfied.

$$X=Xc \tag{5}$$

$$Y>Yc \tag{6}$$

(c) Conditions of Expressions (7) and (8) are satisfied.

$$X>Xc \tag{7}$$

$$Y>Yc \tag{8}$$

(d) Conditions of Expressions (9) and (10) are satisfied.

$$X = Xc \quad (9)$$

$$Y = Yc \quad (10)$$

In the above-described conditions (a) to (d), the difference between the number of bases (X) in the region (X) and the number of bases (Xc) in the region (Xc), and the difference between the number of bases (Y) in the region (Y) and the number of bases (Yc) in the region (Yc) preferably satisfy the following conditions (a) to (d), for example.

(a) Conditions of Expressions (11) and (12) are satisfied.

$$X - Xc = 1 \text{ to } 10, \text{ preferably } 1, 2, 3 \text{ or } 4, \text{ and more preferably } 1, 2, \text{ or } 3 \quad (11)$$

$$Y - Yc = 0 \quad (12)$$

(b) Conditions of Expressions (13) and (14) are satisfied.

$$X - Xc = 0 \quad (13)$$

$$Y - Yc = 1 \text{ to } 10, \text{ preferably } 1, 2, 3 \text{ or } 4, \text{ and more preferably } 1, 2, \text{ or } 3 \quad (14)$$

(c) Conditions of Expressions (15) and (16) are satisfied.

$$X - Xc = 1 \text{ to } 10, \text{ preferably } 1, 2, \text{ or } 3, \text{ and more preferably } 1 \text{ or } 2 \quad (15)$$

$$Y - Yc = 1 \text{ to } 10, \text{ preferably } 1, 2, \text{ or } 3, \text{ and more preferably } 1 \text{ or } 2 \quad (16)$$

(d) Conditions of Expressions (17) and (18) are satisfied.

$$X - Xc = 0 \quad (17)$$

$$Y - Yc = 0 \quad (18)$$

Regarding the second ssPN molecules satisfying the conditions (a) to (d), examples of their structures are shown respectively in the schematic views of FIG. 3. FIG. 3 shows the ssPN molecules including the linker regions (Lx) and (Ly). FIG. 3A shows an example of the ssPN molecule satisfying the condition (a); FIG. 3B shows an example of the ssPN molecule satisfying the condition (b); FIG. 3C shows an example of the ssPN molecule satisfying the condition (c); and FIG. 3D shows an example of the ssPN molecule satisfying the condition (d). In FIG. 3, dotted lines indicate a state where double strands are formed by self-annealing. The ssPN molecules shown in FIG. 3 are all directed to examples where the relationship between the number of bases (X) in the region (X) and the number of bases (Y) in the region (Y) satisfy "X<Y" of Expression (20). It is to be noted, however, that the relationship is not limited thereto, and "X=Y" of Expression (19) or "X>Y" of Expression (21) may be satisfied. The schematic views shown in FIG. 3 merely illustrate the relationship between the regions (X) and (Xc) and the relationship between the regions (Y) and (Yc), and they do not limit the length, the shape, and the like of each region, and the presence or absence of the linker region (Ly), for example.

Each of the ssPN molecules satisfying the conditions (a) to (c) is configured so that, for example, when the double strands are formed by the regions (Xc) and (X) and by the regions (Yc) and (Y), respectively, the inner region (Z) includes at least one base that cannot be aligned with either of the regions (Xc) and (Yc). In the inner region (Z), the base that is not aligned (a base that does not form the double strand) hereinafter also is referred to as a "unpaired base". In FIG. 3, a region composed of the unpaired base(s) is shown as "F". The number of bases in the region (F) is not particularly limited. The number of bases (F) in the region (F) is as follows, for example: "Xc−X" in the case of the ssPN molecule satisfying the condition (a); "Y−Yc" in the case of the ssPN molecule satisfying the condition (b); and the total of "Xc−X" and "Y−Yc" in the case of the ssPN molecule satisfying the condition (c).

On the other hand, the ssPN molecule satisfying the condition (d) is configured so that, for example, the entire region of the inner region (Z) is aligned with the regions (Xc) and (Yc), in other words, the entire region of the inner region (Z) forms a double strand. In the ssPN molecule satisfying the condition (d), the 5' end of the region (Xc) and the 3' end of the region (Yc) are not linked to each other.

The total number of the bases in the region (Xc), the bases in the region (Yc), and the unpaired bases (F) in the inner region (Z) is equal to the number of the bases in the inner region (Z). Thus, the length of the region (Xc) and the length of the region (Yc) can be determined as appropriate depending on the length of the inner region (Z), the number of the unpaired bases, and the positions of the unpaired bases, for example.

The number of the bases in the inner region (Z) is 19 or more, for example. The lower limit of the number of the bases is, for example, 19, preferably 20, and more preferably 21. The upper limit of the number of the bases is, for example, 50, preferably 40, and more preferably 30. A specific example of the number of the bases in the inner region (Z) is 19, 20, 21, 22, 23, 24, 25, 26, 27, 28, 29, or 30. When the inner region (Z) includes the expression inhibitory sequence, the above condition is preferable, for example.

When the inner region (Z) includes the expression inhibitory sequence, the inner region (Z) may be a region composed of the expression inhibitory sequence only or a region including the expression inhibitory sequence, for example. The number of bases of the expression inhibitory sequence is, for example, 19 to 30, preferably 19, 20, or 21. When the inner region (Z) includes the expression inhibitory sequence, the expression inhibitory sequence may further have an additional sequence on its 5' side and/or 3' side. The number of bases in the additional sequence is, for example, 1 to 31, preferably 1 to 21, more preferably 1 to 11, and still more preferably 1 to 7.

The number of bases in the region (Xc) is, for example, 1 to 29, preferably 1 to 11, more preferably 1 to 7, still more preferably 1 to 4, and particularly preferably 1, 2, or 3. When the inner region (Z) or the region (Yc) includes the expression inhibitory sequence, the number of bases as described above is preferable, for example. A specific example is as follows: when the number of bases in the inner region (Z) is 19 to 30 (e.g., 19), the number of bases in the region (Xc) is, for example, 1 to 11, preferably 1 to 7, more preferably 1 to 4, and still more preferably 1, 2, or 3.

When the region (Xc) includes the expression inhibitory sequence, the region (Xc) may be a region composed of the expression inhibitory sequence only or a region including the expression inhibitory sequence, for example. The length of the expression inhibitory sequence is as described above, for example. When the region (Xc) includes the expression inhibitory sequence, the expression inhibitory sequence further may have an additional sequence on its 5' side and/or 3' side. The number of bases in the additional sequence is, for example, 1 to 11, preferably 1 to 7.

The number of bases in the region (Yc) is, for example, 1 to 29, preferably 1 to 11, more preferably 1 to 7, still more preferably 1 to 4, and particularly preferably 1, 2, or 3. When the inner region (Z) or the region (Xc) includes the expression inhibitory sequence, the number of bases as described above is preferable, for example. A specific example is as follows: when the number of bases in the inner region (Z) is 19 to 30

(e.g., 19), the number of bases in the region (Yc) is, for example, 1 to 11, preferably 1 to 7, more preferably 1, 2, 3, or 4, and still more preferably 1, 2, or 3.

When the region (Yc) includes the expression inhibitory sequence, the region (Yc) may be a region composed of the expression inhibitory sequence only or a region including the expression inhibitory sequence, for example. The length of the expression inhibitory sequence is as described above, for example. When the region (Yc) includes the expression inhibitory sequence, the expression inhibitory sequence further may have an additional sequence on its 5' side and/or 3' side. The number of bases in the additional sequence is, for example, 1 to 11, preferably 1 to 7.

As described above, the relationship among the number of bases in the inner region (Z), the number of bases in the region (Xc), and the number of bases in the region (Ye) can be expressed by Expression (2): "Z≧Xc+Yc", for example. Specifically, the number of bases represented by "Xc+Yc" is equal to the number of bases in the inner region (Z), or lower than the number of bases in the inner region (Z), for example. In the latter case, "Z−(Xc+Ye)" is, for example, 1 to 10, preferably 1 to 4, and more preferably 1, 2, or 3. The "Z−(Xc+Ye)" corresponds to the number of bases (F) in the unpaired base region (F) in the inner region (Z), for example.

In the second ssPN molecule, the lengths of the linker regions (Lx) and (Ly) are not particularly limited. The linker region (Lx) is as described above. When the components (building blocks) of the linker region (Ly) include a base(s), the lower limit of the number of bases in the linker region (Ly) is, for example, 1, preferably 2, and more preferably 3, and the upper limit of the same is, for example, 100, preferably 80, and more preferably 50. The number of bases in each of the linker regions specifically is 1 to 50, 1 to 30, 1 to 20, 1 to 10, 1 to 7, or 1 to 4, for example, but it is not limited to these illustrative examples.

The linker region (Lx) may be the same as or different from the linker region (Ly), for example.

The full length of the second ssPN molecule is not particularly limited. In the second ssPN molecule, the lower limit of the total number of bases (the number of bases in the full length ssPN molecule), is, for example, 38, preferably 42, more preferably 50, still more preferably 51, and particularly preferably 52, and the upper limit of the same is, for example, 300, preferably 200, more preferably 150, still more preferably 100, and particularly preferably 80. In the second ssPN molecule, the lower limit of the total number of bases excluding those in the linker regions (Lx) and (Ly) is, for example, 38, preferably 42, more preferably 50, still more preferably 51, and particularly preferably 52, and the upper limit of the same is, for example, 300, preferably 200, more preferably 150, still more preferably 100, and particularly preferably 80.

In the ssPN molecule of the present invention, it is only necessary that the linker region (Lx) has the non-nucleotide structure as described above, and other components are not particularly limited. Examples of the components include nucleotide residues. Examples of the nucleotide residues include a ribonucleotide residue and a deoxyribonucleotide residue. The nucleotide residue may be the one that is not modified (unmodified nucleotide residue) or the one that has been modified (modified nucleotide residue), for example. By configuring the ssPN molecule of the present invention so as to include a modified nucleotide residue, for example, the resistance of the ssPN molecule to nuclease can be improved, thereby allowing the stability of the ssPN molecule to be improved. Furthermore, the ssPN molecule of the present invention further may include, for example, a non-nucleotide residue in addition to the nucleotide residue.

The nucleotide residue is preferable as the component of each of the regions (Xc), (X), (Y), and (Yc). Each of the regions is composed of any of the following residues (1) to (3), for example.

(1) an unmodified nucleotide residue(s)
(2) a modified nucleotide residue(s)
(3) an unmodified nucleotide residue(s) and a modified nucleotide residue(s)

The linker region (Lx) may be composed of the non-nucleotide residue(s) only, or may be composed of the non-nucleotide(s) and the nucleotide residue(s), for example. The linker region (Lx) is composed of any of the following residues (4) to (7), for example.

(4) a non-nucleotide residue(s)
(5) a non-nucleotide residue(s) and an unmodified nucleotide residue(s)
(6) a non-nucleotide residue(s) and a modified nucleotide residue(s)
(7) a non-nucleotide residue(s), an unmodified nucleotide residue(s), and a modified nucleotide residue(s)

The components of the linker region (Ly) are not particularly limited, and examples thereof include the nucleotide residues and the non-nucleotide residues, as described above. Each of the linker regions may be composed of the nucleotide residue(s) only, the non-nucleotide residue(s) only, or both the nucleotide residue(s) and the non-nucleotide residue(s). Each of the linker regions is composed of any of the following residues (1) to (7), for example.

(1) an unmodified nucleotide residue(s)
(2) a modified nucleotide residue(s)
(3) an unmodified nucleotide residue(s) and a modified nucleotide residue(s)
(4) a non-nucleotide residue(s)
(5) a non-nucleotide residue(s) and an unmodified nucleotide residue(s)
(6) a non-nucleotide residue(s) and a modified nucleotide residue(s)
(7) a non-nucleotide residue(s), an unmodified nucleotide residue(s), and a modified nucleotide residue(s)

The ssPN molecule of the present invention may be, for example: a molecule composed of the nucleotide residues only except for its linker region (Lx); a molecule including the non-nucleotide residue(s) in addition to the nucleotide residues; or the like. In the ssPN molecule of the present invention, the nucleotide residues may be the unmodified nucleotide residues only; the modified nucleotide residues only; or both the unmodified nucleotide residue(s) and the modified nucleotide residue(s), as described above, for example. When the ssPN molecule includes both the unmodified nucleotide residue(s) and the modified nucleotide residue(s), the number of the modified nucleotide residue(s) is not particularly limited, and is, for example, "one or more", specifically, for example, 1 to 5, preferably 1 to 4, more preferably 1 to 3, and most preferably 1 or 2. When the ssPN molecule of the present invention include the non-nucleotide residue(s), the number of the non-nucleotide residue(s) is not particularly limited, and is, for example, "one or more", specifically, for example, 1 or 2.

In the ssPN molecule of the present invention, the nucleotide residue preferably is a ribonucleotide residue, for example. In this case, the ssPN molecule of the present invention also is referred to as an "RNA molecule" or "ssRNA molecule", for example. The ssRNA molecule may be, for example: a molecule composed of the ribonucleotide residues only except for its linker region (Lx); a molecule including the non-nucleotide residue(s) in addition to the ribonucleotide residues; or the like. As described above, as the ribonucleotide residues, the ssRNA molecule may include: the unmodified ribonucleotide residues only; modified ribonucleotide residues only; or both the unmodified ribonucleotide residue(s) and the modified ribonucleotide residue(s), for example.

When the ssRNA molecule includes the modified ribonucleotide residue(s) in addition to the unmodified ribonucleotide residues, for example, the number of the modified ribonucleotide residue(s) is not particularly limited, and is, for example, "one or more", specifically, for example, 1 to 5, preferably 1 to 4, more preferably 1 to 3, and most preferably 1 or 2. Examples of the modified ribonucleotide residue as contrasted to the unmodified ribonucleotide residue include the deoxyribonucleotide residue obtained by substituting a ribose residue with a deoxyribose residue. When the ssRNA molecule includes the deoxyribonucleotide residue(s) in addition to the unmodified ribonucleotide residue(s), for example, the number of the deoxyribonucleotide residue(s) is not particularly limited, and is, for example, "one or more", specifically, for example, 1 to 5, preferably 1 to 4, more preferably 1 to 3, and most preferably 1 or 2.

The ssPN molecule of the present invention may include a labeling substance (marker), and may be labeled with the labeling substance, for example. The labeling substance is not particularly limited, and may be a fluorescent substance, a dye, an isotope, or the like, for example. Examples of the fluorescent substance include: fluorophores such as pyrene, TAMRA, fluorescein, a $Cy_3$ dye, and a $Cy_5$ dye. Examples of the dye include Alexa dyes such as Alexa 488. Examples of the isotope include stable isotopes and radioisotopes. Among them, stable isotopes are preferable. Stable isotopes have a low risk of radiation exposure, and they require no dedicated facilities, for example. Thus, stable isotopes are excellent in handleability and can contribute to cost reduction. Moreover, a stable isotope does not change the physical properties of a compound labeled therewith, for example, and thus has an excellent property as a tracer. The stable isotope is not particularly limited, and examples thereof include $^{2}H$, $^{13}C$, $^{15}N$, $^{17}O$, $^{18}O$, $^{33}S$, $^{34}S$, and $^{36}S$.

In the ssPN molecule of the present invention, as described above, it is preferable to introduce the labeling substance into the non-nucleotide structure, more preferably to the non-nucleotide residue(s) in the linker region (Lx), for example. Introduction of the labeling substance to the non-nucleotide residue(s) can be carried out easily and at low cost, for example.

As described above, the ssPN molecule of the present invention can inhibit the expression of a target gene. Thus, the ssPN molecule of the present invention can be used as a therapeutic agent for treating a disease caused by a gene, for example. According to the ssPN molecule including, as the expression inhibitory sequence, a sequence that inhibits expression of a gene causing the disease, for example, it is possible to treat the disease by inhibiting the expression of the target gene. In the present invention, the term "treatment" encompasses: prevention of diseases; improvement of diseases; and improvement in prognosis, for example, and it can mean any of them.

The method of using the ssPN molecule of the present invention is not particularly limited. For example, the ssPN molecule may be administered to a subject having the target gene.

Examples of the subject to which the ssPN molecule of the present invention is administered include cells, tissues, and organs. Examples of the subject also include humans and nonhuman animals such as nonhuman mammals, i.e., mammals excluding humans. The administration may be performed in vivo or in vitro, for example. The cells are not particularly limited, and examples thereof include: various cultured cells such as HeLa cells, 293 cells, NIH3T3 cells, and COS cells; stem cells such as ES cells and hematopoietic stem cells; and cells isolated from living organisms, such as primary cultured cells.

In the present invention, the target gene whose expression is to be inhibited is not particularly limited, and any desired gene can be set as the target gene. The expression inhibitory sequence may be designed as appropriate depending on the kind of the target gene.

Specific examples of the ssPN molecule of the present invention will be given below. It is to be noted, however, that the present invention is by no means limited thereto. Examples of the base sequence of the ssPN molecule include: base sequences of SEQ ID NOs: 3, 11, 14 to 17, and 23; and base sequences obtained by, for example, deletion, substitution, and/or addition of one or more bases in these base sequences. When the target gene is the GAPDH gene, examples of the base sequence of the ssPN molecule include the base sequences of SEQ ID NOs: 3 and 11. When the target gene is the TGF-β31, examples of the base sequence of the ssPN molecule include the base sequences of SEQ ID NOs: 14 to 17 and 23.

As to the use of the ssPN molecule of the present invention, the following descriptions regarding the composition, the inhibitory method, the treatment method, and the like according to the present invention can be referred to.

Since the ssPN molecule of the present invention can inhibit the expression of a target gene as described above, it is useful as a pharmaceutical, a diagnostic agent, an agricultural chemical, and a tool for conducting research on agricultural chemicals, medical science, life science, and the like, for example.

In the present invention, the term "alkyl" encompasses straight-chain and branched alkyl groups, for example. The number of carbon atoms in the alkyl is not particularly limited, and is, for example, 1 to 30, preferably 1 to 6 or 1 to 4. Examples of the alkyl group include: methyl, ethyl, n-propyl, isopropyl, n-butyl, isobutyl, sec-butyl, tert-butyl, n-pentyl, isopentyl, neopentyl, n-hexyl, isohexyl, n-heptyl, n-octyl, n-nonyl, and n-decyl. Among them, methyl, ethyl, n-propyl, isopropyl, n-butyl, isobutyl, sec-butyl, tert-butyl, n-pentyl, isopentyl, neopentyl, n-hexyl, isohexyl, and the like are preferable, for example.

In the present invention, the term "alkenyl" encompasses straight-chain and branched alkenyls, for example. Examples of the alkenyl include the above-described alkyls having one or more double bonds. The number of carbon atoms in the alkenyl is not particularly limited, and is, for example, the same as that in the alkyl, preferably 2 to 8. Examples of the alkenyl include vinyl, 1-propenyl, 2-propenyl, 1-butenyl, 2-butenyl, 3-butenyl, 1,3-butadienyl, and 3-methyl-2-butenyl.

In the present invention, the term "alkynyl" encompasses straight-chain and branched alkynyls, for example. Examples of the alkynyl include the above-described alkyls having having one or more triple bonds. The number of carbon atoms in the alkynyl is not particularly limited, and is, for example, the same as that in the alkyl, preferably 2 to 8. Examples of the alkynyl include ethynyl, propynyl, and butynyl. The alkynyl may further include one or more double bonds, for example.

In the present invention, the term "aryl" encompasses monocyclic aromatic hydrocarbon groups and polycyclic aromatic hydrocarbon groups, for example. Examples of the monocyclic aromatic hydrocarbon group include phenyl.

Examples of the polycyclic aromatic hydrocarbon group include 1-naphthyl, 2-naphthyl, 1-anthryl, 2-anthryl, 9-anthryl, 1-phenanthryl, 2-phenanthryl, 3-phenanthryl, 4-phenanthryl, and 9-phenanthryl. Among them, phenyl, naphthyls such as 1-naphthyl and 2-naphthyl, and the like are preferable, for example.

In the present invention, the term "heteroaryl" encompasses monocyclic aromatic heterocyclic groups and condensed aromatic heterocyclic groups, for example. Examples of the heteroaryl include furyls (e.g.: 2-furyl, 3-furyl), thienyls (e.g.: 2-thienyl, 3-thienyl), pyrrolyls (e.g.: 1-pyrrolyl, 2-pyrrolyl, 3-pyrrolyl), imidazolyls (e.g.: 1-imidazolyl, 2-imidazolyl, 4-imidazolyl), pyrazolyls (e.g.: 1-pyrazolyl, 3-pyrazolyl, 4-pyrazolyl), triazolyls (e.g.: 1,2,4-triazole-1-yl, 1,2,4-triazole-3-yl, 1,2,4-triazole-4-yl), tetrazolyls (e.g.: 1-tetrazolyl, 2-tetrazolyl, 5-tetrazolyl), oxazolyls (e.g.: 2-oxazolyl, 4-oxazolyl, 5-oxazolyl), isoxazolyls (e.g.: 3-isoxazolyl, 4-isoxazolyl, 5-isoxazolyl), thiazolyls (e.g.: 2-thiazolyl, 4-thiazolyl, 5-thiazolyl), thiadiazolyls, isothiazolyls (e.g.: 3-isothiazolyl, 4-isothiazolyl, 5-isothiazolyl), pyridyls (e.g.: 2-pyridyl, 3-pyridyl, 4-pyridyl), pyridazinyls (e.g.: 3-pyridazinyl, 4-pyridazinyl), pyrimidinyls (e.g.: 2-pyrimidinyl, 4-pyrimidinyl, 5-pyrimidinyl), furazanyls (e.g.: 3-furazanyl), pyrazinyls (e.g.: 2-pyrazinyl), oxadiazolyls (e.g.: 1,3,4-oxadiazole-2-yl), benzofuryls (e.g.: 2-benzo[b]furyl, 3-benzo[b]furyl, 4-benzo[b]furyl, 5-benzo[b]furyl, 6-benzo[b]furyl, 7-benzo[b]furyl), benzothienyls (e.g.: 2-benzo[b]thienyl, 3-benzo[b]thienyl, 4-benzo[b]thienyl, 5-benzo[b]thienyl, 6-benzo[b]thienyl, 7-benzo[b]thienyl), benzimidazolyls (e.g.: 1-benzimidazolyl, 2-benzimidazolyl, 4-benzimidazolyl, 5-benzimidazolyl), dibenzofuryls, benzoxazolyls, benzothiazolyls, quinoxalyls (e.g.: 2-quinoxalinyl, 5-quinoxalinyl, 6-quinoxalinyl), cinnolinyls (e.g.: 3-cinnolinyl, 4-cinnolinyl, 5-cinnolinyl, 6-cinnolinyl, 7-cinnolinyl, 8-cinnolinyl), quinazolyls (e.g.: 2-quinazolinyl, 4-quinazolinyl, 5-quinazolinyl, 6-quinazolinyl, 7-quinazolinyl, 8-quinazolinyl), quinolyls (e.g.: 2-quinolyl, 3-quinolyl, 4-quinolyl, 5-quinolyl, 6-quinolyl, 7-quinolyl, 8-quinolyl), phthalazinyls (e.g.: 1-phthalazinyl, 5-phthalazinyl, 6-phthalazinyl), isoquinolyls (e.g.: 1-isoquinolyl, 3-isoquinolyl, 4-isoquinolyl, 5-isoquinolyl, 6-isoquinolyl, 7-isoquinolyl, 8-isoquinolyl), puryls, pteridinyls (e.g.: 2-pteridinyl, 4-pteridinyl, 6-pteridinyl, 7-pteridinyl), carbazolyls, phenanthridinyls, acridinyls (e.g.: 1-acridinyl, 2-acridinyl, 3-acridinyl, 4-acridinyl, 9-acridinyl), indolyls (e.g.: 1-indolyl, 2-indolyl, 3-indolyl, 4-indolyl, 5-indolyl, 6-indolyl, 7-indolyl), isoindolyls, phenazinyls (e.g.: 1-phenazinyl, 2-phenazinyl), and phenothiazinyls (e.g.: 1-phenothiazinyl, 2-phenothiazinyl, 3-phenothiazinyl, 4-phenothiazinyl).

In the present invention, the term "cycloalkyl" refers to cyclic saturated hydrocarbon groups, for example, and the number of carbon atoms in the cycloalkyl is 3 to 15, for example. Examples of the cycloalkyl include cyclopropyl, cyclobutyl, cyclopentyl, cyclohexyl, cycloheptyl, cyclooctyl, bridged cyclic hydrocarbon groups, and spiro hydrocarbon groups. Among them, cyclopropyl, cyclobutyl, cyclopentyl, cyclohexyl, bridged cyclic hydrocarbons, and the like are preferable.

In the present invention, examples of the "bridged cyclic hydrocarbon groups" include bicyclo[2.1.0]pentyl, bicyclo[2.2.1]heptyl, bicyclo[2.2.2]octyl, and bicyclo[3.2.1]octyl, tricyclo[2.2.1.0]heptyl, bicyclo[3.3.1]nonane, 1-adamantyl, and 2-adamantyl.

In the present invention, examples of the "spiro hydrocarbon groups" include spiro[3.4]octyl.

In the present invention, the term "cycloalkenyl" encompasses unsaturated cyclic aliphatic hydrocarbon groups, for example, and the number of carbon atoms in the cycloalkenyl is 3 to 7, for example. Examples of the cycloalkenyl group include cyclopropenyl, cyclobutenyl, cyclopentenyl, cyclohexenyl, and cycloheptenyl. Among them, cyclopropenyl, cyclobutenyl, cyclopentenyl, cyclohexenyl, and the like are preferable. The term "cycloalkenyl" also encompasses bridged cyclic hydrocarbon groups and spiro hydrocarbon groups having an unsaturated bond in their rings, for example.

In the present invention, examples of the "arylalkyl" include benzyl, 2-phenethyl, and naphthalenylmethyl. Examples of the "cycloalkylalkyl" and "cyclylalkyl" include cyclohexylmethyl and adamantylmethyl. Examples of the "hydroxyalkyl" include hydroxymethyl and 2-hydroxyethyl.

In the present invention, the "alkoxy" encompasses groups composed of any of the above-described alkyls and oxygen (alkyl-O-groups), for example, and examples thereof include methoxy, ethoxy, n-propoxy, isopropoxy, and n-butoxy. Examples of the "alkoxyalkyl" include methoxymethyl. Examples of the "aminoalkyl" include 2-aminoethyl.

In the present invention, examples of the "heterocyclyl" include 1-pyrrolinyl, 2-pyrrolinyl, 3-pyrrolinyl, 1-pyrrolidinyl, 2-pyrrolidinyl, 3-pyrrolidinyl, pyrrolidinone, 1-imidazoliny, 2-imidazoliny, 4-imidazoliny, 1-imidazolidinyl, 2-imidazolidinyl, 4-imidazolidinyl, imidazolidinone, 1-pyrazolinyl, 3-pyrazolinyl, 4-pyrazolinyl, 1-pyrazolidinyl, 3-pyrazolidinyl, 4-pyrazolidinyl, piperidinone, piperidino, 2-piperidinyl, 3-piperidinyl, 4-piperidinyl, 1-piperazinyl, 2-piperazinyl, piperazinone, 2-morpholinyl, 3-morpholinyl, morpholino, tetrahydropyranyl, and tetrahydrofuranyl.

In the present invention, examples of the "heterocyclylalkyl" include piperidinylmethyl and piperazinylmethyl. Examples of the "heterocyclylalkenyl" include 2-piperidinyl ethenyl. Examples of the "heteroarylalkyl" include pyridylmethyl and quinoline-3-ylmethyl.

In the present invention, the term "silyl" encompasses groups represented by the formula R3Si—, where R independently can be selected from the above-described alkyls, aryls, and cycloalkyls. Examples of the silyl include a trimethylsilyl group and a tert-butyldimethylsilyl group. Examples of the "silyloxy" include a trimethylsilyloxy group. Examples of the "silyloxyalkyl" include trimethylsilyloxymethyl.

In the present invention, examples of the "alkylene" include methylene, ethylene, and propylene.

In the present invention, the above-described various groups may be substituted. Examples of the substituent include hydroxy, carboxy, halogens, alkyl halides (e.g.: $CF_3$, $CH_2CF_3$, $CH_2CCl_3$), nitro, nitroso, cyano, alkyls (e.g.: methyl, ethyl, isopropyl, tert-butyl), alkenyls (e.g.: vinyl), alkynyls (e.g.: ethynyl), cycloalkyls (e.g.: cyclopropyl, adamantyl), cycloalkylalkyls (e.g.: cyclohexylmethyl, adamantylmethyl), cycloalkenyls (e.g.: cyclopropenyl), aryls (e.g.: phenyl, naphthyl), arylalkyls (e.g.: benzyl, phenethyl), heteroaryls (e.g.: pyridyl, furyl), heteroarylalkyls (e.g.: pyridylmethyl), heterocyclyls (e.g.: piperidyl), heterocyclylalkyls (e.g.: morpholylmethyl), alkoxys (e.g.: methoxy, ethoxy, propoxy, butoxy), halogenated alkoxys (e.g.: $OCF_3$), alkenyloxys (e.g.: vinyloxy, allyloxy), aryloxys (e.g.: phenyloxy), alkyloxycarbonyls (e.g.: methoxycarbonyl, ethoxycarbonyl, tert-butoxycarbonyl), arylalkyloxys (e.g.: benzyloxy), aminos [alkylaminos (e.g.: methylamino, ethylamino, dimethylamino), acylaminos (e.g.: acetylamino, benzoylamino), arylalkylaminos (e.g.: benzylamino, tritylamino), hydroxyamino], alkylaminoalkyls (e.g.: diethylaminomethyl), sulfamoyl, and oxo.

2. Nucleotide Residue

The nucleotide residue includes, as its components, a sugar, a base, and a phosphate. The nucleotide residue may be, for example, a ribonucleotide residue or a deoxyribonucleotide residue, as described above. The ribonucleotide residue has, for example: a ribose residue as the sugar; and adenine (A), guanine (G), cytosine (C), or uracil (U) as the base. The deoxyribose residue has, for example: a deoxyribose residue as the sugar; and adenine (A), guanine (G), cytosine (C), or thymine (T) as the base.

The nucleotide residue may be, for example, an unmodified nucleotide residue or a modified nucleotide residue. The components of the unmodified nucleotide residue are the same or substantially the same as the components of a naturally-occurring nucleotide residue, for example. Preferably, the components are the same or substantially the same as the components of a nucleotide residue occurring naturally in a human body.

The modified nucleotide residue is a nucleotide residue obtained by modifying the unmodified nucleotide residue, for example. The modified nucleotide may be such that any of the components of the unmodified nucleotide residue is modified, for example. In the present invention, "modification" means, for example: substitution, addition, and/or deletion of any of the components; and substitution, addition, and/or deletion of an atom(s) and/or a functional group(s) in the component(s). It also can be referred to as "alteration". Examples of the modified nucleotide residue include naturally-occurring nucleotide residues and artificially-modified nucleotide residues. Regarding the naturally-derived modified nucleotide residues, Limbach et al. (1994, Summary: the modified nucleosides of RNA, Nucleic Acids Res. 22: pp. 2183 to 2196) can be referred to, for example. The modified nucleotide residue may be a residue of an alternative of the nucleotide, for example.

Examples of the modification of the nucleotide residue include modification of a ribose-phosphate backbone (hereinafter referred to as a "ribophosphate backbone").

In the ribophosphate backbone, a ribose residue may be modified, for example. In the ribose residue, for example, the 2'-position carbon can be modified. Specifically, a hydroxyl group bound to the 2'-position carbon can be substituted with hydrogen, fluoro, or the like, for example. By substituting the hydroxyl group bound to the 2'-position carbon with hydrogen, it is possible to substitute the ribose residue with deoxyribose. The ribose residue can be substituted with its stereoisomer, for example, and may be substituted with an arabinose residue, for example.

The ribophosphate backbone may be substituted with a non-ribophosphate backbone having a non-ribose residue and/or a non-phosphate, for example. The non-ribophosphate backbone may be, for example, the ribophosphate backbone modified so as to be uncharged, or the like. Examples of an alternative obtained by substituting the ribophosphate backbone with the non-ribophosphate backbone in the nucleotide include morpholino, cyclobutyl, and pyrrolidine. Other examples of the alternative include artificial nucleic acid monomer residues. Specific examples thereof include PNA (Peptide Nucleic Acid), LNA (Locked Nucleic Acid), and ENAs (2'-O,4'-C-Ethylenebridged Nucleic Acids). Among them, PNA is preferable.

In the ribophosphate backbone, a phosphate group can be modified, for example. In the ribophosphate backbone, a phosphate group in the closest proximity to the sugar residue is called an "α-phosphate group". The α-phosphate group is charged negatively, and the electric charges are distributed evenly over two oxygen atoms that are not linked to the sugar residue. Among the four oxygen atoms in the α-phosphate group, the two oxygen atoms not linked to the sugar residue in the phosphodiester linkage between the nucleotide residues hereinafter are referred to as "non-linking oxygens". On the other hand, two oxygen atoms that are linked to the sugar residue in the phosphodiester linkage between the nucleotide residues hereinafter are referred to as "linking oxygens". The α-phosphate group preferably is modified so as to be uncharged, or so as to render the charge distribution between the non-linking atoms asymmetric, for example.

In the phosphate group, the non-linking oxygen(s) may be substituted, for example. The oxygen(s) can be substituted with any atom selected from S (sulfur), Se (selenium), B (boron), C (carbon), H (hydrogen), N (nitrogen), and OR (R is an alkyl group or an aryl group, for example), for example, and substitution with S is preferable. It is preferable that both the non-linking oxygens are substituted, for example, and it is more preferable that both the non-linking oxygens are substituted with S. Examples of the thus-modified phosphate group include phosphorothioates, phosphorodithioates, phosphoroselenates, borano phosphates, borano phosphate esters, hydrogen phosphonates, phosphoroamidates, alkyl or aryl phosphonates, and phosphotriesters. In particular, phosphorodithioate in which both of the two non-linking oxygens are substituted with S is preferable.

In the phosphate group, the linking oxygen(s) may be substituted, for example. The oxygen(s) can be substituted with any atom selected from S (sulfur), C (carbon), and N (nitrogen), for example. Examples of the thus-modified phosphate group include: bridged phosphoroamidates resulting from the substitution with N; bridged phosphorothioates resulting from the substitution S; and bridged methylenephosphonates resulting from the substitution C. Preferably, substitution of the linking oxygen(s) is performed in at least one of the 5' end nucleotide residue and the 3' end nucleotide residue of the ssPN molecule of the present invention, for example. When the substitution is performed on the 5' side, substitution with C is preferable. When the substitution is performed on the 3' side, substitution with N is preferable.

The phosphate group may be substituted with the phosphate-free linker, for example. The linker may contain siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo, methyleneoxymethylimino, or the like. Preferably, the linker may contain a methylene carbonyl amino group and a methylenemethylimino group.

In the ssPN molecule of the present invention, for example, at least one of a nucleotide residue at the 3' end and a nucleotide residue at the 5' end may be modified. The nucleotide residue at either one of the 3' end and the 5' end may be modified, or the nucleotide residues at both the 3' end and the 5' end may be modified, for example. The modification may be as described above, for example, and it is preferable to modify a phosphate group(s) at the end(s). The entire phosphate group may be modified, or one or more atoms in the phosphate group may be modified, for example. In the former case, for example, the entire phosphate group may be substituted or deleted.

Modification of the nucleotide residue(s) at the end(s) may be addition of any other molecule, or the like, for example. Examples of the other molecule include functional molecules such as labeling substances as described above and protecting groups. Examples of the protecting groups include S (sulfur), Si (silicon), B (boron), and ester-containing groups. The functional molecules such as the labeling substances can be used in the detection and the like of the ssPN molecule of the present invention, for example.

The other molecule may be added to the phosphate group of the nucleotide residue, or may be added to the phosphate group or the sugar residue via a spacer, for example. The terminal atom of the spacer can be added to or substituted for either one of the linking oxygens of the phosphate group, or O, N, S, or C of the sugar residue, for example. The binding site in the sugar residue preferably is, for example, C at the 3'-position, C at the 5'-position, or any atom bound thereto. The spacer also can be added to or substituted for a terminal atom of the nucleotide alternative such as PNA, for example.

The spacer is not particularly limited, and examples thereof include —$(CH_2)_n$—, —$(CH_2)_n$N—, —$(CH_2)_n$O—, —$(CH_2)_n$ S—, $O(CH_2CH_2O)_nCH_2CH_2OH$, abasic sugars, amide, carboxy, amine, oxyamine, oxyimine, thioether, disulfide, thiourea, sulfonamide, and morpholino, and also biotin reagents and fluorescein reagents. In the above formulae, n is a positive integer, and n=3 or 6 is preferable.

Other examples of the molecule to be added to the end include dyes, intercalating agents (e.g., acridines), crosslinking agents (e.g., psoralen, mitomycin C), porphyrins (TPPC4, texaphyrin, Sapphyrin), polycyclic aromatic hydrocarbons (e.g., phenazine, dihydrophenazine), artificial endonucleases (e.g., EDTA), lipophilic carriers (e.g., cholesterol, cholic acid, adamantane acetic acid, 1-pyrene butyric acid, dihydrotestosterone, 1,3-Bis-O (hexadecyl)glycerol, a geranyloxyhexyl group, hexadecylglycerol, borneol, menthol, 1,3-propanediol, a heptadecyl group, palmitic acid, myristic acid, O3-(oleoyl)lithocholic acid, O3-(oleoyncholic acid, dimethoxytrityl, or phenoxazine), peptide complexes (e.g., Antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g., biotin), transport/absorption facilitators (e.g., aspirin, vitamin E, folic acid), and synthetic ribonucleases (e.g., imidazole, bisimidazole, histamine, imidazole clusters, acridine-imidazole complexes, $Eu^{3+}$ complexes of tetraazamacrocycles).

In the ssPN molecule of the present invention, the 5' end may be modified with a phosphate group or a phosphate group analog, for example. Examples of the phosphate group include:
5'-monophosphate((HO)$_2$(O)P—O-5');
5'-diphosphate((HO)$_2$(O)P—O—P(HO)(O)—O-5);
5'-triphosphate(HO)$_2$(O)P—O—(HO)(O)P—O—P(HO)(O)—O-5);
5'-guanosine cap (7-methylated or non-methylated, 7m-G-O-5'-(HO)(O)P—O—(HO)(O)P—O—P(HO)(O)—O-5);
5'-adenosine cap (Appp);
any modified or unmodified nucleotide cap structure (N—O-5'-(HO)(O)P—O—(HO)(O)P—O—P(HO)(O)—O-5);
5'-monothiophosphate (phosphorothioate: (HO)$_2$(S)P—O-5);
5'-monodithiophosphate (phosphorodithioate: (HO)(HS)(S)P—O-5);
5'-phosphorothiolate ((HO)$_2$(O)P—S-5);
sulfur substituted monophosphate, diphosphate, and triphosphates (e.g., 5'-α-thiotriphosphate, 5'-γ-thiotriphosphate, and the like);
5'-phosphoramidates ((HO)$_2$(O)P—NH-5', (HO)(NH$_2$)(O)P—O-5);
5'-alkylphosphonates (e.g., RP(OH)(O)—O-5', (OH)$_2$(O)P-5'-CH$_2$, where R is alkyl (e.g., methyl, ethyl, isopropyl, propyl, or the like)); and
5'-alkyletherphosphonates (e.g., RP(OH)(O)—O-5', where R is alkylether (e.g., methoxymethyl, ethoxymethyl, or the like)).

In the nucleotide residue, the base is not particularly limited. The base may be a natural base or a non-natural base, for example. The base may be a naturally-derived base or a synthetic base, for example. As the base, a common (universal) base, a modified analog thereof, and the like can be used, for example.

Examples of the base include: purine bases such as adenine and guanine; and pyrimidine bases such as cytosine, uracil, and thymine. Other examples of the base include inosine, thymine, xanthine, hypoxanthine, nubularine, isoguanisine, and tubercidine. Examples of the base also include: alkyl derivatives such as 2-aminoadenine, 6-methylated purine, and 2-propylated purine; 5-halouracil and 5-halocytosine; 5-propynyl uracil and 5-propynyl cytosine; 6-azo uracil, 6-azo cytosine, and 6-azo thymine; 5-uracil (pseudouracil), 4-thiouracil, 5-halouracil, 5-(2-aminopropyl)uracil, 5-amino allyl uracil; 8-halogenated, aminated, thiolated, thioalkylated, hydroxylated, and other 8-substituted purines; 5-trifluoromethylated and other 5-substituted pyrimidines; 7-methylguanine; 5-substituted pyrimidines; 6-azapyrimidines; N-2, N-6, and O-6 substituted purines (including 2-aminopropyladenine); 5-propynyluracil and 5-propynylcytosine; dihydrouracil; 3-deaza-5-azacytosine; 2-aminopurine; 5-alkyluracil; 7-alkylguanine; 5-alkylcytosine; 7-deazaadenine; N6,N6-dimethyladenine; 2,6-diaminopurine; 5-amino-allyl-uracil; N3-methyluracil; substituted 1,2,4-triazoles; 2-pyridinone; 5-nitroindole; 3-nitropyrrole; 5-methoxyuracil; uracil-5-oxyacetic acid; 5-methoxycarbonylmethyluracil; 5-methyl-2-thiouracil; 5-methoxycarbonylmethyl-2-thiouracil; 5-methylaminomethyl-2-thiouracil; 3-(3-amino-3-carboxypropypuracil; 3-methylcytosine; 5-methylcytosine; N4-acetylcytosine; 2-thiocytosine; N6-methyladenine; N6-isopentyladenine; 2-methylthio-N-6-isopentenyladenine; N-methylguanine; and O-alkylated bases. Examples of the purines and pyrimidines include those disclosed in U.S. Pat. No. 3,687,808, "Concise Encyclopedia of Polymer Science and Engineering", pp. 858 to 859, edited by Kroschwitz J. I, John Wiley & Sons, 1990, and Englisch et al, Angewandte Chemie, International Edition, 1991, vol. 30, p. 613.

Other examples of the modified nucleotide residue include those having no base, i.e., those having an abasic ribophosphate backbone. Furthermore, as the modified nucleotide residue, those described in U.S. Provisional Application 60/465,665 (filing date: Apr. 25, 2003) and International Application No. PCT/US04/07070 (filing date: Mar. 8, 2004) can be used, for example, and these documents are incorporated herein by reference.

3. Synthesis Method of ssPN Molecule of the Present Invention

The method for synthesizing the ssPN molecule of the present invention is not particularly limited, and a conventionally known method can be employed. Examples of the method include synthesis methods according to genetic engineering procedures and chemical synthesis methods. Examples of the genetic engineering procedures include: synthesis methods utilizing in vitro transcription; methods using a vector; and methods carried out using a PCR cassette. The vector is not particularly limited, and examples thereof include non-virus vectors such as plasmid, and virus vectors. The above-described examples are merely illustrative, and the synthesis method is not limited thereto. The chemical synthesis methods are not particularly limited, and examples thereof include a phosphoramidite method and an H-phosphonate method. The chemical synthesis methods can be carried out using a commercially available automated nucleic acid synthesizer, for example. In the chemical synthesis methods, an amidite generally is used. The amidite is not particularly limited. Examples of commercially available amidites include RNA Phosphoramidites (2'-O-TBDMSi, trade name, Samchully Pharm. Co., Ltd.), ACE amidite, TOM amidite, CEE amidite, CEM amidite, and TEM amidite. In the synthesis of the ssPN molecule of the present invention, it is preferable to use the monomer of the present invention to be described below for the synthesis of the linker region(s) represented by the formula (I), for example.

5. Composition

The inhibitory composition according to the present invention is, as described above, a composition for inhibiting the expression of a target gene, containing the ssPN molecule of the present invention. The composition of the present invention is characterized in that it contains the ssPN molecule of the present invention, and other configurations are by no means limited. The inhibitory composition of the present invention also can be referred to as an inhibitory reagent, for example.

According to the present invention, for example, by administering the composition to a subject in which the target gene is present, it is possible to inhibit the expression of the target gene.

Furthermore, as described above, the pharmaceutical composition according to the present invention contains the ssPN molecule of the present invention. The pharmaceutical composition of the present invention is characterized in that it contains the ssPN molecule of the present invention, and other configurations are by no means limited. The pharmaceutical composition of the present invention also can be referred to as a pharmaceutical, for example.

According to the present invention, for example, by administering the pharmaceutical composition to a patient with a disease caused by a gene, it is possible to inhibit the expression of the gene, thereby treating the disease. In the present invention, the term "treatment" encompasses: prevention of diseases; improvement of diseases; and improvement in prognosis, for example, and it can mean any of them.

In the present invention, a disease to be treated is not particularly limited, and examples thereof include diseases caused by the expression of genes. Depending on the kind of the disease, a gene that causes the disease may be set as the target gene, and further, depending on the target gene, the expression inhibitory sequence may be set as appropriate.

A specific example is as follows. By setting the TGF-β1 gene as the target gene and incorporating an expression inhibitory sequence for this gene into the ssPN molecule, the ssPN molecule can be used for the treatment of inflammatory diseases, specifically, acute lung injury and the like, for example.

The method of using the inhibitory composition and the pharmaceutical composition according to the present invention (hereinafter, both the compositions simply are referred to as "the compositions") are not particularly limited, and examples thereof include administering the ssPN molecule to a subject having the target gene.

Examples of the subject to which the ssPN molecule of the present invention is administered include cells, tissues, and organs. Examples of the subject also include humans and nonhuman animals such as nonhuman mammals, i.e., mammals excluding humans. The administration may be performed in vivo or in vitro, for example. The cells are not particularly limited, and examples thereof include: various cultured cells such as HeLa cells, 293 cells, NIH3T3 cells, and COS cells; stem cells such as ES cells and hematopoietic stem cells; and cells isolated from living organisms, such as primary cultured cells.

The administration method is not particularly limited, and can be determined as appropriate depending on the subject, for example. When the subject is a cultured cell, the administration method may be a method using a transfection reagent, an electroporation method, or the like, for example. When the administration is performed in vivo, the administration may be either oral administration or parenteral administration, for example. Examples of the parenteral administration include injection, subcutaneous administration, and local administration.

Each of the compositions of the present invention may contain only the ssPN molecule of the present invention or further may contain an additive(s) in addition to the ssPN molecule, for example. The additive is not particularly limited, and preferably is a pharmaceutically acceptable additive, for example. The kind of the additive is not particularly limited, and can be selected as appropriate depending on the kind of the subject, for example.

In the composition of the present invention, the ssPN may form a complex with the additive, for example. The additive also can be referred to as a complexing agent, for example. The complex allows the ssPN molecule to be delivered efficiently, for example. The bond between the ssPN molecule and the complexing agent is not particularly limited, and examples thereof include noncovalent bond. The complex may be an inclusion complex or the like, for example.

The complexing agent is not particularly limited, and examples thereof include polymers, cyclodextrins, and adamantine. Examples of the cyclodextrins include linear cyclodextrin copolymers and linear oxidized cyclodextrin copolymers.

Other examples of the additive include a carrier, a binding substance that binds to a target cell, a condensing agent, and a fusogenic agent.

The carrier preferably is a polymer, more preferably a biopolymer, for example. Preferably, the carrier is biodegradable, for example. Examples of the carrier include: proteins such as human serum albumin (HSA), low-density lipoprotein (LDL), and globulin; carbohydrates such as, for example, dextran, pullulan, chitin, chitosan, inulin, cyclodextrin, and hyaluronic acid; and lipids. As the carrier, a synthetic polymer such as a synthetic polyamino acid also can be used, for example. Examples of the polyamino acid include polylysine (PLL), poly L-aspartic acid, poly L-glutamic acid, styrene-maleic anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymer, and polyphosphazine.

Examples of the binding substance include thyroid-stimulating hormone, melanocyte-stimulating hormone, lectin, glycoproteins, surfactant protein A, Mucin carbohydrate, multivalent lactose, multivalent galactose, N-acetyl-galactosamine, N-acetyl-gulucosamine, multivalent mannose, multivalent fucose, glycosylated polyamino acid, multivalent galactose, transferrin, bisphosphonate, polyglutamic acid, polyaspartic acid, lipids, cholesterol, steroids, bile acid, folate, vitamin B12, biotin, Neproxin, RGD peptide, and RGD peptide mimetic.

Examples of the fusogenic agent and the condensing agent include polyamino chains such as polyethyleneimine (PEI). PEI may be either linear or branched, and also, may be either synthetic or naturally occurring, for example. The PEI may be substituted with an alkyl or a lipid, for example. As the fusogenic agent, it is also possible to use polyhistidine, polyimidazole, polypyridine, polypropyleneimine, mellitin, a polyacetal substance (e.g., cationic polyacetal or the like), or the like, for example. The fusogenic agent may have an α-helix structure, for example. The fusogenic agent may be a membrane disruptive agent such as mellitin, for example.

As to the compositions according to the present invention, for example, the descriptions regarding the formation of the complex and the like in U.S. Pat. No. 6,509,323, U.S. Patent Publication No. 2003/0008818, PCT/US04/07070, and the like are incorporated herein by reference.

Other examples of the additive include amphiphilic molecules. The amphiphilic molecule is a molecule having a hydrophobic region and a hydrophilic region, for example. The molecule preferably is a polymer, for example. The polymer may have, for example, a secondary structure, preferably a repeating secondary structure. Specifically, polypeptide is preferable, and α-helix polypeptide and the like are more preferable, for example.

The amphiphilic polymer may be a polymer having two or more amphiphilic subunits, for example. Examples of the subunit include subunits with a cyclic structure having at least one hydrophilic group and one hydrophobic group. The subunit may contain steroid such as cholic acid, an aromatic structure, and the like, for example. The polymer may contain, for example, both a cyclic structure subunit, such as an aromatic subunit, and an amino acid.

5. Inhibitory Method

The inhibitory method according to the present invention is, as described above, a method for inhibiting the expression of a target gene, in which the ssPN molecule of the present invention is used. The inhibitory method of the present invention is characterized in that the ssPN molecule of the present invention is used therein, and other steps and conditions are by no means limited.

In the inhibitory method of the present invention, the mechanism by which the gene expression is inhibited is not particularly limited, and examples thereof include inhibition of the expression by RNA interference. The inhibitory method of the present invention is, for example, a method for inducing RNA interference that inhibits the expression of a target gene, and it also can be referred to an inhibitory method that is characterized in that the ssPN molecule of the present invention is used therein.

The inhibitory method of the present invention includes the step of administering the ssPN molecule to a subject in which the target gene is present, for example. By the administration step, the ssPN molecule is bought into contact with the subject to which the ssPN molecule is administered, for example. Examples of the subject include cells, tissues, and organs. Examples of the subject also include humans and nonhuman animals such as nonhuman mammals, i.e., mammals excluding humans. The administration may be performed in vivo or in vitro, for example.

In the inhibitory method of the present invention, the ssPN molecule may be administered alone, or the composition of the present invention containing the ssPN molecule may be administered, for example. The administration method is not particularly limited, and can be selected as appropriate depending on the kind of the subject, for example.

6. Treatment Method

As described above, the method for treating a disease according to the present invention includes the step of administering the ssPN molecule of the present invention to a patient, and the ssPN molecule includes, as the expression inhibitory sequence, a sequence that inhibits expression of a gene causing the disease. The treatment method of the present invention is characterized in that the ssPN molecule of the present invention is used therein, and other steps and conditions are by no means limited. The description regarding the inhibitory method of the present invention also applies to the treatment method of the present invention, for example.

7. Use of ssPN Molecule

The use according to the present invention is the use of the ssPN molecule of the present invention for inhibiting the expression of a target gene. Also, the use according to the present invention is the use of the ssPN molecule of the present invention for inducing RNA interference.

The nucleic acid molecule according to the present invention is a nucleic acid molecule for use in treatment of a disease. The nucleic acid molecule is the ssPN molecule of the present invention, and the ssPN molecule includes, as the expression inhibitory sequence, a sequence that inhibits expression of a gene causing the disease.

8. Monomer

The monomer according to the present invention is a monomer for nucleic acid synthesis, having the structure of the following formula (II). The description regarding the ssPN molecule of the present invention also applies to the monomer of the present invention, unless otherwise stated.

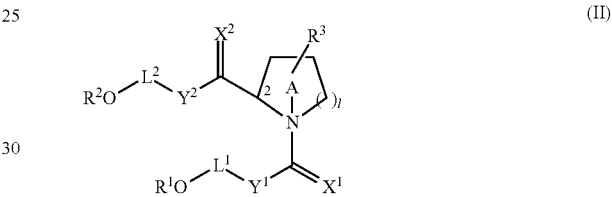

(II)

According to the monomer of the present invention, for example, in the synthesis of the ssPN molecule of the present invention, the linker regions (Lx) and (Ly) represented by the formula (I) can be synthesized easily. The monomer of the present invention can be used an amidite for automated nucleic acid synthesis, for example, and is applicable to general automated nucleic acid synthesizers, for example. Examples of the synthesis method include a phosphoramidite method and an H— phosphonate.

In the formula, $X^1$ and $X^2$ are each independently $H_2$, O, S, or NH;

$Y^1$ and $Y^2$ are each independently a single bond, $CH_2$, NH, O, or S;

$R^1$ and $R^2$ are each independently H, a protecting group, or a phosphate-protecting group;

$R^3$ is a hydrogen atom or substituent that is bound to C-3, C-4, C-5, or C-6 on a ring A;

$L^1$ is an alkylene chain composed of n atoms, and a hydrogen atom(s) on an alkylene carbon atom(s) may or may not be substituted with OH, $OR^a$, $NH_2$, $NHR^a$, $NR^aR^b$, SH, or $SR^a$, or, $L^1$ is a polyether chain obtained by substituting at least one carbon atom on the alkylene chain with an oxygen atom, provided that; when $Y^1$ is NH, O, or S, an atom bound to $Y^1$ in $L^1$ is carbon, an atom bound to $OR^1$ in $L^1$ is carbon, and oxygen atoms are not adjacent to each other;

$L^2$ is an alkylene chain composed of m atoms, and a hydrogen atom(s) on an alkylene carbon atom(s) may or may not be substituted with OH, OW, $NH_2$, $NHR^c$, $NR^cR^d$, SH, or $SR^c$, or $L^2$ is a polyether chain obtained by substituting at least one carbon atom on the alkylene chain with an oxygen atom, provided that: when $Y^2$ is NH, O, or S, an atom bound to $Y^2$ in $L^2$ is carbon, an atom bound to $OR^2$ in $L^2$ is carbon, and oxygen atoms are not adjacent to each other;

$R^a$, $R^b$, $R^c$, and $R^d$ are each independently a substituent or a protecting group;

l is 1 or 2;

m is an integer in the range from 0 to 30;

n is an integer in the range from 0 to 30;

on the ring A, one carbon atom other than C-2 may be substituted with nitrogen, oxygen, or sulfur; and the ring A may contain a carbon-carbon double bond or a carbon-nitrogen double bond.

As to the portions in common between the formula (II) and the formula (I), the descriptions stated above regarding the formula (I) also apply to the formula (II). Specifically, in the formula (II), as to $X^1$, $X^2$, $Y^1$, $Y^2$, $R^3$, $L^1$, $L^2$, l, m, n, and the ring A, for example, all the descriptions about them stated above regarding the formula (I) apply.

In the formula (II), $R^1$ and $R^2$ are each independently H, a protecting group, or a phosphate-protecting group, as described above.

The protecting group is as described above regarding the formula (I), for example. Specifically, the protecting group can be selected from Group I, for example. Group I includes, for example, a dimethoxytrityl (DMTr) group, a TBDMS group, an ACE group, a TOM group, a CEE group, a CEM group, a TEM group, and silyl-containing groups represented by the following formula. In particular, it is preferable that the protecting group is the DMtr group or any of the silyl-containing groups.

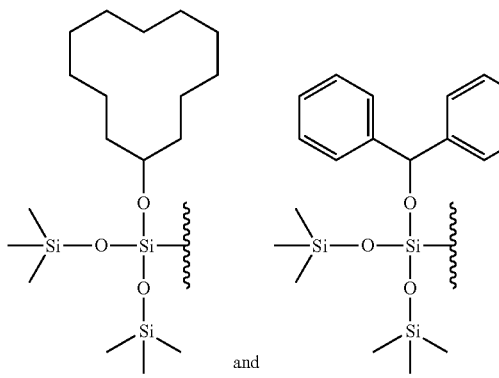

The phosphate-protecting group can be represented by the following formula, for example.

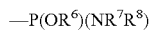

—P(OR$^6$)(NR$^7$R$^8$)

In the formula, $R^6$ is a hydrogen atom or any substituent. The substituent $R^6$ preferably is a hydrocarbon group, and the hydrocarbon group may or may not be substituted with an electron-withdrawing group, for example. Examples of the substituent $R^6$ include halogens, haloalkyls, heteroaryls, hydroxyalkyls, alkoxyalkyls, aminoalkyls, silyls, silyloxyalkyls, heterocyclylalkenyls, heterocyclylalkyls, heteroarylalkyls, and hydrocarbons such as alkyls, alkenyls, alkynyls, aryls, arylalkyls, cycloalkyls, cycloalkenyls, cycloalkylalkyls, and cyclylalkyls. Furthermore, the substituent $R^6$ may or may not be substituted with an electron-withdrawing group. Specific examples of the substituent $R^6$ include a β-cyanoethyl group, a nitrophenylethyl group, and a methyl group.

$R^7$ and $R^8$ are each a hydrogen atom or any substituent, and they may be the same or different. The substituents $R^7$ and $R^8$ preferably are each a hydrocarbon group, and the hydrocarbon group may or may not be substituted with any substituent.

Examples of the hydrocarbon group are the same as those listed in the above description regarding $R^6$, and the hydrocarbon group preferably is a methyl group, an ethyl group, or an isopropyl group. In this case, specific examples of —NR$^7$R$^8$ include a diisopropylamino group, a diethylamino group, and an ethylmethylamino group. Alternatively, the substituents $R^7$ and $R^8$ together (i.e., —NR$^7$R$^8$ as a whole) may form a nitrogen-containing ring (e.g., a piperidyl group, a morpholino group, or the like) with a nitrogen atom(s) to which they bind.

Specifically, the phosphate-protecting group can be selected from Group II described below. Group II includes —P(OCH$_2$CH$_2$CN)(N(i-Pr)$_2$) and —P(OCH$_3$)(N(i-Pr)$_2$), for example. In the above formulae, i-Pr indicates isopropyl.

In the formula (II), for example, one of $R^1$ and $R^2$ is H or a protecting group, and the other is H or a phosphate-protecting group. For example, it is preferable that, when $R^1$ is a protecting group, $R^2$ is H or a phosphate-protecting group. Specifically, it is preferable that, when $R^1$ is selected from Group I, $R^2$ is H or is selected from Group II. Also, it is preferable that, for example, when $R^1$ is a phosphate-protecting group, $R^2$ is H or a protecting group. Specifically, it is preferable that, when $R^1$ is selected from Group II, $R^2$ is H or is selected from Group I.

Examples of the structure of the formula (II) include the following formulae (II-1) to (II-9). In the following formulae, n and m are the same as in the formula (II). In the following formulae, q is an integer from 0 to 10.

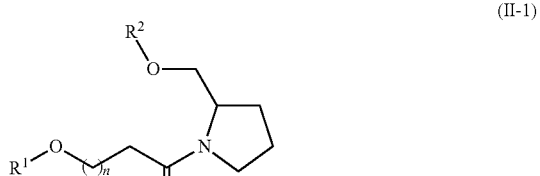

(II-1)

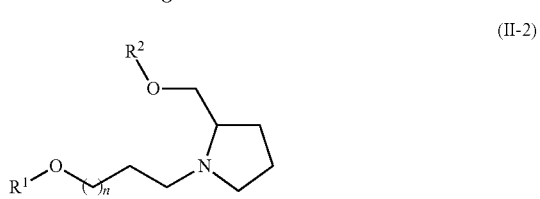

(II-2)

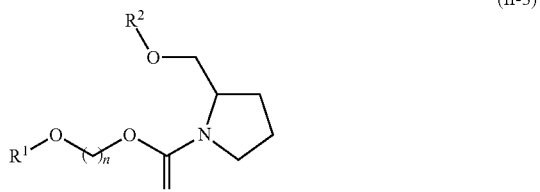

(II-3)

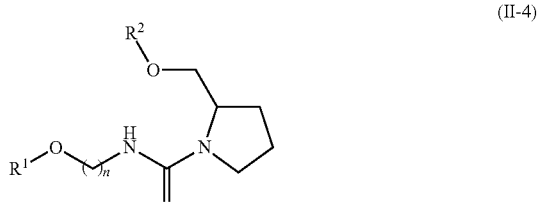

(II-4)

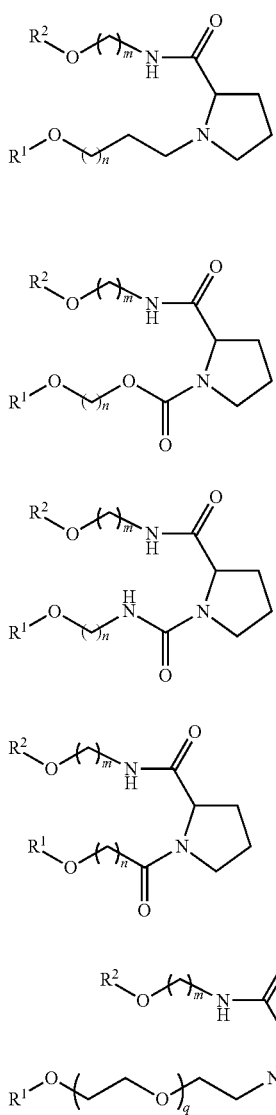

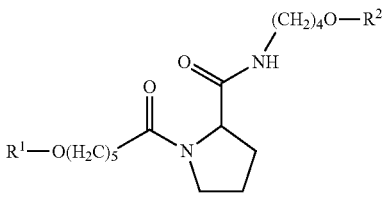

The monomer of the present invention preferably includes the above-described labeling substance, for example. It is particularly preferable that the monomer of the present invention includes the above-described stable isotope. The labeling substance is as described above.

When the monomer of the present invention includes an isotope such as the stable isotope, the isotope can be introduce to the ssPN molecule of the present invention easily, for example. The monomer including an isotope can be synthesized from, for example, a raw material having a pyrrolidine skeleton to which the isotope is introduced and a raw material having a piperidine skeleton to which the isotope is introduced. Examples of the raw material having a pyrrolidine skeleton include proline and prolinol.

The following schemes illustrate how the monomers of the present invention to which a stable isotope is introduced are synthesized using, as raw materials, proline and prolinol each having the stable isotope introduced thereto. The following schemes merely are illustrative, and the present invention is by no means limited thereto.

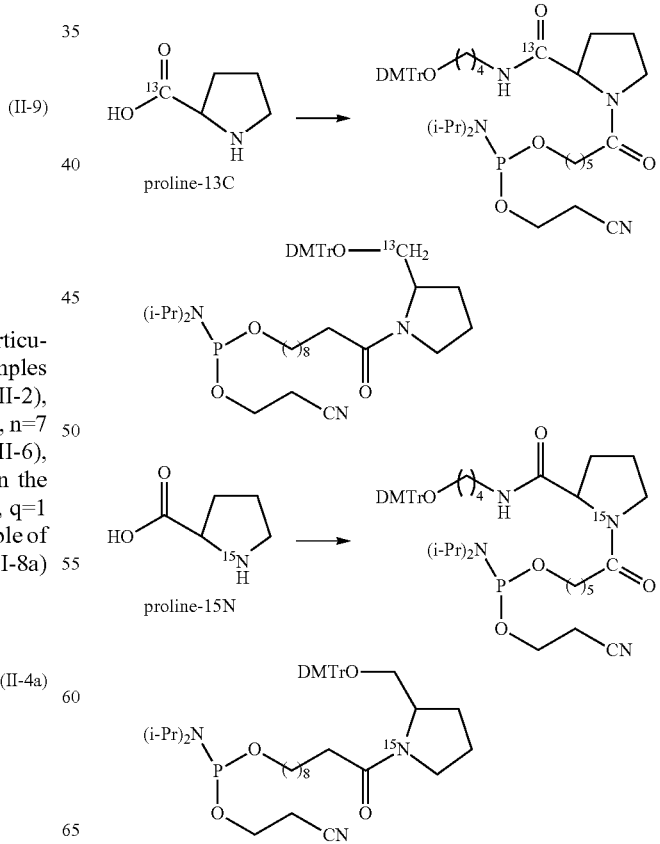

In the formulae (II-1) to (II-9), n, m, and q are not particularly limited, and are as described above. Specific examples are as follows: in the formula (II-1), n=8; in the formula (II-2), n=3; in the formula (II-3), n=4 or 8; in the formula (II-4), n=7 or 8; in the formula (II-5), n=3 and m=4; in the formula (II-6), n=8 and m=4; in the formula (II-7), n=8 and m=4; in the formula (II-8), n=5 and m=4; and in the formula (II-9), q=1 and m=4. The following formula (II-4a) shows an example of the formula (II-4) (n=8), and the following formula (II-8a) shows an example of the formula (I-8) (n=5, m=4).

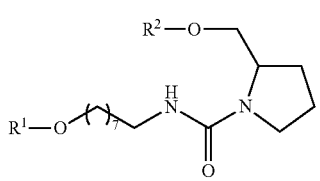

Prolinol having a heavy hydrogen (D) introduced thereto, which is an example of prolinol having a stable isotope introduced thereto, can be prepared by treating proline with LiAlD$_4$, as shown in the following scheme, for example.

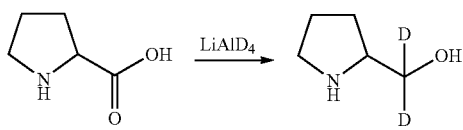

Proline having a heavy oxygen ($^{18}$O) introduced thereto, which is an example of proline having a stable isotope introduced thereto, can be prepared by reacting proline methyl ester with H$_2$$^{18}$O under a basic condition, as shown in the following scheme, for example.

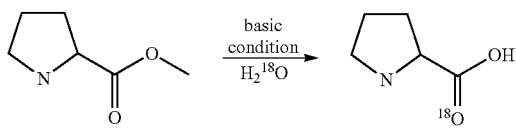

Heavy nitrogen ($^{15}$N)-introduced proline (proline-15N) and heavy nitrogen ($^{15}$N)-introduced prolinol (prolinol-15N) can be synthesized according to the following scheme, for example. Specifically, first, furan or tetrahydrofuran is caused to react with $^{15}$NH$_3$ to prepare heavy nitrogen ($^{15}$N)-introduced pyrrole. This is then formylated, thus obtaining heavy nitrogen ($^{15}$N)-introduced 2-formylpyrrole. Proline-15N can be synthesized by oxidizing this to a carboxylic acid and then reducing the pyrrole moiety. Also, by reducing the heavy nitrogen ($^{15}$N)-introduced 2-formylpyrrole, prolinol-15N can be synthesized.

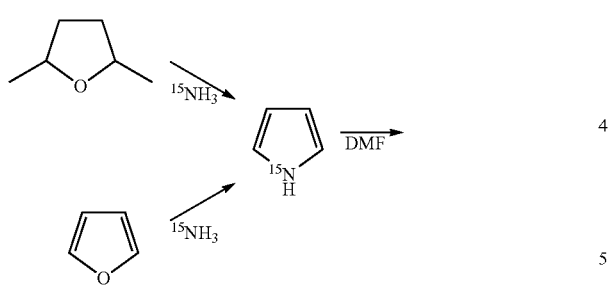

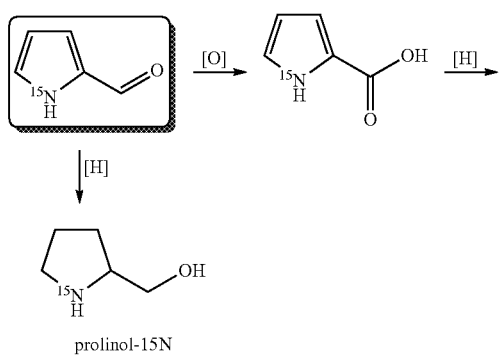

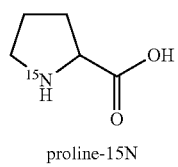

proline-15N

The heavy carbon ($^{13}$C)-introduced proline (proline-13C) and heavy carbon ($^{13}$C)-introduced prolinol (prolinol-13C) can be synthesized according to the following scheme, for example. That is, first, pyrrole is formylated with heavy carbon ($^{13}$C)-introduced DMF (DMF-13C), thus obtaining heavy carbon ($^{13}$O-introduced 2-formylpyrrole. Proline-13C can be synthesized by oxidizing this to a carboxylic acid and then reducing the pyrrole moiety. Also, by reducing the heavy carbon ($^{13}$C)-introduced 2-formylpyrrole, prolinol-13C can be synthesized.

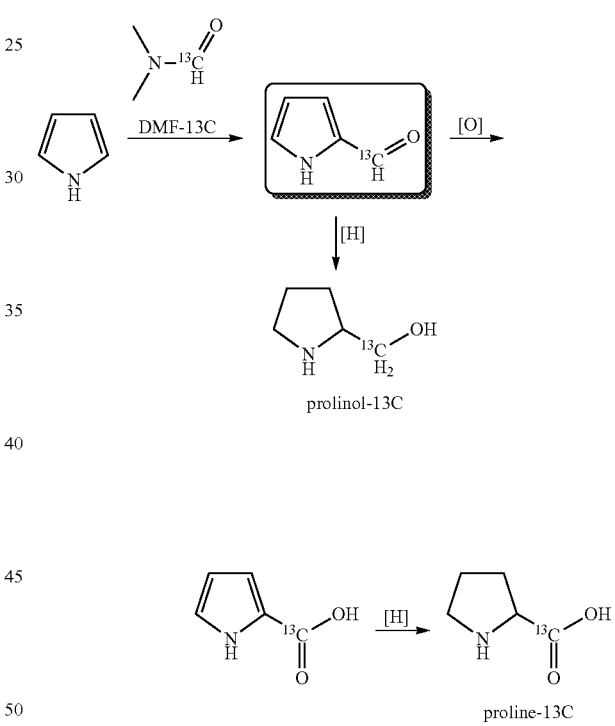

A monomer having a stable isotope introduced thereto can be synthesized in the above-described manner. By using the monomer as amidite for nucleic acid synthesis, a nucleic acid molecule in which a stable isotope is introduced to the linker region can be synthesized.

In the following, the present invention will be described in detail with reference to examples and the like. It is to be noted, however, that the present invention is by no means limited thereto.

EXAMPLES

Example A1

1. Synthesis of Prolinol

According to Scheme 1 shown below, prolinol protected with a dimethoxytrityl group was synthesized.

Scheme 1

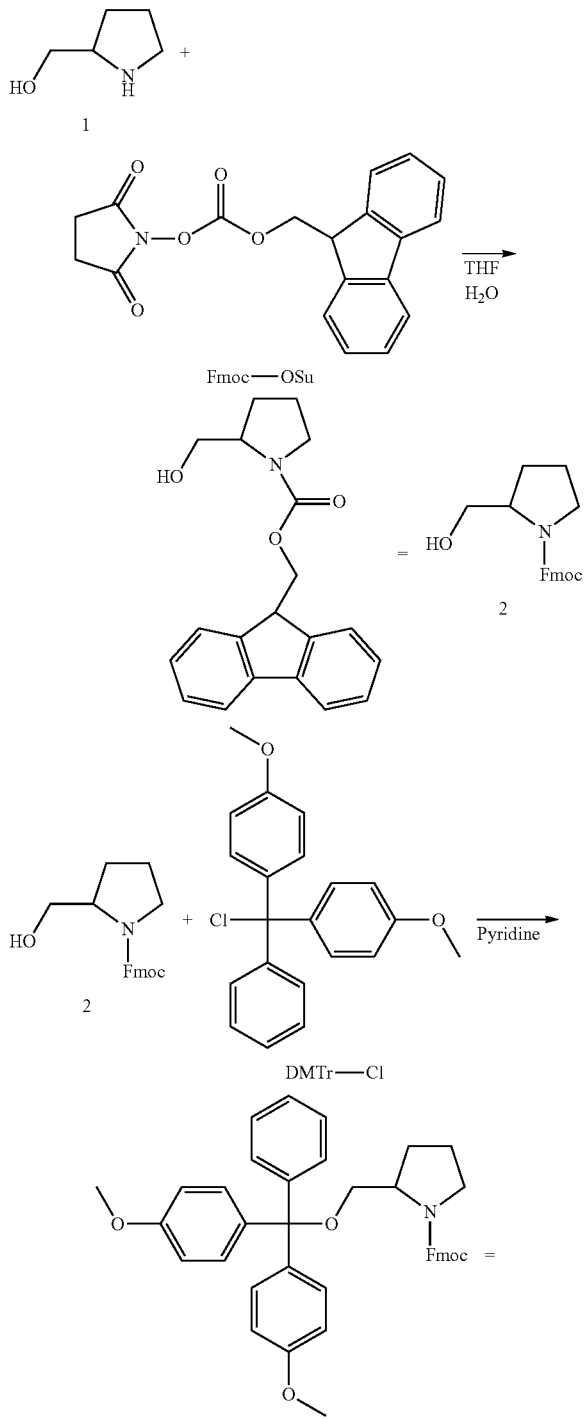

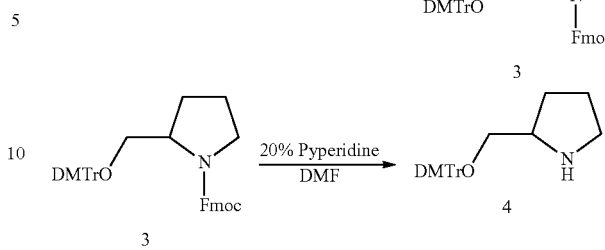

(1) Fmoc-L-prolinol (Compound 2)

L-prolinol (Compound 1) (0.61 g, 6.0 mmol) was dissolved in 70 ml of pure water, thus preparing an L-prolinol aqueous solution. N-(9-Fluorenylmethoxycarbonyloxy)succinimide (Fmoc-OSu) (2.0 g, 6.0 mmol) was dissolved in 10 ml of THF. This THF solution was added to the L-prolinol aqueous solution, and this was stirred for 1 hour so as to react the L-prolinol and the Fmoc-OSu. The reaction solution was separated into a liquid fraction and a precipitate fraction. These fractions respectively were subjected to extraction with ethyl acetate, and organic layers respectively were collected therefrom. The thus-obtained organic layers were mixed together, and anhydrous sodium sulfate was added thereto to absorb moisture (hereinafter, this process is referred to as a "drying" process). The organic layers were filtered, and the filtrate obtained was vacuum concentrated. The residual substance obtained was purified by silica gel column chromatography (the eluent hexane:ethyl acetate=1:1). Thus, Compound 2 was obtained (1.4 g, yield: 74%). The result of NMR analysis with respect to this compound is shown below.

$^1$H-NMR (CDCl$_3$): δ7.77 (2H, d, J=7.7 Hz, Ar—H), 7.60 (2H, d, J=7.3 Hz, Ar—H), 7.40 (2H, t, J=7.5 Hz, Ar—H), 7.31 (2H, t, J=7.6 Hz, Ar—H), 4.40-4.50 (2H, m, COOCH$_2$), 4.22 (1H, t, J=6.5 Hz, Ar—CH), 3.20-3.80 (5H, m, H-5, H-6), 1.75 (3H, m, H-3, H-4), 1.40 (1H, m, H-3).

(2) Fmoc-DMTr-L-Prolinol (Compound 3)

The Fmoc-L-prolinol (Compound 2) (1.4 g, 4.3 mmol) was dissolved in 20 ml of pyridine and azeotroped three times. The residual substance obtained was dissolved in 20 ml of pyridine. While stirring this solution in an ice bath under argon, 4,4'-dimethoxytrityl chloride (DMTr-Cl) (1.8 g, 5.3 mmol) was added thereto. The reaction in this reaction solution was followed by TLC using chloroform/methanol, and the reaction was allowed to proceed for 4 hours until a spot of the Fmoc-L-prolinol no longer was observed. In order to quench excess DMTr-Cl, 3 ml of methanol was added to the reaction solution, and this was stirred for 10 minutes. Chloroform was further added to the reaction solution, and thereafter, an organic layer was collected. The collected organic layer was washed with saturated saline, then with a 5% aqueous solution of sodium hydrogencarbonate, and again with saturated saline. The organic layer thus washed was dried with anhydrous sodium sulfate. The organic layer then was filtered, and the filtrate obtained was vacuum concentrated. The residual substance obtained was purified by silica gel column chromatography (the eluent: chloroform, 1% pyridine). Thus, Compound 3 was obtained (2.0 g, yield: 74%). The result of NMR analysis with respect to this compound is shown below.

$^1$H-NMR (CDCl$_3$): δ7.77 (2H, d, J=7.7 Hz, Ar—H), 7.60 (2H, d, J=7.3 Hz, Ar—H), 7.40-7.18 (13H, m, Ar—H), 6.89

(4H, d, J=8.6 Hz, Ar—H), 4.20-4.40 (2H, m, COOCH₂), 4.02 (1H, t, J=6.5 Hz, Ar—CH), 3.80-3.10 (5H, m, H-5, H-6), 3.73 (s, 6H, OCH₃), 1.84 (3H, m, H-3, H-4), 1.58 (1H, m, H-3).

3-(3-dimethylaminopropyl)carbodiimide hydrochloride is referred to as "EDC", and N,N-dimethylaminopyridine (4-dimethylaminopyridine) is referred to as "DMAP".

Scheme 2

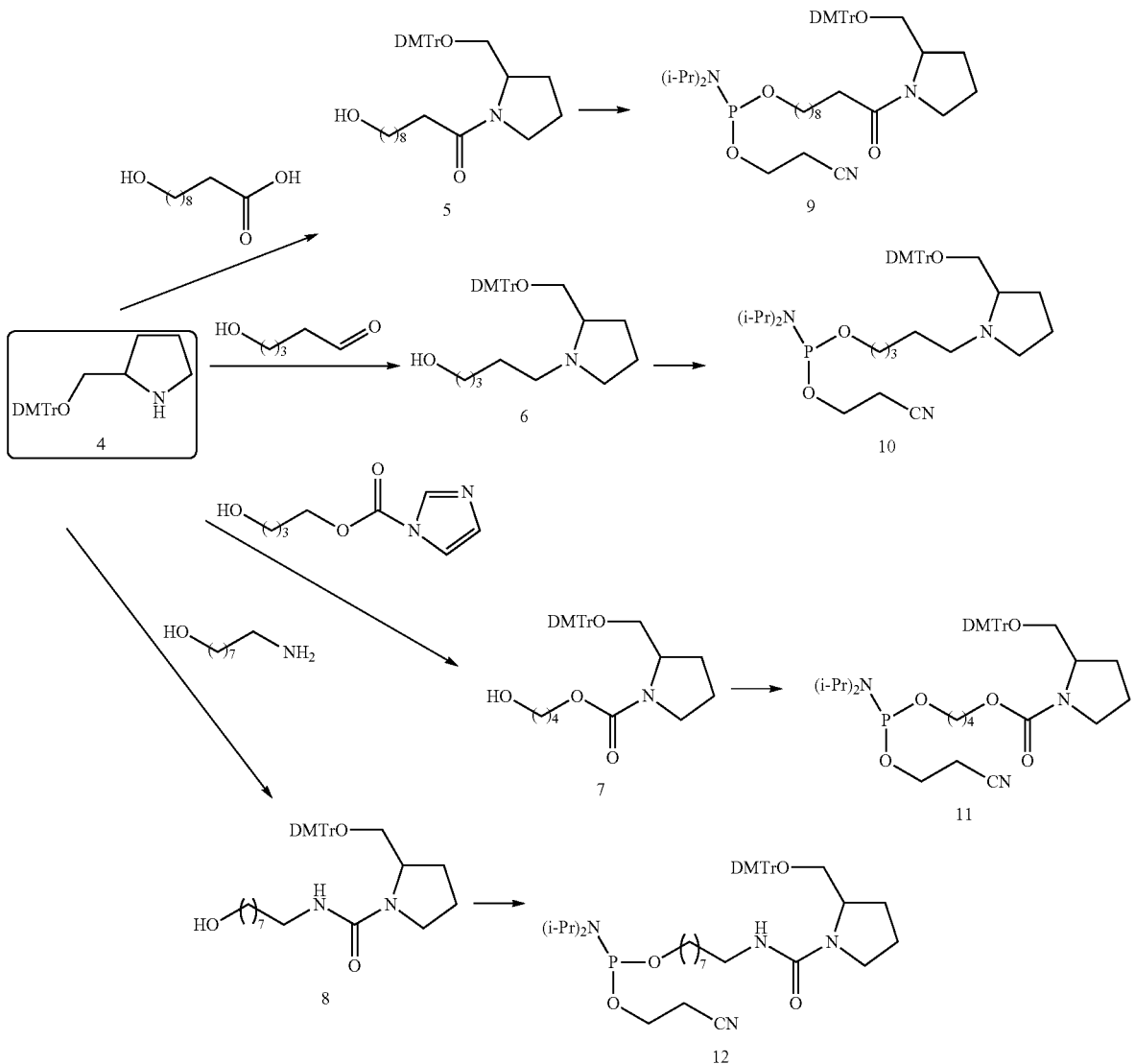

(3) DMTr-L-Prolinol (Compound 4)

The Fmoc-DMTr-L-prolinol (Compound 3) (2.0 g, 3.2 mmol) was dissolved in 25 ml of a DMF solution containing 20% piperidine, and this was stirred for 12 hours. The solution was vacuum concentrated, and the residual substance obtained was purified by silica gel column chromatography (chloroform:methanol=85:15, containing 1% pyridine). Thus, Compound 4 was obtained (1.0 g, yield: 78%). The result of NMR analysis with respect to this compound is shown below.

¹H-NMR (CDCl₃) δ7.40-7.14 (9H, m, Ar—H), 6.82 (4H, d, J=8.6 Hz, Ar—H), 3.78 (6H, s, OCH₃), 3.31 (1H, m, H-6), 3.07 (2H, m, H-2, H-6), 2.90 (2H, m, H-5), 1.84 (3H, m, H-3, H-4), 1.40 (1H, m, H-3).

2. Synthesis of Amidite Derivatives

Next, according to Scheme 2 shown below, amidite derivatives having prolinol were synthesized. Hereinafter, 1-ethyl- (1) DMTr-Amide-L-Prolinol (Compound 5)

The DMTr-L-prolinol (Compound 4) (0.80 g, 2.0 mmol), EDC (0.46 g, 2.4 mmol), and DMAP (0.29 g, 2.4 mmol) were dissolved in 20 ml of dichloromethane, and this then was stirred. 10-hydroxydecanoic acid (0.45 g, 2.4 mmol) was added to this solution, and this then was stirred. The reaction in this reaction solution was followed by TLC using ethyl acetate, and the reaction was allowed to proceed for 20 hours until a spot of the DMTr-L-prolinol no longer was observed. Then, dichloromethane was added to the reaction solution, and an organic layer then was collected. The collected organic layer was washed with saturated saline, and then dried with anhydrous sodium sulfate. The organic layer was filtered, and the filtrate obtained was vacuum concentrated. The residual substance was purified by silica gel column chromatography (ethyl acetate, containing 1% pyridine). Thus, Compound 5 was obtained (0.71 g, yield: 62%). The result of NMR analysis with respect to this compound is shown below.

$^1$H-NMR (CDCl$_3$): δ7.40-7.14 (9H, m, Ar—H), 6.82 (4H, d, J=8.6 Hz, Ar—H), 3.78 (6H, s, OCH$_3$), 3.68-2.93 (7H, m, H-2, H-5, H-6), 2.27-1.72 (6H, m, alkyl, H-3, H-4), 1.58 (4H, s, alkyl), 1.30 (10H, s, alkyl).

(2) DMTr-Alkyl-L-Prolinol (Compound 6)

The DMTr-L-prolinol (Compound 4) (0.80 g, 2.0 mmol) was dissolved in 15 ml of methanol. 5-hydroxypentanal (0.31 g, 3.0 mmol) was added thereto, and this then was stirred. Sodium cyanoborohydride (0.25 g, 4.0 mmol) was added to this solution, and this was further stirred. The reaction in this reaction solution was followed by TLC using ethyl acetate/hexane, and the reaction was allowed to proceed for 24 hours until a spot of the DMTr-L-prolinol no longer was observed. Ethyl acetate was added to the reaction solution, and an organic layer was collected. The collected organic layer was washed with saturated saline, and then dried with anhydrous sodium sulfate. The organic layer was filtered, and the filtrate obtained was vacuum concentrated. The residual substance was purified by silica gel column chromatography (hexane:ethyl acetate=1:1, containing 1% pyridine). Thus, Compound 6 was obtained (0.62 g, yield: 63%). The result of NMR analysis with respect to this compound is shown below.

$^1$H-NMR (CDCl$_3$): δ7.40-7.14 (9H, m, Ar—H), 6.82 (4H, d, J=8.6 Hz, Ar—H), 3.78 (6H, s, OCH$_3$), 3.70-2.86 (4H, m, CH$_2$OH, H-6), 2.06-1.79 (5E1, m, alkyl, H-2, H-5), 1.74-1.49 (6H, m, alkyl, H-3, H-4), 1.45-1.27 (4H, m, alkyl).

(3) DMTr-Urethane-L-Prolinol (Compound 7)

1,4-butane diol (0.90 g, 10 mmol) was dissolved in 30 ml of dichloromethane. Carbonyldiimidazole (1.4 g, 8.6 mmol) was further added thereto, and this was stirred for 3 hours. An organic layer of this reaction solution was washed with saturated saline, and then dried with anhydrous sodium sulfate. The organic layer was filtered, and the filtrate obtained was vacuum concentrated. The residual substance was purified by silica gel column chromatography (chloroform:methanol=9:1). Thus, a compound in which one end of 1,4-butane diol was activated with carbonyldiimidazole was obtained (0.25 g, 1.5 mmol). This compound was dissolved in 15 ml of dichloromethane. The DMTr-L-prolinol (Compound 4) (0.6 g, 1.5 mmol) was added thereto, and this was stirred for 24 hours. Ethyl acetate further was added to this mixture, and an organic layer was collected. The collected organic layer was washed with saturated saline, and then dried with anhydrous sodium sulfate. The organic layer was filtered, and the filtrate obtained was vacuum concentrated. The residual substance was purified by silica gel column chromatography (hexane:ethyl acetate=1:1, containing 1% pyridine). Thus, Compound 7 was obtained (0.61 g, yield: 77%). The result of NMR analysis with respect to this compound is shown below.

$^1$H-NMR (CDCl$_3$): δ7.40-7.14 (9H, m, Ar—H), 6.82 (4H, d, J=8.6 Hz, Ar—H), 4.24-3.94 (2H, m, COOCH$_2$), 3.78 (s, 6H, OCH$_3$), 3.72-2.96 (7H, m, alkyl, H-2, H-5, H-6), 2.10-1.30 (8H, m, alkyl, H-3, H-4).

(4) DMTr-Ureido-L-Prolinol (Compound 8)

The DMTr-L-prolinol (Compound 4) (0.50 g, 1.2 mmol) and triphosgene (0.12 g, 0.40 mmol) were dissolved in 8 ml of dichloromethane, and the resultant mixture was stirred in an ice bath under argon. N, N-diisopropylethylamine (0.31 g, 2.4 mmol) was added to the solution, and this was stirred for 1 hour. Then, 8-amino-1-octanol (0.17 g, 1.2 mmol) was further added thereto, and this was stirred for 30 minutes in an ice bath in the same manner as in the above. Then, this was further stirred at room temperature for 20 hours. Dichloromethane was added to the solution, and an organic layer was collected. The collected organic layer was washed with saturated saline, and then dried with anhydrous sodium sulfate. The organic layer was filtered, and the filtrate obtained was vacuum concentrated. The residual substance was purified by silica gel column chromatography (hexane:ethyl acetate=4:1, containing 1% triethylamine). Thus, Compound 8 was obtained (0.44 g, yield: 62%). The result of NMR analysis with respect to this compound is shown below.

$^1$H-NMR (CDCl$_3$): δ7.40-7.14 (9H, m, Ar—H), 6.82 (4H, m, Ar—H), 3.78 (s, 6H, OCH$_3$), 3.68-3.25 (9H, m, CH$_2$NH, CH$_2$OH, H-2, H-5, H-6), 1.74-1.18 (16H, m, alkyl, H-3, H-4).

(5) Amidite Derivatives Having Prolinol (Compounds 9 to 12)

Compounds 9 to 12 were synthesized in the following manner using the modified prolinols (Compounds 5 to 8), respectively, as raw materials. Each of the modified prolinols and 5-benzylthio-1H-tetrazole were dissolved in 3 ml of acetonitrile. The amount of the modified prolinol used was as follows: Compound 5: 0.69 g (1.2 mmol); Compound 6: 0.60 g (1.2 mmol); Compound 7: 0.60 g (1.2 mmol); and Compound 8: 0.25 g (0.43 mmol). The amount of the 5-benzylthio-1H-tetrazole used was: 0.15 g (0.78 mmol) for Compounds 5 to 7; and 54 mg (0.15 mmol) for Compound 8. Under argon, 2-cyanoethyl N,N, N',N'-tetraisopropyl phosphorodiamidite was added to the solution, and this was stirred for 2 hours. The amount of the 2-cyanoethyl N,N, N',N'-tetraisopropyl phosphorodiamidite added was: 0.54 g (1.8 mmol) in systems using Compounds 5 to 7; and 0.19 g (0.64 mmol) in a system using Compound 8. Then, a saturated aqueous solution of sodium hydrogencarbonate was added to the solution, and an organic layer was extracted with dichloromethane and collected. The collected organic layer was dried with anhydrous sodium sulfate. The organic layer was filtered, and the filtrate obtained was vacuum concentrated. The residual substance was purified by silica gel column chromatography (hexane:ethyl acetate=1: 1, containing 1% triethylamine). Thus, Compounds 9 to 12 were obtained. The results of NMR analysis with respect to these compounds are shown below.

DMTr-amide-L-prolinol amidite (Compound 9, 0.60 g, yield: 55%) $^1$H-NMR (CDCl$_3$): δ7.40-7.14 (9H, m, Ar—H), 6.82 (H-1, d, J=8.6 Hz, Ar—H), 3.78 (6H, s, OCH$_3$), 3.68-2.93 (11H, m, CH$_2$O, POCH$_2$, CHCH$_3$, H-2, H-5, H-6), 2.58 (2H, m, CH$_2$CN), 2.27-1.72 (6H, m, alkyl, H-3, H-4), 1.58 (H-1, s, alkyl), 1.30 (22H, s, alkyl, CHCH$_3$).

DMTr-alkyl-L-prolinol amidite (Compound 10, 0.71 g, yield: 60%) $^1$H-NMR (CDCl$_3$): δ7.40-7.14 (9H, m, Ar—H), 6.82 (4H, d, J=8.6 Hz, Ar—H), 3.78 (6H, s, OCH$_3$), 3.70-2.86 (H-1, m, CH$_2$O, POCH$_2$, CHCH$_3$, H-6), 2.58 (2H, m, CH$_2$CN), 2.06-1.79 (5H, m, alkyl, H-2, H-5), 1.74-1.49 (H-1, m, alkyl, H-3, H-4), 1.37-1.10 (16H, m, alkyl, CHCH$_3$).

DMTr-urethane-L-prolinol amidite (Compound 11, 0.67 g, yield: 52%) $^1$H-NMR (CDCl$_3$): δ7.40-7.14 (9H, m, Ar—H), 6.82 (4H, d, J=8.6 Hz, Ar—H), 4.24-3.94 (2H, m, COOCH$_2$), 3.78 (s, 6H, OCH$_3$), 3.72-2.96 (11H, m, CH$_2$O, POCH$_2$, CHCH$_3$, H-2, H-5, H-6), 2.58 (21-1, m, CH$_2$CN), 2.10-1.46 (8H, m, alkyl, H-3, H-4), 1.34-1.10 (12H, m, CHCH$_3$).

DMTr-ureido-L-prolinol amidite (Compound 12, 0.20 g, yield: 61%) $^1$H-NMR (CDCl$_3$): δ7.40-7.14 (9H, m, Ar—H), 6.82 (4H, m, Ar—H), 3.78 (s, 6H, OCH$_3$), 3.65-3.25 (13H, m, CH$_2$O, POCH$_2$, CHCH$_3$, H-2, CH$_2$NH, CH$_2$OH, H-2, H-5, H-6), 2.73 (2H, m, CH$_2$CN), 2.10-1.48 (16H, m, alkyl, H-3, H-4), 1.35-1.10 (12H, m, CHCH$_3$).

Example A2
Next, according to Scheme 3 shown below, amidite derivatives having L-proline were synthesized.
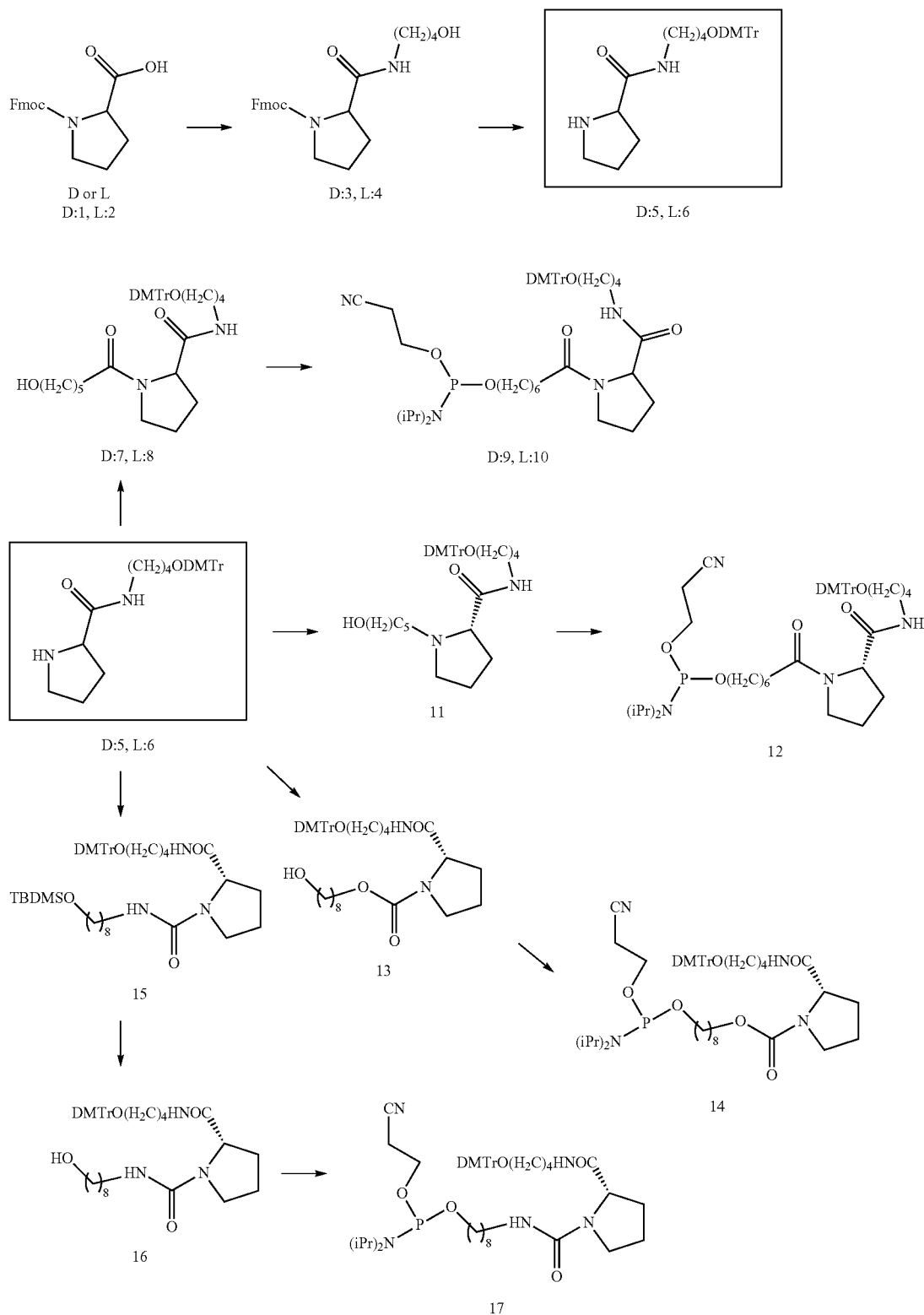

(1) DMTr-Hydroxy Amide Amino-L-Proline (Compound 11)

An acetic acid buffer (7 ml) was added to an ethanol solution (7 ml) containing DMTr-amide-L-proline (Compound 6) (1.00 g, 2.05 mmol) and 5-hydroxypentanal (0.33 g, 3.07 mmol) under ice-cooling. The resultant mixture was stirred for 20 minutes under ice-cooling. Thereafter, sodium cyanoborohydride (0.77 g, 12.28 mmol) was further added thereto, and this was stirred for 7 hours at room temperature. The mixture was diluted with dichloromethane, washed with water, and then further washed with saturated saline. Then, the organic layer was collected and dried with sodium sulfate. The organic layer was filtered, and the solvent in the resultant filtrate was removed by evaporation under reduced pressure. The residual substance obtained was applied to silica gel column chromatography (the eluent $CH_2Cl_2:CH_3OH=98:2$, containing 0.05% pyridine). Then, the product obtained was applied to silica gel column chromatography (the eluent: $CH_2Cl_2:CH_3OH=98:2$, containing 0.05% pyridine), and the product obtained was further subjected to silica gel column chromatography (the eluent: dichloromethane: acetone=7:3, containing 0.05% pyridine). Thus, Compound 11 in the form of colorless syrup was obtained (0.49 g, yield: 41%). Ms (FAB+): m/z 575 ($M^+$), 303 ($DMTr^+$)

(2) DMTr-Amide Amino-L-Proline Amidite (Compound 12)

The thus-obtained DMTr-hydroxy amide amino-L-proline (Compound 11) (0.50 g, 0.87 mmol) was mixed with anhydrous acetonitrile, and the mixture was azeotropically dried at room temperature. To the residual substance obtained, diisopropylammonium tetrazolide (178 mg, 1.04 mmol) was added. The resultant mixture was deaerated under reduced pressure and filled with argon gas. Anhydrous acetonitrile (1 ml) was added to the mixture, and an anhydrous acetonitrile solution (1 ml) of 2-cyanoethoxy-N,N, N',N'-tetraisopropyl phosphorodiamidite (313 mg, 1.04 mmol) was further added thereto. This mixture was stirred for 4 hours at room temperature in an argon atmosphere. Then, the mixture was diluted with dichloromethane, and this was washed with saturated sodium bicarbonate water and then with saturated saline. An organic layer was collected and dried with sodium sulfate. Thereafter, the organic layer was filtered. The solvent in the filtrate obtained was removed by evaporation under reduced pressure. The residual substance obtained was applied to column chromatography using amino silica as a filler (the eluent: hexane:acetone=7:3, containing 0.05% pyridine). Thus, Compound 12 in the form of colorless syrup was obtained (0.57 g, purity: 93%, yield: 79%). The purity was measured by HPLC (hereinafter the same). The result of NMR analysis with respect to this compound is shown below.

$^1$H-NMR ($CDCl_3$): δ7.41-7.43 (m, 2H, Ar—H), 7.28-7.32 (m, 4H, Ar—H), 7.25-7.27 (m, 2H, Ar—H), 7.18-7.21 (m, 1H, Ar—H), 6.80-6.84 (m, 4H, Ar—H), 3.73-3.84 (m, 1H), 3.79 (s, 6H, $OCH_3$), 3.47-3.64 (m, 3H), 3.12-3.26 (m, 2H), 3.05 (t, J=6.4 Hz, 2H, $CH_2$), 2.98-2.02 (m, 2H), 2.61 (t, J=5.8 Hz, 2H, $CH_2$), 2.55-2.63 (m, 2H), 2.27-2.42 (m, 1H, CH), 2.31 (t, 7.8 Hz, 2H, $CH_2$), 2.03-2.19 (m, 1H, CH), 1.40-1.90 (m, 8H), 1.23-1.33 (m, 5H), 1.14-1.20 (m, 12H, $CH_3$);

P-NMR ($CDCl_3$): 6146.91;

Ms (FAB+): m/z 774 ($M^+$), 303 ($DMTr^+$), 201 ($C_8H_{19}N_2OP^+$).

(3) DMTr-Hydroxy Amide Carbamoyl-L-Proline (Compound 13)

To an anhydrous acetonitrile solution (10 ml) in which the DMTr-amide-L-proline (Compound 6) (1.00 g, 2.05 mmol) had been dissolved, an anhydrous acetonitrile solution (20 ml) in which 1-imidazolylcarbonyloxy-8-hydroxyoctane (1.12 g, 4.92 mmol) has been dissolved was added at room temperature in an argon atmosphere. This mixture was heated at 40° C. to 50° C. for 2 days, and then was allowed to stand at room temperature for 5 days. The solvent in the mixture was removed by evaporation under reduced pressure. The residual substance obtained was applied to silica gel column chromatography (the eluent: dichloromethane: acetone=4:1, containing 0.05% pyridine). Thus, Compound 13 in the form of colorless syrup was obtained (0.68 g, yield: 50%). The result of NMR analysis with respect to this compound is shown below.

$^1$H-NMR ($CDCl_3$): δ7.40-7.42 (m, 2H, Ar—H), 7.27-7.31 (m, 6H, Ar—H), 7.17-7.21 (m, 1H, Ar—H), 6.79-6.82 (m, 4H, Ar—H), 4.23-4.30 (m, 1H), 4.05-4.10 (m, 2H), 3.79 (s, 6H, $OCH_3$), 3.60-3.65 (m, 2H), 3.32-3.55 (m, 2H), 3.16-3.29 (m, 2H), 3.01-3.07 (m, 2H), 2.38-2.40 (m, 1H, CH), 1.83-1.90 (m, 2H), 1.57-1.69 (m, 8H), 1.26-1.36 (m, 2H);

Ms (FAB+): m/z 602 ($M^+$), 303 ($DMTr^+$).

(4) DMTr-Amide Carbamoyl-L-Proline Amidite (Compound 14)

The thus-obtained DMTr-hydroxy amide carbamoyl-L-proline (Compound 13) (0.63 g, 1.00 mmol) was mixed with anhydrous pyridine, and the resultant mixture was azeotropically dried at room temperature. Diisopropylammonium tetrazolide (206 mg, 1.20 mmol) was added to the residual substance obtained, and the resultant mixture was deaerated under reduced pressure and filled with argon gas. Anhydrous acetonitrile (1 ml) was added to the mixture, and an anhydrous acetonitrile solution (1 ml) of 2-cyanoethoxy-N,N, N',N'-tetraisopropyl phosphorodiamidite (282 mg, 1.12 mmol) was further added thereto. This mixture was stirred for 4 hours at room temperature in an argon atmosphere. Then, the mixture was diluted with dichloromethane, and this was washed with saturated sodium bicarbonate water and then with saturated saline. An organic layer was collected and dried with sodium sulfate. Thereafter, the organic layer was filtered. The solvent in the filtrate obtained was removed by evaporation under reduced pressure. The residual substance obtained was applied to column chromatography using amino silica as a filler (the eluent hexane: acetone=7:3, containing 0.5% pyridine). Thus, Compound 14 in the form of colorless syrup was obtained (0.74 g, purity: 100%, yield: 87%). The result of NMR analysis with respect to this compound is shown below.

P-NMR ($CDCl_3$): δ147.19;

Ms (FAB+): m/z 860 ($M^+$), 303 ($DMTr^+$), 201 ($C_8H_9N_2OP^+$).

(5) DMTr-T-Butyl Dimethyl Siloxy Amide Ureido-L-Proline (Compound 15)

An anhydrous tetrahydrofuran solution (10 ml) was added to triphosgene (1.22 g, 4.10 mmol) under ice-cooling in an argon atmosphere. An anhydrous tetrahydrofuran solution (10 ml) in which DMTr-amide-L-proline (Compound 6) (1.00 g, 2.05 mmol) and DIEA (9.80 g, 75.8 mmol) had been dissolved was instilled in this mixture under ice-cooling in an argon atmosphere for 30 minutes. Thereafter, this was stirred for 1 hour at room temperature. An anhydrous tetrahydrofuran solution (20 ml) in which 10-amino-1-t-butyl dimethyl siloxy decane (2.66 g, 10.25 mmol) and DIEA (3.20 g, 24.76 mmol) had been dissolved was instilled in the mixture under ice-cooling in an argon atmosphere for 45 minutes. Then, the mixture was stirred overnight at room temperature in an argon atmosphere. This mixture was diluted with ethyl acetate (200 ml), and an organic layer was collected. The organic layer was washed with saturated sodium bicarbonate water and then further washed with saturated saline. Then, the organic layer was collected and dried with sodium sulfate. The organic layer was filtered, and the solvent in the filtrate obtained was removed by evaporation under reduced pressure. The residual substance obtained was applied to silica gel column chromatography (the eluent: dichloromethane: acetone=4:1, containing 0.05% pyridine). Thus, Compound 15 in the form of colorless syrup was obtained (0.87 g, yield: 55%).

(6) DMTr-Hydroxy Amide Ureido-L-Proline Compound (16)

To the thus-obtained DMTr-t-butyl dimethyl siloxy amide ureido-L-proline (15) (0.87 g, 1.12 mmol), an anhydrous tetrahydrofuran dichloromethane solution (10 ml) was added at room temperature in an argon atmosphere. To the mixture, a 1 mol/l tetrabutylammonium fluoride-containing tetrahydrofuran solution (4.69 ml, Tokyo Chemical Industry Co., Ltd.) was added, and this was stirred for 3 days at room temperature in an argon atmosphere. The mixture was diluted with dichloromethane (150 ml), and this was washed with water and then further washed with saturated saline. An organic layer was collected and dried with sodium sulfate. Thereafter, the organic layer was filtered. The solvent in the filtrate obtained was removed by evaporation under reduced pressure. The residual substance obtained was applied to silica gel column chromatography (the eluent: dichloromethane:acetone=1:1, containing 0.05% pyridine). Thus, Compound 16 in the form of colorless syrup was obtained (0.68 g, yield: 92%). The result of NMR analysis with respect to this compound is shown below.

$^1$H-NMR (CDCl$_3$): δ7.41-7.43 (m, 2H, Ar—H), 7.27-7.31 (m, 4H, Ar—H), 7.19-7.26 (m, 2H, Ar—H), 7.19-7.21 (m, 1H, Ar—H), 6.80-6.83 (m, 4H, Ar—H), 4.34 (t, 2H, CH$_2$), 3.79 (s, 6H, OCH$_3$), 3.63 (d, 1H, J=6.4 Hz, CH$_2$), 3.61 (d, 1H, J=6.4 Hz, CH$_2$), 3.34-3.37 (m, 1H, CH), 3.16-3.27 (m, 5H), 3.04 (t, J=5.9 Hz, 2H, CH$_2$), 2.38-2.45 (m, 1H, CH), 1.83-2.05 (m, 3H), 1.45-1.64 (m, 8H), 1.25-1.38 (m, 7H).

(7) DMTr-Amide Ureido-L-Proline Amidite (Compound 17)

The thus-obtained DMTr-hydroxy amide ureido-L-proline (Compound 16) (0.62 g, 0.94 mmol) was mixed with anhydrous acetonitrile, and the resultant mixture was azeotropically dried at room temperature. Diisopropylammonium tetrazolide (192 mg, 1.12 mmol) was added to the residual substance obtained, and the resultant mixture was deaerated under reduced pressure and filled with argon gas. Anhydrous acetonitrile (1 ml) was added to the mixture, and an anhydrous acetonitrile solution (1 ml) of 2-cyanoethoxy-N,N,N',N'-tetraisopropyl phosphorodiamidite (282 mg, 1.12 mmol) was further added thereto. This was stirred for 4 hours at room temperature in an argon atmosphere. Then, the mixture was diluted with dichloromethane, and this was washed with saturated sodium bicarbonate water and then with saturated saline. An organic layer was collected and dried with sodium sulfate. Thereafter, the organic layer was filtered. The solvent in the filtrate obtained was removed by evaporation under reduced pressure. The residual substance obtained was applied to column chromatography using amino silica as a filler (the eluent hexane:acetone=1:1, containing 0.05% pyridine). Thus, Compound 17 in the form of colorless syrup was obtained (0.77 g, purity: 88%, yield: 84%). The result of NMR analysis with respect to this compound is shown below.

P-NMR (CDCl$_3$): δ147.27;

Ms (FAB+): m/z 860 (M$^+$+1), 303 (DMTr$^+$), 201 (C$_8$H$_{19}$N$_2$OP$^+$).

Example A3

Synthesis of Proline-Diamide-Amidite

In order to produce a nucleic acid molecule of the present invention including a linker having a proline skeleton, L-proline-diamide-amidite and D-proline-diamide-amidite were synthesized according to Scheme 3.

(A3-1) L-Proline-Diamide-Amidite (1) Fmoc-Hydroxy Amide-L-Proline (Compound 4)

Compound 2 (Fmoc-L-proline) in Scheme 3 was used as a starting material. Compound 2 (10.00 g, 29.64 mmol), 4-amino-1-butanol (3.18 g, 35.56 mmol), and 1-hydroxybenzotriazole (10.90 g, 70.72 mmol) were mixed together. The mixture was deaerated under reduced pressure and filled with argon gas. Anhydrous acetonitrile (140 ml) was added to the mixture at room temperature, and an anhydrous acetonitrile solution (70 ml) of dicyclohexylcarbodiimide (7.34 g, 35.56 mmol) was further added thereto. Thereafter, this was stirred for 15 hours at room temperature in an argon atmosphere. After the completion of the reaction, the generated precipitate was removed by filtration, and the solvent in the collected filtrate was removed by evaporation under reduced pressure. Dichloromethane (200 ml) was added to the residual substance obtained, and the mixture was washed with saturated sodium bicarbonate water (200 ml). Then, an organic layer was collected and dried with magnesium sulfate. Thereafter, the organic layer was filtered, and the solvent in the filtrate obtained was removed by evaporation under reduced pressure. Diethyl ether (200 ml) was added to the residual substance, thereby turning the residual substance to powder. The thus-obtained powder was collected by filtration. Thus, Compound 4 in the form of colorless powder was obtained (10.34 g, yield: 84%). The result of NMR analysis with respect to this compound is shown below.

$^1$H-NMR (CDCl$_3$): δ7.76-7.83 (m, 2H, Ar—H), 7.50-7.63 (m, 2H, Ar—H), 7.38-7.43 (m, 2H, Ar—H), 7.28-7.33 (m, 2H, Ar—H), 4.40-4.46 (m, 1H, CH), 4.15-4.31 (m, 2H, CH$_2$), 3.67-3.73 (m, 2H, CH$_2$), 3.35-3.52 (m, 2H, CH$_2$), 3.18-3.30 (m, 2H, CH$_2$), 2.20-2.50 (m, 4H), 1.81-2.03 (m, 3H), 1.47-1.54 (m, 2H);

Ms (FAB+): m/z 409 (M+H$^+$).

(2) DMTr-Amide-L-Proline (Compound 6)

Fmoc-hydroxy amide-L-proline (Compound 4) (7.80 g, 19.09 mmol) was mixed with anhydrous pyridine (5 ml), and the resultant mixture was azeotropically dried twice at room temperature. To the residual substance obtained, 4,4'-dimethoxytrityl chloride (8.20 g, 24.20 mmol), DMAP (23 mg, 0.19 mmol), and anhydrous pyridine (39 ml) were added. This mixture was stirred for 1 hour at room temperature. Thereafter, methanol (7.8 ml) was added thereto, and this was stirred for 30 minutes at room temperature. This mixture was diluted with dichloromethane (100 ml), and washed with saturated sodium bicarbonate water (150 ml). Thereafter, an organic layer was separated. The organic layer was dried with sodium sulfate, and then filtered. The solvent in the filtrate obtained was removed by evaporation under reduced pressure. Anhydrous dimethylformamide (39 ml) and piperidine (18.7 ml, 189 mmol) were added to the thus-obtained unpurified residual substance, and this was stirred for 1 hour at room temperature. After the completion of the reaction, the solvent in the mixture was removed by evaporation under reduced pressure at room temperature. The residual substance obtained was applied to silica gel column chromatography (trade name: Wakogel C-300, the eluent: CH$_2$Cl$_2$ CH$_3$OH=9:1, containing 0.05% pyridine). Thus, Compound 6 in the form of light yellow oil was obtained (9.11 g, yield: 98%). The result of NMR analysis with respect to this compound is shown below.

$^1$H-NMR (CDCl$_3$): δ7.39-7.43 (m, 21-1, Ar—H), 7.30 (d, J=8.8 Hz, 4H, Ar—H), 7, 21 (tt, 1H, 4.9, 1.3 Hz, Ar—H), 6.81 (d, J=8.8 Hz, 4H, Ar—H), 3.78 (s, 6H, OCH$_3$), 3.71 (dd, H, J=6.3 Hz, 5.4 Hz, CH), 3.21 (2H, 12.9, 6.3 Hz, 2H, CH$_2$), 3.05

(t, J=6.3 Hz, 2H, CH$_2$), 2.85-2.91 (m, 2H, CH$_2$), 2.08-2.17 (m, 1H, CH), 1.85-2.00 (m, 3H), 1.55-1.65 (m, 5H):

Ms (FAB+); m/z 489 (M+H$^+$), 303 (DMTr$^+$).

(3) DMTr-Hydroxy Diamide-L-Proline (Compound 8)

An anhydrous dichloromethane solution was prepared by mixing the thus-obtained DMTr-amide-L-proline (Compound 6) (6.01 g, 12.28 mmol), EDC (2.83 g, 14.74 mmol), 1-hydroxybenzotriazole (3.98 g, 29.47 mmol), and triethylamine (4.47 g, 44.21 mmol) in anhydrous dichloromethane (120 ml). 6-hydroxyhexanoic acid (1.95 g, 14.47 mmol) was further added to this solution at room temperature in an argon atmosphere, and this then was stirred for 1 hour at room temperature in an argon atmosphere. The mixture was diluted with dichloromethane (600 ml), and this was washed three times with saturated saline (800 ml). An organic layer then was collected. The organic layer was dried with sodium sulfate, and then filtered. The solvent in the filtrate obtained was removed by evaporation under reduced pressure. Thus, Compound 8 in the form of light yellow foam was obtained (6.29 g, yield: 85%). The result of NMR analysis with respect to this compound is shown below.

$^1$H-NMR (CDCl$_3$): δ7.41-7.43 (m, 2H, Ar—H), 7.27-7.31 (m, 4H, Ar—H), 7.19-7.26 (m, 2H, Ar—H), 7.17-7.21 (m, 1H, Ar—H), 6.79-6.82 (m, 4H, Ar—H), 4.51-4.53 (m, 1H, CH), 3.79 (s, 6H, OCH$_3$), 3.61 (t, 2H, J=6.4 Hz, CH$_2$), 3.50-3.55 (m, 1H, CH), 3.36-3.43 (m, 1H, CH), 3.15-3.24 (m, 2H, CH$_2$), 3.04 (t, J=6.3 Hz, 2H, CH$_2$), 2.38-2.45 (m, 1H, CH), 2.31 (t, 6.8 Hz, 2H, CH$_2$), 2.05-2.20 (m, 1H, CH), 1.92-2.00 (m, 1H, CH), 1.75-1.83 (m, 1H, CH), 1.48-1.71 (m, 8H), 1.35-1.44 (m, 2H, CH$_2$);

Ms (FAB+): m/z 602 (Mt), 303 (DMTr$^+$).

(4) DMTr-Diamide-L-Proline Amidite (Compound 10)

The thus-obtained DMTr-hydroxy diamide-L-proline (Compound 8) (8.55 g, 14.18 mmol) was mixed with anhydrous acetonitrile, and the resultant mixture was azeotropically dried three times at room temperature. To the residual substance obtained, diisopropylammonium tetrazolide (2.91 g, 17.02 mmol) was added. The resultant mixture was deaerated under reduced pressure and filled with argon gas. Anhydrous acetonitrile (10 ml) was added to the mixture, and an anhydrous acetonitrile solution (7 ml) of 2-cyanoethoxy-N, N, N',N'-tetraisopropyl phosphorodiamidite (5.13 g, 17.02 mmol) was further added thereto. This mixture was stirred for 2 hours at room temperature in an argon atmosphere. Then, the mixture was diluted with dichloromethane, and this was washed with saturated sodium bicarbonate water (200 ml) three times and then with saturated saline (200 ml). An organic layer was collected and dried with sodium sulfate. Thereafter, the organic layer was filtered. The solvent in the filtrate obtained was removed by evaporation under reduced pressure. The residual substance obtained was applied to column chromatography using amino silica gel as a filler (the eluent: hexane:ethyl acetate=1:3, containing 0.05% pyridine). Thus, Compound 10 in the form of colorless syrup was obtained (10.25 g, purity: 92%, yield: 83%). The result of NMR analysis with respect to this compound is shown below.

$^1$H-NMR (CDCl$_3$): δ7.40-7.42 (m, 2H, Ar—H), 7.29-7.31 (m, 4H, Ar—H), 7.25-7.27 (m, 2H, Ar—H), 7.17-7.21 (m, 1H, Ar—H), 6.80-6.82 (m, 4H, Ar—H), 4.51-4.53 (m, 1H, CH), 3.75-3.93 (m, 4H), 3.79 (s, 6H, OCH$_3$), 3.45-3.60 (m, 4H), 3.35-3.45 (m, 1H, CH), 3.20-3.29 (m, 1H, CH), 3.04 (t, J=6.4 Hz, 2H, CH$_2$), 2.62 (t, J=5.8 Hz, 2H, CH$_2$), 2.40-2.44 (m, 1H, CH), 2.31 (t, 7.8 Hz, 2H, CH$_2$), 2.03-2.19 (m, 1H, CH), 1.92-2.02 (m, 1H, CH), 1.70-1.83 (m, 1H, CH), 1.51-1.71 (m, 8H), 1.35-1.44 (m, 2H, CH$_2$), 1.18 (d, J=6.8 Hz, 6H, CH$_3$), 1.16 (d, J=6.8 Hz, 6H, CH$_3$);

P-NMR (CDCl$_3$): Msδ147.17;

Ms (FAB+): m/z 802 (M$^+$), 303 (DMTr$^+$), 201 (C$_8$H$_{19}$N$_2$OP$^+$.

(A3-2) D-Proline-Diamide-Amiclite (1) Fmoc-hydroxy amide-D-proline (Compound 3)

Compound 1 (Fmoc-D-proline) in Scheme 3 was used as a starting material. The mixture of Compound 1 (1.5 g, 4.45 mmol), dicyclohexylcarbodiimide (1.1 g, 5.34 mmol), and 1-hydroxybenzotriazole (1.5 g, 10.69 mmol) was deaerated under reduced pressure and filled with argon gas. Anhydrous acetonitrile (24 ml) was added to the mixture at room temperature, and an anhydrous acetonitrile solution (6 ml) of 4-amino-1-butanol (0.48 g, 5.34 mmol) was further added thereto. Thereafter, this was stirred for 15 hours at room temperature in an argon atmosphere. After the completion of the reaction, the generated precipitate was removed by filtration, and the solvent in the collected filtrate was removed by evaporation under reduced pressure. Dichloromethane was added to the residual substance obtained, and the mixture was washed with acetic acid buffer (pH4.0) three times and further washed with saturated sodium bicarbonate water three times. Then, an organic layer was collected and dried with magnesium sulfate. Thereafter, the organic layer was filtered, and the solvent in the filtrate obtained was removed by evaporation under reduced pressure. Diethyl ether (50 ml) was added to the residual substance, thereby turning the residual substance to powder. The thus-obtained powder was collected by filtration. Thus, Compound 3 in the form of white powder was obtained. The result of NMR analysis with respect to this compound is shown below.

$^1$H-NMR (400 MHz, CDCl$_3$): δ7.77 (d, J=7.3 Hz, 2H); 7.58 (br, 2H); 7.41 (t, J=7.3 Hz, 2H); 7.32 (t, J=7.3 Hz, 2H); 4.25-4.43 (m, 4H); 3.25-3.61 (m, 6H); 1.57-1.92 (m, 8H).

MS (FAB+): m/z 409 (M+H$^+$).

(2) DMTr-Amide-D-Proline (Compound 5)

Fmoc-hydroxy amide-D-proline (Compound 3) (1.0 g, 2.45 mmol) was mixed with anhydrous pyridine (5 ml), and the resultant mixture was azeotropically dried twice at room temperature. To the residual substance obtained, 4,4'-dimethoxytrityl chloride (1.05 g, 3.10 mmol), DMAP (3 mg, 0.024 mmol), and anhydrous pyridine (5 ml) were added. This mixture was stirred for 1 hour at room temperature. Thereafter, methanol (1 ml) was added thereto, and this was stirred for 30 minutes at room temperature. This mixture was diluted with dichloromethane, and this was washed with saturated sodium bicarbonate water. Thereafter, an organic layer was separated. The organic layer was dried with sodium sulfate, and then filtered. The solvent in the filtrate obtained was removed by evaporation under reduced pressure. Anhydrous dimethylformamide (5 ml) and piperidine (2.4 ml, 24 mmol) were added to the thus-obtained unpurified residual substance, and this was stirred for 1 hour at room temperature. After the completion of the reaction, the solvent in the mixture was removed by evaporation under reduced pressure at room temperature. The residual substance obtained was applied to silica gel column chromatography (trade name Wakogel C-300, the eluent CH$_2$Cl$_2$: CH$_3$OH=9:1, containing 0.05% pyridine). Thus, Compound 5 in the form of light yellow oil was obtained (1.26 g, yield: 96%). The result of NMR analysis with respect to this compound is shown below.

$^1$H-NMR (400 MHz, CDCl$_3$): δ7.62 (br, 1H); 7.41-7.44 (m, 2H); 7.26-7.33 (m, 6H); 7.17-7.22 (m, 1H); 6.80-6.84 (m, 4H); 3.78 (s, 6H); 3.71 (dd, J=8.8, 5.4 Hz, 1H); 3.22 (q, 6.5 Hz, 2H); 3.07 (t, J=6.1 Hz, 2H); 2.97-3.03 (m, 1H); 2.85-2.91 (m, 1H); 1.85-2.15 (m, 3H); 1.55-1.73 (m, 6H).

MS (FAB+): m/z 489 (M+H$^+$), 303 (DMTr$^+$).

(3) DMTr-Hydroxy Diamide-D-Proline (Compound 7)

An anhydrous dichloromethane solution was prepared by mixing the thus-obtained DMTramide-D-proline (Compound 5) (1.2 g, 2.45 mmol), EDC (566 mg, 2.95 mmol), 1-hydroxybenzotriazole (796 mg, 5.89 mmol), and triethylamine (1.2 ml, 8.84 mmol) in anhydrous dichloromethane (24 ml). 6-hydroxyhexanoic acid (390 mg, 2.95 mmol) was further added to this solution at room temperature in an argon atmosphere, and this then was stirred for 1 hour at room temperature in an argon atmosphere. The mixture was diluted with dichloromethane, and this was washed with saturated sodium bicarbonate water three times. An organic layer was collected and dried with sodium sulfate. Thereafter, the organic layer was filtered. The solvent in the filtrate obtained was removed by evaporation under reduced pressure. Thus, Compound 7 in the form of light yellow oil was obtained (1.4 g, yield: 95%). The result of NMR analysis with respect to this compound is shown below.

$^1$H-NMR (400 MHz, CDCl$_3$): δ7.40-7.43 (m, 2H); 7.25-7.32 (m, 6H); 7.17-7.22 (m, 1H); 6.79-6.83 (m, 4H); 3.79 (s, 6H); 3.58-3.63 (m, 2H); 3.49-3.55 (m, 1H); 3.15-3.26 (m, 2H); 3.02-3.07 (m, 2H); 2.30-2.33 (m, 2H); 2.11-2.20 (m, 1H); 1.50-1.99 (m, 13H); 1.36-1.43 (m, 2H);

MS (FAB$^+$): m/z 602 (Mt), 303 (DMTr$^+$).

(4) DMTr-Diamide-D-Proline Amidite (Compound 9)

The thus-obtained DMTr-hydroxy diamide-D-proline (Compound 7) (1.2 g, 1.99 mmol) was mixed with anhydrous acetonitrile, and the resultant mixture was azeotropically dried three times at room temperature. Diisopropylammonium tetrazolide (410 mg, 2.40 mmol) was added to the residual substance obtained. The resultant mixture was deaerated under reduced pressure and filled with argon gas. Anhydrous acetonitrile (2.4 ml) was added to the mixture, and 2-cyanoethoxy-N,N, N',N'-tetraisopropyl phosphorodiamidite (722 mg, 2.40 mmol) was further added thereto. This mixture was stirred for 2 hours at room temperature in an argon atmosphere. Then, the mixture was diluted with dichloromethane, and this was washed with saturated sodium bicarbonate water three times and then washed with saturated saline. An organic layer was collected and dried with sodium sulfate. Thereafter, the organic layer was filtered. The solvent in the filtrate obtained was removed by evaporation under reduced pressure. The residual substance obtained was applied to column chromatography using amino silica gel as a filler (the eluent: hexane:ethyl acetate=1:3). Thus, Compound 9 in the form of colorless oil was obtained (1.4 g, purity: 95%, yield: 83%). The result of NMR analysis with respect to this compound is shown below.

$^1$H-NMR (400 MHz, CDCl$_3$): δ7.40-7.43 (m, 2H); 7.25-7.32 (m, 6H); 7.14-7.21 (m, 1H); 6.80-6.83 (m, 4H); 3.80-3.85 (m, 2H); 3.79 (s, 6H); 3.49-3.65 (m, 5H); 3.02-3.06 (m, 2H); 2.60-2.63 (m, 2H); 2.29-2.33 (m, 2H); 1.77-1.82 (m, 2H); 1.56-1.68 (m, 8H); 1.38-1.43 (m, 2H); 1.15-1.29 (m, 18H);

$^{31}$P-NMR (162 MHz, CDCl$_3$): 8146.94;

MS (FAB+): m/z 802 (M$^+$), 303 (DMTr$^+$), 201 (C$_8$H$_{19}$N$_2$OP$^+$).

Example A4

In order to produce a nucleic acid molecule of the present invention including a linker having a proline skeleton, L-proline-diamide-amidite (type B) was synthesized according to Scheme 4 shown below.

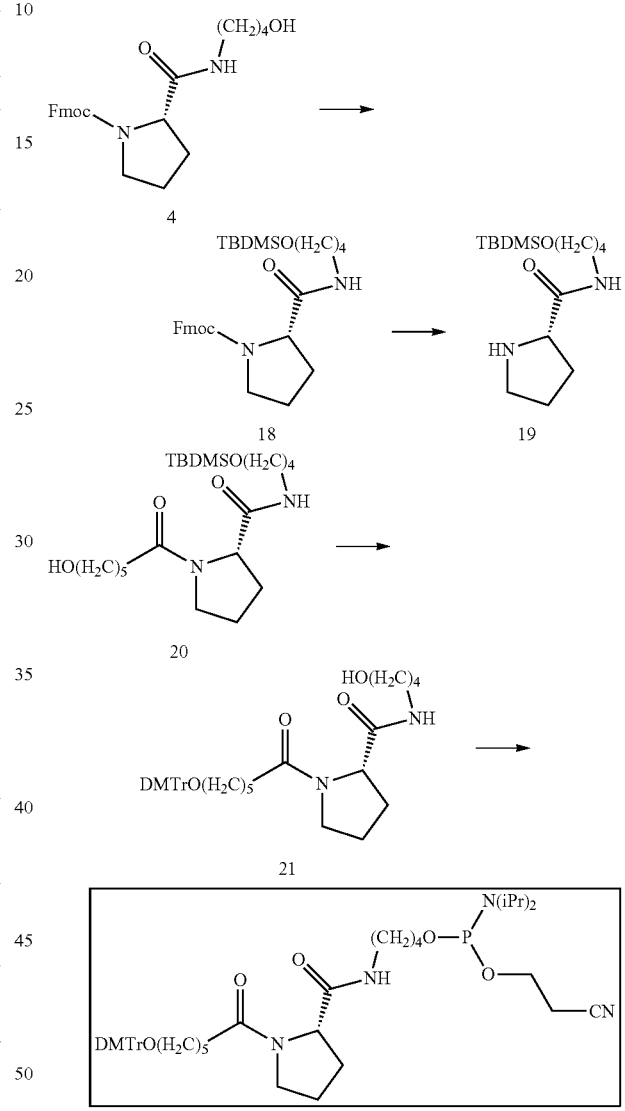

Scheme 4

Fmoc: 9-fluorenylmethyloxycarbonyl
TBDMS: tert-butyldimethylsilyl
DMTr: 4,4'-dimethoxytrityl

(1) Fmoc-T-Butyl-Dimethyl Siloxy Amide-L-Proline (Compound 18)

Fmoc-hydroxy amide-L-proline (Compound 4) (2.00 g, 30 mmol), t-butyl-dimethyl silyl chloride (1.11 g, 35 mmol), and imidazole (10.90 g, 71 mmol) were mixed together. The mixture was deaerated under reduced pressure and filled with argon gas. Anhydrous acetonitrile (20 ml) was added to the mixture at room temperature, and this was stirred overnight at room temperature in an argon atmosphere. After the completion of the reaction, dichloromethane (150 ml) was added to the mixture. The resultant mixture was washed with water three times and then with saturated saline. An organic layer was collected and dried with magnesium sulfate. Thereafter, the organic layer was filtered. The solvent in the filtrate obtained was removed by evaporation under reduced pressure, and the residual substance was applied to silica gel column chromatography (the eluent: $CH_2Cl_2$:$CH_3OH$=95:5). Thus, Compound 18 in the form of colorless syrup was obtained (2.35 g, yield: 92%). The result of NMR analysis with respect to this compound is shown below.

$^1$H-NMR (CDCl$_3$): δ7.76-7.78 (m, 2H, Ar—H), 7.50-7.63 (m, 2H, Ar—H), 7.38-7.42 (m, 2H, Ar—H), 7.29-7.34 (m, 2H, Ar—H), 4.10-4.46 (m, 4H, CH$_2$), 3.47-3.59 (m, 4H, CH$_2$), 3.20-3.26 (m, 2H, CH), 1.85-1.95 (m, 2H), 1.42-1.55 (m, 6H), 0.96 (s, 9H, t-Bu), 0.02 (s, 6H, SiCH$_3$);

Ms (FAB+): m/z 523 (M+H$^+$), (2) t-Butyl-Dimethyl Siloxy Amide-L-Proline (Compound 19)

To the thus-obtained Fmoc-t-butyl-dimethyl siloxy amide-L-proline (Compound 18) (1.18 g, 2.5 mmol), anhydrous acetonitrile (5 ml) and piperidine (2.4 ml) were added, and this was stirred for 1 hour at room temperature. After the completion of the reaction, acetonitrile (50 ml) was added to the mixture, and insoluble matters were removed by filtration. The solvent in the filtrate obtained was removed by evaporation under reduced pressure. The residual substance obtained was applied to silica gel column chromatography (the eluent: $CH_2Cl_2$: $CH_3OH$=9:1). Thus, Compound 19 in the form of colorless syrup was obtained (0.61 g, yield: 90%). The result of NMR analysis with respect to this compound is shown below.

$^1$H-NMR (CDCl$_3$): δ3.71 (dd, 1H, J=9.0 Hz, 5.2 Hz, CH), 3.61-3.64 (m, 2H, CH$_2$), 3.22-3.28 (m, 2H, CH$_2$), 2.98-3.04 (m, 1H, CH), 2.86-2.91 (m, 1H, CH), 2.08-2.17 (m, 1H, CH), 1.86-1.93 (m, 1H, CH), 1.66-1.75 (m, 2H, CH$_2$), 1.52-1.57 (m, 4H), 0.89 (s, 9-H, t-Bu), 0.05 (s, 6H, SiCH$_3$);

Ms (FAB+); m/z 301 (M+H$^+$).

(3) t-Butyl-Dimethyl Siloxy Amide Hydroxy Amide-L-Proline (Compound 20)

An anhydrous dichloromethane solution was prepared by mixing the thus-obtained t-butyl-dimethyl siloxy amide-L-proline (Compound 19) (550 mg, 1.8 mmol), 6-hydroxyhexanoic acid (300 mg, 2.3 mmol), EDC (434 mg, 2.3 mmol), and 1-hydroxybenzotriazole (695 mg, 4.5 mmol) in anhydrous dichloromethane (20 ml). Triethylamine (689 mg, 6.8 mmol) was added to this solution at room temperature in an argon atmosphere, and then, this was stirred overnight at room temperature in an argon atmosphere. The mixture was washed with saturated saline. An organic layer was collected, and the collected organic layer was dried with sodium sulfate. Thereafter, the organic layer was filtered. The solvent in the filtrate obtained was removed by evaporation under reduced pressure. The residual substance obtained was applied to silica gel column chromatography (the eluent: $CH_2Cl_2$:$CH_3OH$=9:1). Thus, Compound 20 in the form of colorless syrup was obtained (696 mg, yield: 92%). The result of NMR analysis with respect to this compound is shown below.

$^1$H-NMR (CDCl$_3$): δ4.54 (d, 1H, CH), 3.58-3.67 (m, 5H), 3.52-3.56 (m, 1H, CH), 3.32-3.39 (m, 1H), 3.20-3.25 (m, 2H), 2.40-2.43 (m, 1H, CH), 2.33 (t, J=7.3 Hz, 2H, CH$_2$), 2.05-2.25 (m, 2H), 1.93-2.03 (m, 1H, CH), 1.75-1.85 (m, 1H, CH), 1.50-1.73 (m, 8H), 1.37-1.46 (m, 2H, CH$_2$), 0.87 (s, 9H, t-Bu), 0.04 (s, 6H, SiCH$_3$);

Ms (FAB+): m/z 415 (M$^+$+1).

(4) DMTr-Hydroxy Diamide-L-Proline (Type B) (Compound 21)

The thus-obtained t-butyl-dimethyl siloxy amide hydroxy amide-L-proline (Compound 20) (640 mg, 1.54 mmol) was mixed with anhydrous pyridine (1 ml), and this was azeotropically dried at room temperature. To the residual substance obtained, 4,4'-dimethoxytrityl chloride (657 mg, 1.85 mmol), DMAP (2 mg), and anhydrous pyridine (5 ml) were added, and this was stirred for 4 hours at room temperature. Thereafter, methanol (1 ml) was added thereto, and this was stirred for 30 minutes at room temperature. The mixture was diluted with dichloromethane, and this was washed with saturated sodium bicarbonate water. An organic layer was collected and dried with sodium sulfate. Thereafter, the organic layer was filtered. The solvent in the filtrate obtained was removed by evaporation under reduced pressure. To the residual substance obtained, anhydrous acetonitrile (5 ml) and a 1 mol/l tetrabutylammonium fluoride-containing tetrahydrofuran solution (1.42 ml, tetrabutylammonium fluoride 1.42 mmol) were added, and this was stirred overnight at room temperature. After the completion of the reaction, ethyl acetate (100 ml) was added to the mixture. The resultant mixture was washed with water and then with saturated saline. An organic layer was collected and dried with sodium sulfate. Thereafter, the organic layer was filtered. The solvent in the filtrate obtained was removed by evaporation under reduced pressure. The residual substance obtained was applied to silica gel column chromatography (the eluent $CH_2Cl_2$: $CH_3OH$=95:5, containing 0.05% pyridine). Thus, Compound 21 in the form of colorless syrup was obtained (680 mg, yield: 73%). The result of NMR analysis with respect to this compound is shown below.

$^1$H-NMR (CDCl$_3$): δ7.41-7.44 (m, 2H, Ar—H), 7.26-7.33 (m, 4H, Ar—H), 7.18-7.21 (m, 2H, Ar—H), 7.17-7.21 (m, 1H, Ar—H), 6.80-6.84 (m, 4H, Ar—H), 4.51-4.53 (d, 6.8 Hz, 1H, CH), 3.79 (s, 6H, OCH$_3$), 3.61 (dd, 2H, J=11 Hz, 5.4 Hz, CH$_2$), 3.50-3.54 (m, 1H, CH), 3.36-3.43 (m, 1H, CH), 3.20-3.26 (m, 2H, CH$_2$), 3.05 (t, J=6.4 Hz, 2H, CH$_2$), 2.38-2.45 (m, 1H, CH), 2.30 (t, J=7.8 Hz, 2H, CH$_2$), 2.05-2.25 (m, 1H, CH), 1.92-2.00 (m, 1H, CH), 1.75-1.83 (m, 1H, CH), 1.52-1.67 (m, 8H), 1.35-1.45 (m, 2H, CH$_2$);

Ms (FAB+): m/z 602 (M$^+$), 303 (DMTr$^+$).

(5) DMTr-Diamide-L-Proline Amidite (Type B) (Compound 22)

The thus-obtained DMTr-hydroxy diamide-L-proline (type B) (Compound 21) (637 mg, 1.06 mmol) was mixed with anhydrous acetonitrile, and the resultant mixture was azeotropically dried at room temperature. To the residual substance obtained, diisopropylammonium tetrazolide (201 mg, 1.16 mmol) was added, and the resultant mixture was deaerated under reduced pressure and filled with argon gas. Anhydrous acetonitrile (1 ml) was added to the mixture, and an anhydrous acetonitrile solution (1 ml) of 2-cyanoethoxy-N,N,N',N'-tetraisopropyl phosphorodiamidite (350 mg, 1.16 mmol) was further added thereto. This mixture was stirred for 4 hours at room temperature in an argon atmosphere. The mixture was diluted with dichloromethane, and this was washed with saturated sodium bicarbonate water and saturated saline. An organic layer was collected and dried with sodium sulfate. Thereafter, the organic layer was filtered. The solvent in the filtrate obtained was removed by evaporation under reduced pressure. The residual substance obtained was applied to column chromatography using amino silica gel as a filler (the eluent: hexane:acetone=7:3). Thus, Compound 22 in the form of colorless syrup was obtained (680 mg, purity: 95%, yield: 76%). The result of NMR analysis with respect to this compound is shown below.

$^1$H-NMR (CDCl$_3$): δ7.41-7.43 (m, 2H, Ar—H), 7.25-7.32 (m, 4H, Ar—H), 7.17-7.22 (m, 2H, Ar—H), 6.80-6.83 (m,

4H, Ar—H), 4.53 (d, J=7.8 Hz, 1H, CH), 3.75-3.93 (m, 3H), 3.79 (s, 6H, OCH$_3$), 3.46-3.68 (m, 5H), 3.34-3.41 (m, 1H, CH), 3.10-3.31 (m, 1H, CH), 3.05 (t, J=6.3 Hz, 2H, CH$_2$), 2.62 (t, J=6.3 Hz, 2H, CH$_2$), 2.39-2.46 (m, 1H, CH), 2.29 (t, J=7.3 Hz, 2H, CH$_2$), 2.03-2.19 (m, 1H, CH), 1.90-2.00 (m, 1H, CH), 1.70-1.83 (m, 1H, CH), 1.51-1.71 (m, 8H), 1.35-1.45 (m, 2H, CH$_2$), 1.18 (d, J=6.4 Hz, 6H, CH$_3$), 1.16 (d, J=6.4 Hz, 6H, CH$_3$);

P-NMR(CH$_3$CN): δ146.90;

Ms (FAB+): m/z 803 (M$^+$+1), 303 (DMTr$^+$).

Example A5

In order to produce a nucleic acid molecule of the present invention including a linker having a proline skeleton, DMTr-amide ethylene oxy ethyl amino-L-proline amidite (hereinafter referred to as "PEG spacer type") was synthesized according to Scheme 5 shown below.

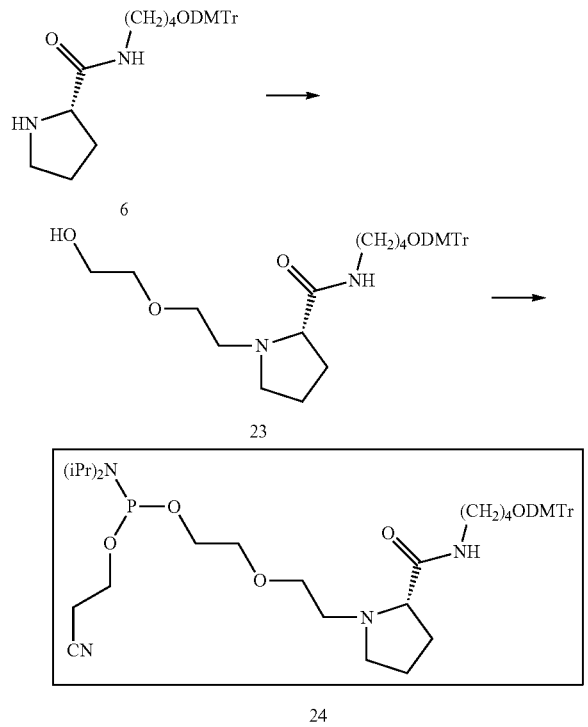

(1) DMTr-Amide Hydroxy Ethoxy Ethyl Amino-L-Proline (Compound 23)

DMTr-amide-L-proline (Compound 6) (1.00 g, 2.05 mmol), 4-toluenesulfonic acid 2-(2-hydroxyethoxy)ethyl ester (3.10 g, 12.30 mmol), and anhydrous dimethylformamide solution (10 ml) of potassium carbonate (0.85 g, 6.15 mmol) were mixed together, and the resultant mixture was stirred for 4 days at room temperature in an argon atmosphere. The solvent in the mixture was removed by evaporation at room temperature under reduced pressure. Thereafter, dichloromethane (20 ml) was added thereto, and the resultant mixture was filtered. The filtrate was concentrated, and the residual substance obtained was applied to silica gel column chromatography. As eluents in the silica gel column chromatography, first, ethyl acetate containing 0.05% pyridine was used, and then, a mixture of CH$_2$Cl$_2$ and CH$_3$OH(CH$_2$Cl$_2$: CH$_3$OH=9:1) containing 0.05% pyridine was used. As a result, Compound 23 in the form of colorless syrup was obtained (1.15 g, yield: 97%). The result of NMR analysis with respect to this compound is shown below.

$^1$H-NMR (CDCl$_3$): δ7.41-7.45 (m, 2H, Ar—H), 7.27-7.31 (m, 6H, Ar—H), 7.17-7.21 (m, 1H, Ar—H), 6.79-6.82 (m, 4H, Ar—H), 3.79 (s, 6H, OCH$_3$), 3.60-3.70 (m, 2H), 3.39-3.57 (m, 4H), 3.13-3.27 (m, 3H), 3.07-3.08 (m, 2H), 2.71-2.84 (m, 1H), 2.38-2.46 (m, 1H), 2.14-2.19 (m, 1H), 1.84-1.87 (m, 1H), 1.57-1.76 (m, 8H).

(2) DMTr-Amide Ethylene Oxy Ethyl Amino-L-Proline Amidite (Compound 24)

The thus-obtained DMTr-amide hydroxy ethoxy ethyl amino-L-proline (Compound 23) (0.63 g, 1.00 mmol) was mixed with anhydrous pyridine, and the resultant mixture was azeotropically dried at room temperature. To the residual substance obtained, diisopropylammonium tetrazolide (206 mg, 1.20 mmol) was added. The resultant mixture was deaerated under reduced pressure and filled with argon gas. Anhydrous acetonitrile (1 ml) was added to the mixture, and an anhydrous acetonitrile solution (1 ml) of 2-cyanoethoxy-N,N,N',N'-tetraisopropyl phosphorodiamidite (282 mg, 1.12 mmol) was further added thereto. This mixture was stirred for 4 hours at room temperature in an argon atmosphere. Then, the mixture was diluted with dichloromethane, and this was washed with saturated sodium bicarbonate water and saturated saline. An organic layer was collected and dried with sodium sulfate. Thereafter, the organic layer was filtered. The solvent in the filtrate obtained was removed by evaporation under reduced pressure. The residual substance obtained was applied to column chromatography using amino silica gel as a filler (the eluent: hexane:acetone=7:3, containing 0.05% pyridine). Thus, Compound 24 in the form of colorless syrup was obtained (0.74 g, purity: 100%, yield: 87%). The result of NMR analysis with respect to this compound is shown below.

$^1$H-NMR (CD$_3$CN): δ7.41-7.43 (m, 2H, Ar—H), 7.28-7.31 (m, 6H, Ar—H), 7.18-7.22 (m, 1H, Ar—H), 6.84-6.86 (m, 4H, Ar—H), 3.73-3.84 (m, 2H, CH$_2$), 3.79 (s, 6H, OCH$_3$), 3.47-3.64 (m, 7H), 3.15-3.23 (m, 1H), 3.11 (t, J=6.4 Hz, 2H, CH$_2$), 3.01 (t, J=5.9 Hz, 2H, CH$_2$), 2.95-2.99 (m, 1H), 2.58-2.63 (m, 2H), 2.31-2.35 (m, 1H, CH), 2.03-2.19 (m, 1H, CH), 1.48-1.78 (m, 10H), 1.12-1.57 (m, 12H, CH$_3$);

P-NMR (CD3CN): 6148.00;

Ms (FAB+): m/z 776 (Mt), 303 (DMTr$^+$) 201 (C$_8$H$_{19}$N$_2$OP$^+$).

Example A6

1. Synthesis of Protected Prolinol

According to Scheme 6 shown below, prolinol protected with a dimethoxytrityl group (Compound 3) was synthesized.

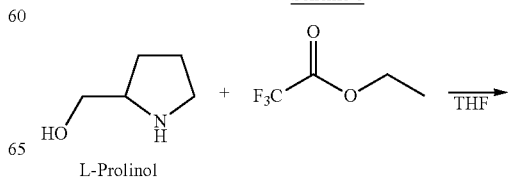

-continued

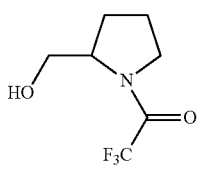

1

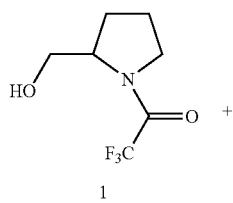

1

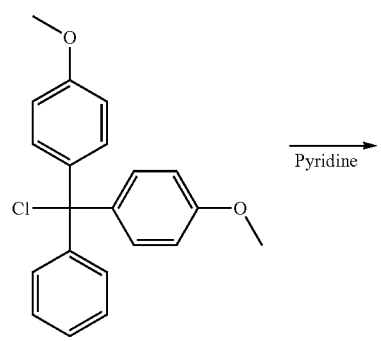

Pyridine →

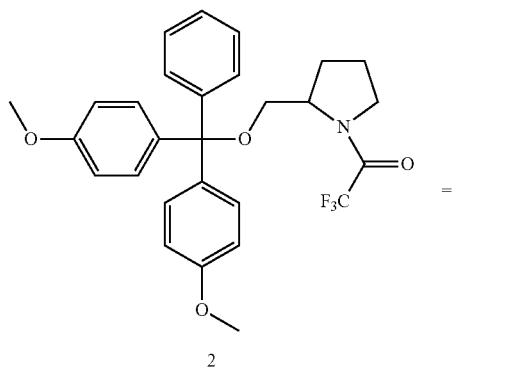

2

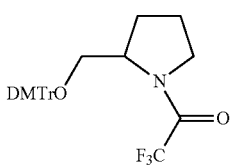

TBAF
NaOH aq
THF

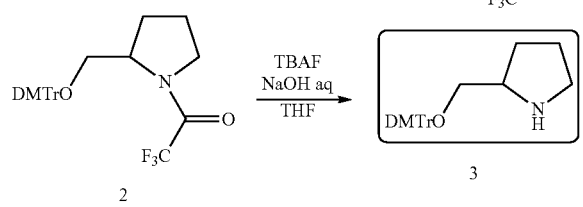

3

(1) Trifluoroacetyl-L-Prolinol (Compound 1)

L-prolinol (2.0 g, 20 mmol) was dissolved in 20 ml of THF. On the other hand, ethyl trifluoroacetate (3.0 g, 21 mmol) was dissolved in 20 ml of THF. Then, the latter THF solution was instilled in the former THF solution containing the L-prolinol, and this was stirred for 12 hours. This reaction solution was vacuum concentrated. Thus, Compound 1 was obtained (3.7 g, yield: 97%). The result of NMR analysis with respect to this compound is shown below.

$^1$H-NMR (CDCl$_3$): δ4.28-4, 23 (1.0H, m, OH), 3.90-3.41 (5H, H-2, H-5, H-6, m), 2.27-1.77 (4H, H-3, H-4, m).

(2) Trifluoroacetyl-DMTr-L-Prolinol (Compound 2)

The thus-obtained trifluoroacetyl-L-prolinol (Compound 1) (3.7 g, 19 mmol) was dissolved in pyridine, and the resultant mixture was azeotropically dried three times at room temperature. The residual substance obtained was dissolved in 15 ml of pyridine, and 4,4'-dimethoxytrityl chloride (DMTr-Cl) (8.1 g, 24 mmol) was added to this mixture while stirring the mixture in an ice bath under argon. They were allowed to further react for 4 hours at room temperature. Then, in order to quench excess DMTr-Cl, 10 ml of methanol was further added to the reaction solution, and this was stirred for 10 minutes. Thereafter, dichloromethane was added to the reaction solution, and the resultant mixture was washed with a saturated aqueous solution of sodium hydrogencarbonate and saturated saline. An organic layer collected after the washing was dried with sodium sulfate. The organic layer was filtered, and the filtrate obtained was vacuum concentrated. The residual substance obtained was applied to silica gel column chromatography (eluent CH$_2$Cl$_2$:CH$_3$OH=95:5, containing 0.1% pyridine). Thus, purified Compound 2 was obtained (8.5 g, yield: 89%). The result of NMR analysis with respect to this compound is shown below.

$^1$H-NMR (CDCl$_3$): δ7.39-7.18 (9H, m, Ar—H), 6.82 (4H, d, J=8.6 Hz, Ar—H), 3.78 (6H, s, OCH$_3$), 3.70-3.41 (5H, H-2, H-5, H-6, m), 2.19-1.85 (4H, H-3, H-4, m).

(3) DMTr-L-Prolinol (Compound 3)

The thus-obtained trifluoroacetyl-DMTr-L-prolinol (Compound 2) (5 g, 10 mmol) was dissolved in 100 ml of THF. 100 ml of a 5% aqueous solution of sodium hydroxide was added to this THF solution, and this then was stirred. 5 ml of 1M tetra-n-butylammonium fluoride (TBAF) solution was added to this solution, and this was stirred for 12 hours at room temperature. This reaction solution was washed with a saturated aqueous solution of sodium hydrogencarbonate and saturated saline. An organic layer collected after the washing was dried with sodium sulfate. The organic layer was filtered, and the filtrate obtained was vacuum concentrated. Thus, Compound 3 was obtained (3.6 g, yield: 90%). The result of NMR analysis with respect to this compound is shown below.

$^1$H-NMR (CDCl$_3$): δ7.40-7.14 (9H, m, Ar—H), 6.82 (4H, d, J=8.6 Hz, Ar—H), 3.78 (6H, s, OCH$_3$), 3.31 (1H, m, H-6), 3.07 (2H, m, H-2, H-6), 2.90 (2H, m, H-5), 1.84 (3H, m, H-3, H-4), 1.40 (1H, m, H-3).

2. Synthesis of Amidite Derivative

Using the protected prolinol (Compound 3) synthesized in the item "1" above, amidite derivatives having prolinol bound in various binding forms were synthesized according to Scheme 7 shown below.

Scheme 7

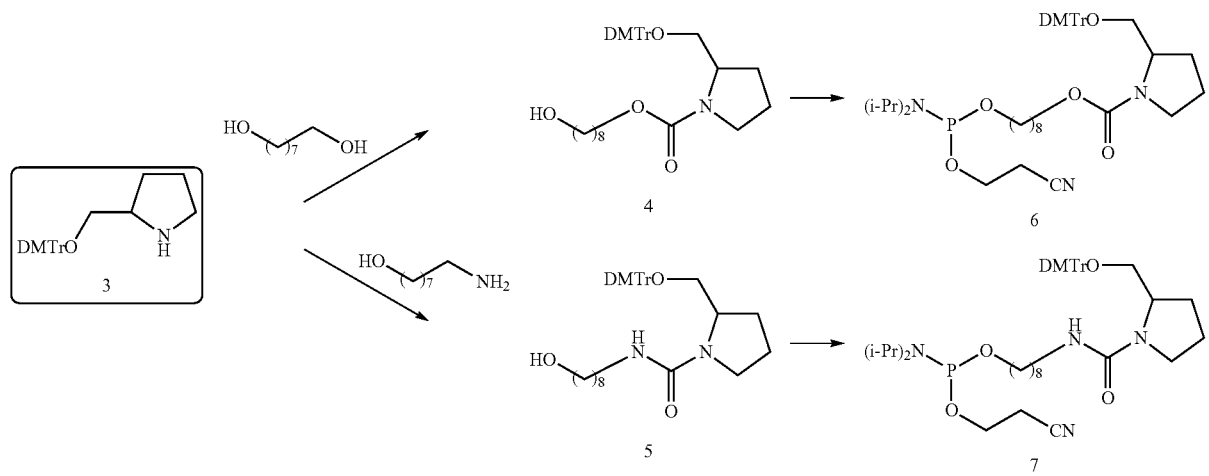

(1) DMTr-Urethane-L-Prolinol (Compound 4)

1,8-octanediol (9.0 g, 62 mmol) was dissolved in 90 ml of THF, and this solution was placed under argon. On the other hand, carbonyldiimidazole (2.0 g, 12 mmol) was dissolved in 10 ml of THF. The latter THF solution was added to the former THF solution, and this was stirred for 1 hour at room temperature. This reaction solution was washed with water until a spot of the 1,8-octanediol no longer was observed in TLC. Further, an organic layer collected after the washing was washed with saturated saline and dried with anhydrous sodium sulfate. The organic layer was filtered, and the filtrate obtained was vacuum concentrated. The residual substance obtained was applied to silica gel column chromatography (the eluent: $CH_2Cl_2:CH_3OH=95:5$). Thus, a purified title compound was obtained. In this compound, one end of the 1,8-octanediol was activated with carbonyldiimidazole (2.3 g, yield: 77%).

0.9 g of the compound was dissolved in 10 ml of acetonitrile, and this solution was placed under argon. On the other hand, DMTr-L-prolinol (Compound 3) (1.9 g, 4.8 mmol) was dissolved in 20 ml of acetonitrile. The latter acetonitrile solution was added to the former acetonitrile solution, and this was stirred for 24 hours at room temperature. Then, this reaction solution was washed with a saturated aqueous solution of sodium hydrogencarbonate and saturated saline. An organic layer was collected and dried with anhydrous sodium sulfate. The organic layer was filtered, and the filtrate obtained was vacuum concentrated. The residual substance obtained was applied to silica gel column chromatography (the eluent dichloromethane:acetone=9:1, containing 0.1% pyridine). Thus, purified Compound 4 (prolinol-urethane-amidite) was obtained (1.5 g, yield: 65%). The result of NMR analysis with respect to this compound is shown below.

$^1$H-NMR (CDCl$_3$): δ7.40-7.14 (9H, m, Ar—H), 6.82 (4H, d, J=8.6 Hz, Ar—H), 4.24-3.94 (2H, m, COOCH$_2$), 3.78 (s, 6H, OCH$_3$), 3.72-2.96 (7H, m, alkyl, H-2, H-5, H-6), 2.10-1.30 (16H, m, alkyl, H-3, H-4);

FAB-MS: 576 [M+H]$^+$.

(2) DMTr-Ureido-L-Prolinol (Compound 5)

Under argon, triphosgene (2.0 g, 6.7 mmol) was dissolved in 10 ml of THF, and this was stirred at 0° C. On the other hand, DMTr-L-prolinol (Compound 3) (1.3 g, 3.2 mmol) and N,N-diisopropylethylamine (16 g, 124 mmol) were dissolved in 10 ml of THF, and this solution was instilled in the THF solution of triphosgene. This reaction solution was stirred for 1 hour at 0° C. and then for 2 hours at room temperature. Then, 8-amino-1-octanol (2.3 g, 16 mmol) and N,N-diisopropylethylamine (5.0 g, 38 mmol) were dissolved in 30 ml of THF. The reaction solution having been stirred was instilled in this THF solution, and this was stirred for 1 hour at 0° C. and then for 48 hours at room temperature. This reaction solution was vacuum concentrated, and the residual substance obtained was dissolved in dichloromethane. This solution was washed with a saturated aqueous solution of sodium hydrogencarbonate and saturated saline. An organic layer was collected and dried with anhydrous sodium sulfate. The organic layer was filtered, and the filtrate obtained was vacuum concentrated. The residual substance obtained was purified by applying it to reverse-phase silica gel column chromatography. At this time, the eluent used was a mixed solvent of acetone and water, containing 0.1% pyridine, and the mixing ratio between the acetone and water was changed stepwise. Specifically, the molar ratio between the acetone and water (acetone:water) was changed gradually so as to be 2:8, 3:7, 4:6, and 5:5 in this order. A fraction containing Compound 5 as a target compound was extracted with dichloromethane, and the thus-obtained organic layer was dried with anhydrous sodium sulfate. The organic layer was filtered, and the filtrate obtained was vacuum concentrated. Thus, Compound 5 (prolinol ureido amidite) was obtained (0.9 g, yield: 49%). The result of NMR analysis with respect to this compound is shown below.

$^1$H-NMR (CDCl$_3$): δ7.40-7.14 (9H, m, Ar—H), 6.82 (41-1, m, Ar—H), 3.78 (s, 6H, OCH$_3$), 3.68-3.25 (9H, m, CH$_2$NH, CH$_2$OH, H-2, H-5, H-6), 1.74-1.18 (16H, m, alkyl, H-3, H-4);

FAB-MS: 575 [M+H]$^+$.

(3) Amidite Derivatives Having Prolinol (Compounds 6 and 7)

As a modified prolinol, the thus-obtained Compound 4 (0.80 g, 1.4 mmol) was dissolved in acetonitrile, and the resultant mixture was azeotropically dried three times at room temperature. The residual substance obtained was dissolved in 1 ml of acetonitrile, and the solution was placed under argon. Diisopropylammonium tetrazolide (0.24 g, 1.4 mmol) was added to this acetonitrile solution, thus providing a reaction solution. On the other hand, 2-cyanoethyl N,N,N',N'-tetraisopropyl phosphorodiamidite (0.50 g, 1.7 mmol) was dissolved in 1 ml of acetonitrile. This was added to the reaction solution, and the resultant mixture was stirred for 4 hours at room temperature. Dichloromethane was added to the reaction solution, and the resultant mixture was washed with a saturated aqueous solution of sodium hydrogencarbonate and saturated saline. An organic layer collected after the washing was dried with anhydrous sodium sulfate. The organic layer was filtered, and the filtrate obtained was vacuum concentrated. The residual substance obtained was applied to amino silica gel column chromatography (the eluent: hexane:acetone=10: 1, containing 0.1% pyridine). Thus, purified Compound 6 (DMTr-urethane-L-prolinol amidite) was obtained (0.90 g, yield: 83%). The result of NMR analysis with respect to this compound is shown below.

$^1$H-NMR (CDCl$_3$): δ7.40-7.14 (9H, m, Ar—H), 6.82 (4H, d, J=8.6 Hz, Ar—H), 4.24-3.94 (2H, m, COOCH$_2$), 3.78 (s, 6H, MHO, 3.72-2.96 (11H, m, CH$_2$O, POCH$_2$, CHCH$_3$, H-2, H-5, H-6), 2.58 (2H, m, CH$_2$CN), 2.10-1.46 (16H, m, alkyl, H-3, H-4), 1.34-1.10 (12H, m, CHCH$_3$);

$^{31}$P-NMR: (CD3CN) δ146.82;

FAB-MS: 776 [M+H]$^+$.

Purified Compound 7 (DMTr-ureido-L-prolinol amidite) (0.80 g, yield: 74%) was obtained in the same manner as in the above, except that, as the modified prolinol, Compound 5 was used instead of Compound 4. The result of NMR analysis with respect to this compound is shown below.

$^1$H-NMR (CDCl$_3$): δ7.40-7.14 (9H, m, Ar—H), 6.82 (4H, m, Ar—H), 3.78 (s, 6H, OCH$_3$), 3.65-3.25 (13H, m, CH$_2$O, POCH$_2$, CHCH$_3$, H-2, CH$_2$NH, CH$_2$OH, H-2, H-5, H-6), 2.73 (2H, m, CH$_2$CN), 2.10-1.48 (16H, m, alkyl, H-3, H-4), 1.35-1.10 (12H, m, CHCH$_3$);

$^{31}$P-NMR (CD$_3$CN) δ 146.83;

FAB-MS: 775 [M+H]$^+$.

Example B1

Solid-Phase Synthesis of RNA

RNA having the linker of the present invention was synthesized. The RNA was synthesized from its 3' side toward its 5' side based on a phosphoramidite method with the use of a nucleic acid synthesizer (trade name: ABI Expedite (registered trademark) 8909 Nucleic Acid Synthesis System, Applied Biosystems). In the synthesis, RNA Phosphoramidites (2'-O-TBDMSi, trade name, Samchully Pharm. Co., Ltd.) were used as RNA amidites (the same applies hereinafter). The amidites were deprotected by a conventional method, and the synthesized RNAs were purified by HPLC. In the following examples, synthesis of RNAs was carried out in the same manner as in the present example, unless otherwise stated.

Specifically, as RNA (Ex) of the present example, ssRNA (PH-0001) having Compound 12 shown in Scheme 2 as a linker was synthesized. First, RNA having a sequence shown in SEQ ID NO: 1 below was synthesized. Then, Compound 12 was linked to the 5' end of the RNA. Furthermore, on the 5' side of the RNA shown in SEQ ID NO: 1, RNA having a sequence shown in SEQ ID NO: 2 below was synthesized via Compound 12.

```
                                              (SEQ ID NO: 1)
5'-GGCUGUUGUCAUACUUCUCAUGGUU-3'

(SEQ ID NO: 2)
5'-CCAUGAGAAGUAUGACAACAGCC-3'
```

The thus-synthesized ssRNA is referred to as ssRNA (PH-0001) of the present example. As shown in SEQ ID NO: 3 below, the structure of PH-0001 is such that: the RNA sequence of SEQ ID NO: 2 is on its 5' side; the RNA sequence of SEQ ID NO: 1 is on its 3' side; and these RNA sequences are linked to each other via the linker Lx (i.e., Compound 12). Furthermore, as shown in the following sequence, the RNA sequence of SEQ ID NO: 2 is complementary to the RNA sequence of SEQ ID NO: 1. Thus, as shown in the formula shown below, PH-0001 has a stem structure as a result of self-annealing. In the following sequence, the underlined part "GUUGUCAUACUUCUCAUGG" (SEQ ID NO: 4) is a region involved in the inhibition of the GAPDH gene expression.

```
Ex: PH-0001                                   (SEQ ID NO: 3)
5'-CCAUGAGAAGUAUGACAACAGCC-Lx-
GGCUGUUGUCAUACUUCUCAUGGUU-3'
```

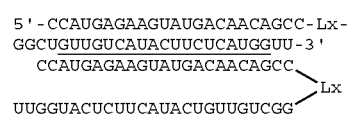

On the other hand, as RNA of a comparative example without a linker of the present invention, the following shRNA (NH-0001) as an RNAi positive control (Pc) was synthesized. As shown below, in this NH-0001, the sequence of the 5' region indicated with capital letters is the same as that in PH-0001, i.e., the RNA sequence of SEQ ID NO: 2, and the sequence of the 3' region indicated with capital letters is the same as that in PH-0001, i.e., the RNA sequence of SEQ ID NO: 1. Between the RNA sequence of SEQ ID NO: 2 and the RNA sequence of SEQ ID NO: 1, NH-0001 has the RNA sequence indicated with lower-case letters as a linker, instead of Compound 12. Similarly to PH-0001, NI-1-0001 forms a stem by self-annealing, thus having an shRNA structure, as shown in the formula shown below. In the following sequence, the underlined part "GUUGUCAUACUUCUCAUGG" (SEQ ID NO: 4) is a region involved in the inhibition of expression.

```
Pc: NH-0001                                   (SEQ ID NO: 5)
5'-CCAUGAGAAGUAUGACAACAGCCccacaccGGCUGUUGUCAUACUUCUCAUGGUU-3'
```

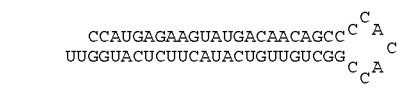

Example B2

Inhibitory Effect on the GAPDH Gene Expression in HCT116 cells

Using the RNA of the present invention, inhibition of the GAPDH gene expression in vitro was examined.
(1) Materials and Method
As RNA (Ex) of the present example, ssRNA (PH-0001) of Example B1 was used. RNA solutions were prepared by dissolving the RNA in distilled water for injection (Otsuka Pharmaceutical Co., Ltd., hereinafter the same) so as to achieve desired concentrations (1 μmol/l, 5 μmol/l, and 25 μmol/l).

HCT116 cells (DS Pharma Biomedical Co., Ltd.) were used as cells. A 10% FBS-containing McCoy's 5A (Invitrogen) medium was used as a medium. The culture conditions were set to 37° C. and 5% $CO_2$.

First, the HCT116 cells were cultured in the medium, and were dispensed to a 24-well plate so that each well contained 400 μl of the medium to achieve a density of $2\times10^4$ cells/well. The cells in the wells were cultured for another 24 hours. Thereafter, the cells were transfected with the RNA using a transfection reagent Lipofectamine 2000 (Invitrogen) according to the protocol supplied therewith. Specifically, the transfection was carried out by setting the composition per well as follows. The final concentration of the RNA in the well was set to 1 nmol/l, 5 nmol/l, or 25 nmol/l.

TABLE 1

| (Composition per well: μl) | |
| --- | --- |
| Medium | 400 |
| (A) Lipofectamine 2000 | 1.5 |
| (B) Opti-MEM (Invitrogen) | 98 |
| (C) RNA solution | 0.5 |
| Total | 500 |

After the transfection, the cells in the wells were cultured for 24 hours, and then, the RNA was collected using an RNeasy Mini Kit (Qiagen, the Netherlands) according to the protocol supplied therewith. Subsequently, cDNA was synthesized from the RNA using a reverse transcriptase (trade name: SuperScript III, Invitrogen) according to the protocol supplied therewith. Then, as described below, PCR was carried out using the thus-synthesized cDNA as a template, and the expression level of the GAPDH gene and that of the β-actin gene as an internal standard were measured. The expression level of the GAPDH gene was corrected with reference to that of the β-actin gene.

The PCR was carried out using a LightCycler FastStart DNA Master SYBR Green I (trade name, Roche) as a reagent and a Light Cycler DX400 (trade name, Roche) as an instrument (hereinafter the same). The GAPDH gene and the β-actin gene were amplified using the following primer sets, respectively.

```
PCR Primer set for GAPDH gene
                              (SEQ ID NO: 7)
5'-GGAGAAGGCTGGGGCTCATTTGC-3'

(SEQ ID NO: 8)
5'-TGGCCAGGGGTGCTAAGCAGTTG-3'

Primer set for β-actin gene
                              (SEQ ID NO: 9)
5'-GCCACGGCTGCTTCCAGCTCCTC-3'

(SEQ ID NO: 10)
5'-AGGTCTTTGCGGATGTCCACGTCAC-3'
```

As Control 1, regarding the cells to which 100 μl of the solution (B) only had been added, the amounts of the genes expressed also were measured (−). Furthermore, as Control 2, regarding the cells subjected to the same transfection procedures as in the above except that the RNA solution was not added and that (B) and 1.5 μl of (A) were added so that the total amount of (A) and (B) would be 100 μl, the expression level of the gene also was measured (mock).

Then, the corrected expression level of the GAPDH gene in the control (−) was set as 1, and that in the cells transfected with the RNA at each concentration was presented as the relative value to that in the control (−).

(2) Results

Figure 4:
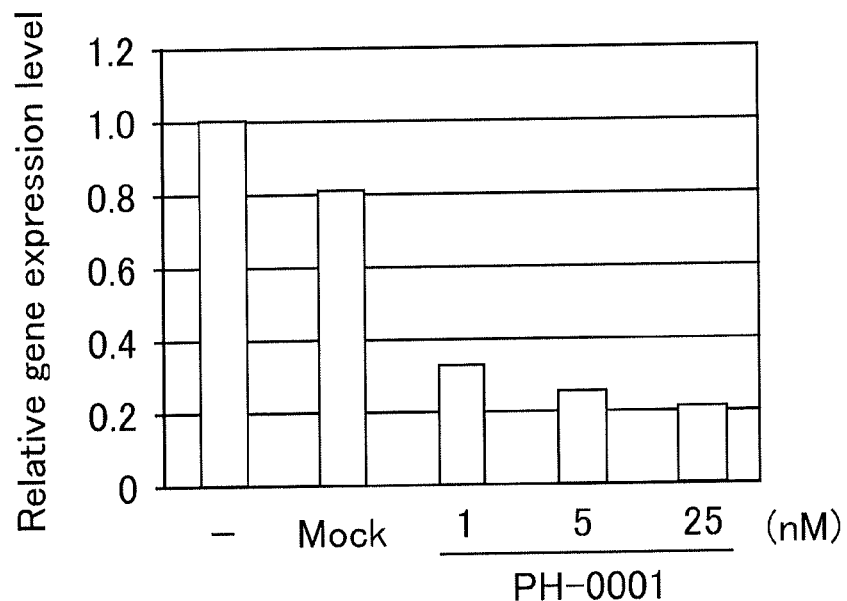
FIG. 4 is a graph showing the relative expression level of the GAPDH gene in an example of the present invention.

The results thereof are shown in FIG. 4. FIG. 4 is a graph showing the relative expression level of the GAPDH gene, and the vertical axis indicates the relative gene expression level. As can be seen from FIG. 4, the inhibitory activity of PH-0001 of Example B1 was not impaired. Also, it is considered that PH-0001 is stabilized by Compound 12 as the linker of the present invention.

Example B3

Stability in Human Serum

Regarding the RNA of the present invention, the stability in human serum was examined.

(1) Materials and Method

As RNA (Ex) of the present example, ssRNA (PH-0001) of Example B1 was used. As RNA of a comparative example, shRNA (NH-0001) as RNAi positive control (Pc) used in Example B1 was used.

First, each of the RNAs and normal human serum (MP Biomedicals) were mixed in 1×PBS, and 30 μl of this mixture was incubated at 37° C. In 30 μl of the mixture, the amount of the RNA added was set to 60 μmol, and the amount of the normal human serum added was set so that the final concentration thereof was 10%. Then, 0 hours, 0.5 hours, 1 hour, and 2 hours after the start of the incubation, the reaction was terminated by extraction with phenol and chloroform. The liquid extract obtained was subjected to electrophoresis using 15% polyacrylamide gel. Thereafter, the gel was stained with SYBR Green II (trade name, Lonza), and then analyzed using an E-BOX-VX2 (M & S Instruments Inc., Tokyo).

(2) Results

Figure 5:
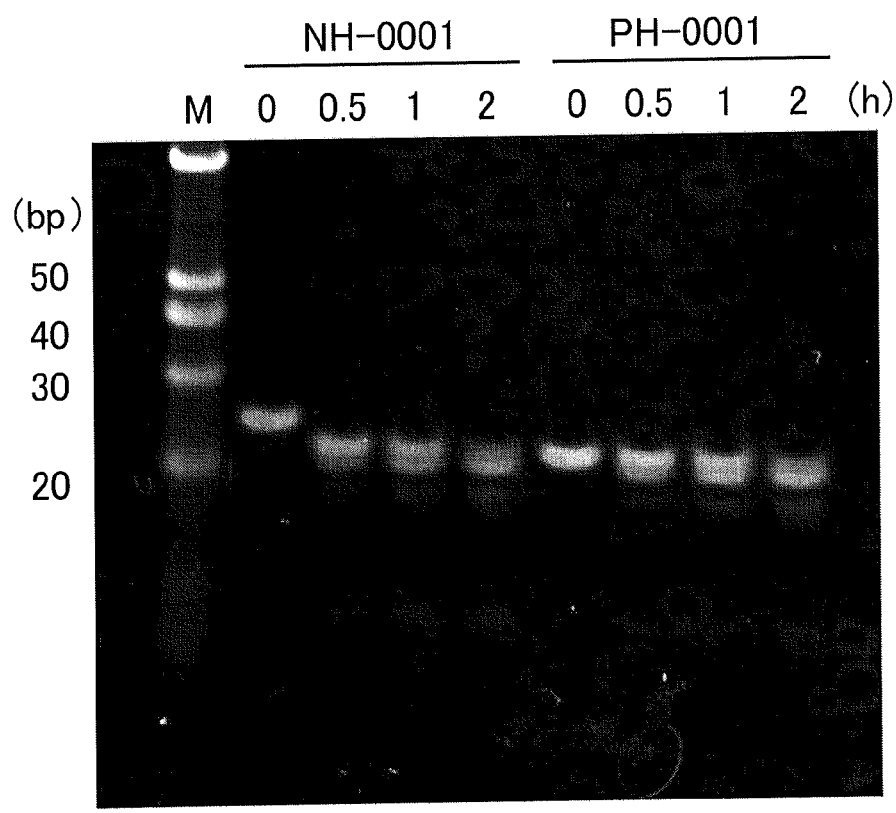
FIG. 5 is an electrophoretogram showing the stability in still another example of the present invention.

The results thereof are shown in FIG. 5. FIG. 5 is an electrophoretogram showing the stability. In FIG. 5, the lane "M" indicates a molecular weight marker, and "(h)" indicates the incubation time.

As can be seen from FIG. 5, regarding NH-0001 of the comparative example composed of a natural nucleotide, it was found that a rapid degradation reaction was started as early as 0.5 hours after the start of the incubation, and as a result, the sizes of the RNA at all the time points from 0.5 to 2 hours after the start of the incubation were smaller than the size of the RNA at 0 hours after the start of the incubation. In contrast, regarding PH-0001 of the example including the linker of the present invention, substantially no change in mobility with incubation time, i.e., substantially no decrease in molecular weight due to the degradation, was observed. These results demonstrate that RNA having the linker of the present invention can achieve an improved stability in human serum.

Example B4

Inhibitory Effect on the GAPDH Gene Expression in HCT116 Cells ssRNA including a proline-containing linker represented by the following formula was synthesize, and the inhibitory effect of the ssRNA on the GAPDH gene was examined.

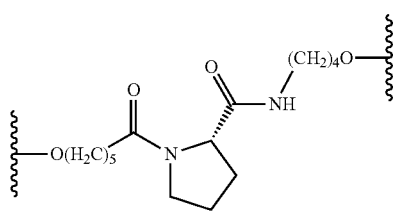

(1) Materials and Method
(1.1) Solid-Phase Synthesis of ssRNA

The RNA was synthesized based on a phosphoramidite method in the same manner as in Example B1.

As RNA (Ex) of the present example, ssRNA (PK-0004) shown below was used. In the following sequence, "Lx" and "Ly" are each the proline-containing linker represented by the above formula (shown in the paragraph [0275]). In the synthesis of the ssRNA, the ssRNA was synthesized from its 3' side using the RNA amidites (trade name "RNA Phosphoramidites", Samchully Pharm. Co., Ltd.) according to SEQ ID NO: 11. At the sites of "Lx" and "Ly", DMTr-diamide-L-proline amidites (Compounds 10 in Scheme 3) synthesized in Example A3-1 were linked. In the sequence, "GUUGU-CAUACUUCUCAUGG" (SEQ ID NO: 4) is a region involved in the inhibition of expression.

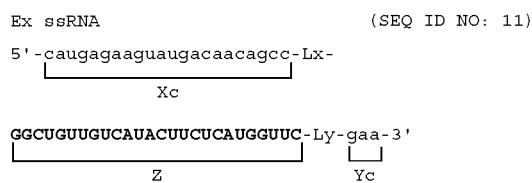

As RNA of a comparative example, ssRNA (PK-0003) as an RNAi negative control (Nc) was used. In the following sequence, "Lx" and "Ly" are each the proline-containing linker represented by the above formula (shown in the paragraph [0275]). In the synthesis of the ssRNA, the ssRNA was synthesized from its 3' side using the RNA amidites (trade name "RNA Phosphoramidites", Samchully Pharm. Co., Ltd.) according to SEQ ID NO: 12. At the sites of "Lx" and "Ly", DMTr-diamide-L-proline amidites synthesized in Example A3 (Compounds 10 in Scheme 3) were linked. This ssRNA was designed so as to incorporate a scrambled sequence instead of the expression inhibitory sequence.

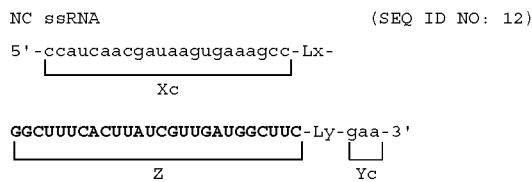

(1.2) Inhibition of Gene Expression

RNA solution was prepared by dissolving each of the RNAs that had been cryopreserved in distilled water for injection (Otsuka Pharmaceutical Co., Ltd.) so as to achieve a concentration of 20 μmol/l.

Using the RNA solution, the expression level of the GAPDH gene in HCT116 cells was measured in the same manner as in Example B2. In the transfection, the composition per well was set as follows. In the following composition, (B) is Opti-MEM (Invitrogen), (C) is the RNA solution of 20 μmol/l, and they were added so that the total amount thereof would be 98.5 μl. The final concentration of the RNA in the well was set to 1 nmol/l, 3 nmol/l, or 10 nmol/l.

TABLE 2

| (Composition per well: μl) | |
|---|---|
| Medium | 400 |
| (A) Lipofectamine 2000 | 1.5 |
| (B) + (C) | 98.5 |
| Total | 500 |

(2) Results

Figure 6:
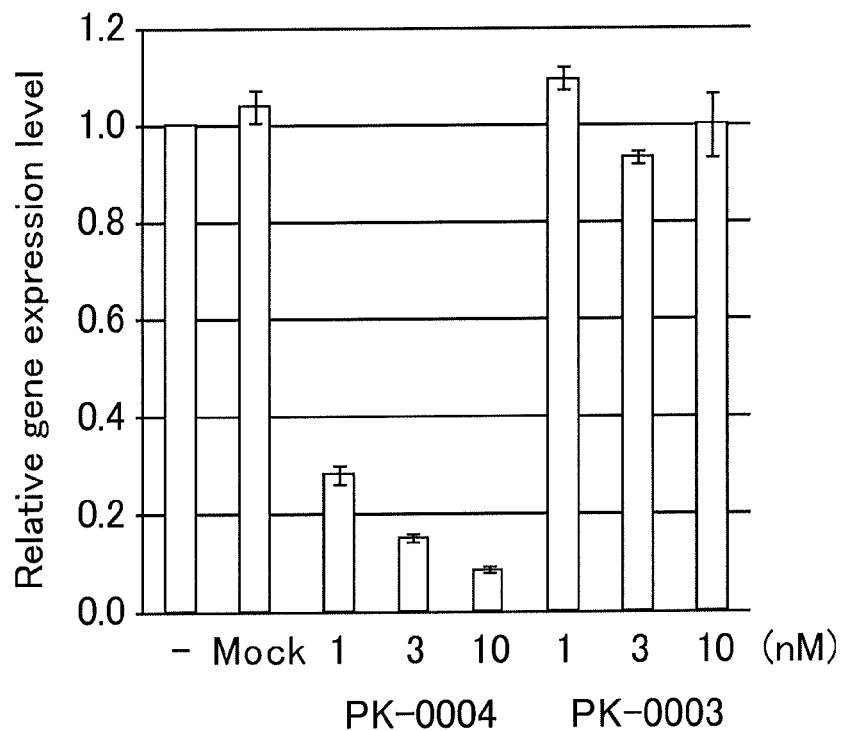
FIG. 6 is a graph showing the relative expression level of the GAPDH gene in still another example of the present invention.

The results thereof are shown in FIG. 6. FIG. 6 is a graph showing the relative expression level of the GAPDH gene. As can be seen from FIG. 6, PK-0004 of the example having the linker of the present invention exhibited a potent inhibitory activity, and the activity was dose-dependent. On the other hand, no inhibitory effect was observed when PK-0003 as the negative control was used.

Example B5

Reactivity of Dicer Protein

The reactivity of a recombinant human Dicer protein with ssRNA having undergone substitution with a linker having proline was examined.

(1) Materials and Method

As RNA (Ex) of the present example, ssRNA (PK-0004) of Example B4 was used. As RNAs of a comparative example, ssRNA (PK-0003) as an RNAi negative control (Nc) shown in Example B4 and ssRNA (NK-0016) shown below as an RNAi positive control (Pc) were used. The structure of NK-0016 is such that the sequences of the 5' side region (Xc), the inner 5' side region (X), the 3' side region (Yc), and the inner 3' side region (Y) are the same as those in PK-0004, and between Xc and X and between Yc and Y, polynucleotides were provided as linkers instead of the linkers (Lx, Ly) represented by the above formula (shown in the paragraph [0275]) used in PK-0004.

A reaction solution containing the Dicer protein and each of the RNAs was prepared using Coldshock-DICER (trade name, Takara Bio Inc.) as a reagent according to the protocol supplied therewith. This reaction solution was incubated at 37° C. The incubation time was set to 0, 3, 6, or 9 hours. To the reaction solution having undergone the predetermined time of incubation, a reaction-terminating solution accompanying the reagent was added. Then, the solution was subjected to electrophoresis using 15% polyacrylamide gel. Thereafter, the gel was stained with SYBR Green II (trade name, Lonza), and then analyzed using an E-BOX-VX2 (trade name, M & S Instruments Inc.).

(2) Results and Consideration

Figure 7:
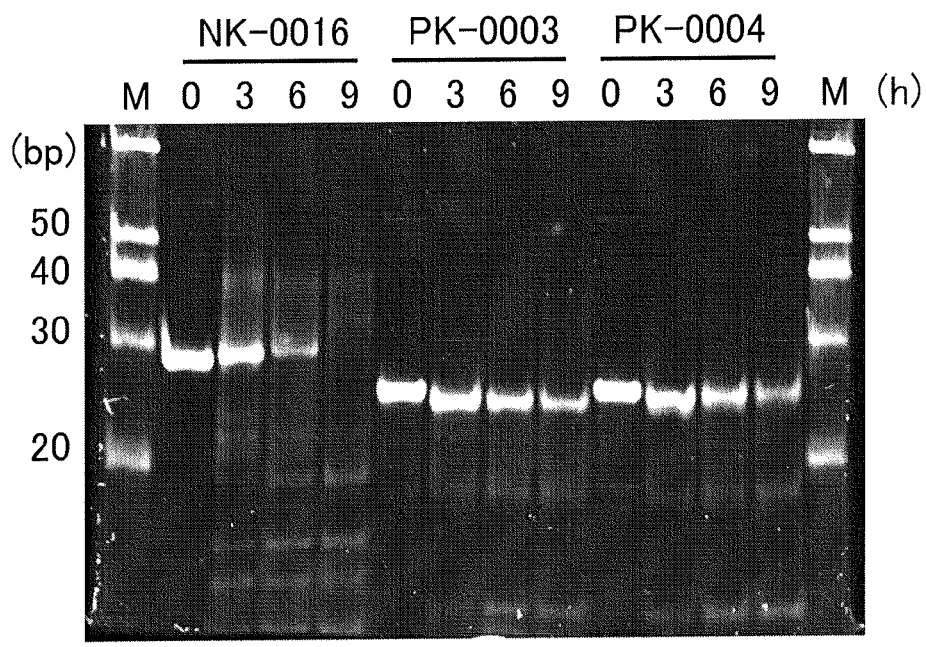
FIG. 7 shows the results of electrophoresis, which indicate the reactivity of a Dicer protein with ssRNAs in still another example of the present invention.

The results thereof are shown in FIG. 7. FIG. 7 shows the results of electrophoresis, which indicate the reactivity of the Dicer protein with the ssRNAs. In FIG. 7, the lane "M" indicates a molecular weight marker (20 bp, 30 bp, 40 bp, 50 bp), and "(h)" indicates the incubation time.

NK-0016 of the comparative example composed of a natural nucleotide reacted rapidly with the Dicer protein and disappeared before a lapse of 9 hours from the start of the incubation. In contrast, the RNAs having the linker containing proline, i.e., PK-0004 of the example and PK-0003 as the negative control, reacted gradually with the Dicer protein, so that they did not disappear completely even 9 hours after the start of the incubation. From these results, it was found that the stability in cells is improved by incorporating a linker containing proline. That is, considering these results together with the results obtained regarding the gene inhibitory effect, it is concluded that the RNA of the present invention having a linker containing proline has an effect of improving the durability of the RNA interference effect in cells.

Example B6

Inhibitory Effect on the GAPDH Gene Expression in A549 Cells and 293 Cells

Using ssRNA having undergone substitution with a linker having proline, inhibition of the GAPDH gene expression in vitro was examined.

(1) Materials and Method

As RNA (Ex) of the present example, ssRNA (PK-0004) of Example B4 was used. As RNA of a comparative example, ssRNA (PK-0003) as an RNAi negative control (Nc) shown in Example B4 was used. RNA solution was prepared by dissolving each of the RNAs in distilled water for injection (Otsuka Pharmaceutical Co., Ltd.) so as to achieve a concentration of 20 μmol/l.

A549 cells and 293 cells (DS Pharma Biomedical Co., Ltd.) were used as cells. As a medium for the former cells, a 10% FBS-containing DMEM (Invitrogen) was used. As a medium for the latter cells, a 10% FBS-containing MEM (Invitrogen) was used. The culture conditions were set to 37° C. and 5% $CO_2$.

First, the cells of each type were cultured in the medium, and were dispensed to a 24-well plate so that each well contained 400 μl of the medium to achieve a density of $5\times10^4$ cells/well. The cells in the wells were cultured for another 24 hours. Thereafter, the cells were transfected with the RNA using a transfection reagent Lipofectamine 2000 (Invitrogen) according to the protocol supplied therewith. Specifically, the transfection was carried out by setting the composition per well as follows for the A549 cells and the 293 cells. In the following composition, (B) is Opti-MEM (Invitrogen), and (C) is the RNA solution of 20 μmol/l, and they were added so that the total amount of (B) and (C) would be 98.5 μl or 99 μl.

The final concentration of the RNA in the well was set to 1 nmol/l, 3 nmol/l, or 10 nmol/l.

TABLE 3

| (Composition per well: μl) | | |
| --- | --- | --- |
| | A549 cells | 293 cells |
| Medium | 400 | 400 |
| (A) Lipofectamine 2000 | 1.5 | 1 |
| (B) + (C) | 98.5 | 99 |
| Total | 500 | 500 |

After the transfection, culture of the cells, collection of the RNA, synthesis of cDNA, and PCR were carried out in the same manner as in Example B4, and the relative expression level of the GAPDH gene was determined.

(2) Results

Figure 8:
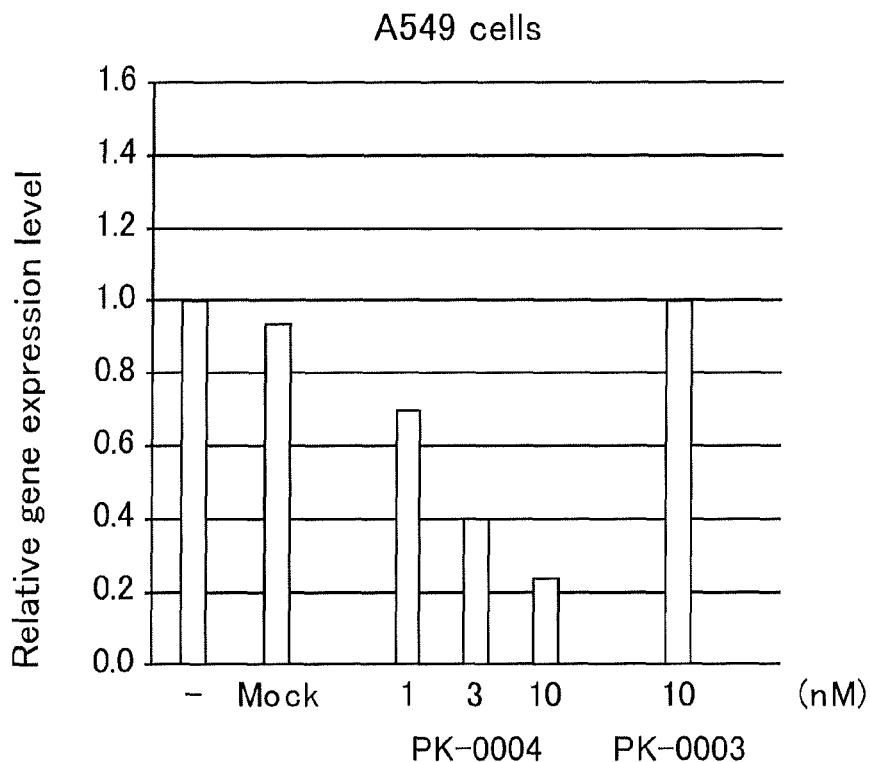
FIG. 8 is a graph showing the relative expression level of the GAPDH gene in A549 cells in still another example of the present invention
Figure 9:
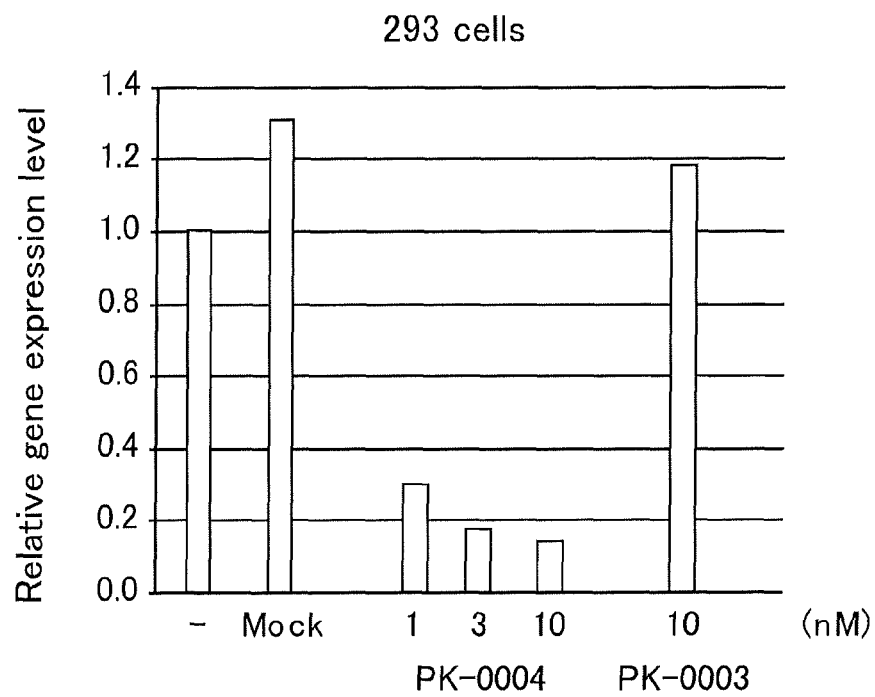
FIG. 9 is a graph showing a relative expression level of the GAPDH gene in 293 cells in the example of the present invention.

The results thereof are shown in FIGS. 8 and 9. FIG. 8 shows the result obtained regarding the A549 cells, and FIG. 9 shows the result obtained regarding the 293 cells. FIGS. 8 and 9 are each a graph showing the relative expression level of the GAPDH gene. As can be seen from FIGS. 8 and 9, it was found that PK-0004 according to the example exhibits a potent inhibitory activity, and exhibits a gene inhibitory effect in a concentration-dependent manner. On the other hand, no inhibitory effect was observed when PK-0003 as the negative control was used.

Example B7

Inhibitory Effect on the GAPDH Gene Expression in HCT116 Cells

Using ssRNA having undergone substitution with a linker having proline or prolinol, the inhibitory effect on the GAPDH expression in HCT116 cells was examined.

(1) Materials and Method (1.1) Solid-Phase Synthesis of ssRNA

As RNA of the present example (Ex ssRNA), the same Ex ssRNA as used in Example B4 was synthesized. The RNA was synthesized in the same manner as in Example B4, unless otherwise stated.

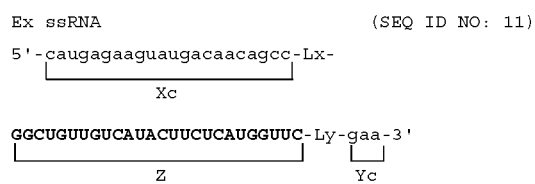

As amidites for linker synthesis, L-proline-diamide-amidite (Compound 10 in Scheme 3) synthesized in Example A3-1, and prolinol-urethane-amidite (Compound 6 in Scheme 7), prolinol-ureide-amidite (Compound 7 in Scheme 7), proline-amide-amine-amidite (Compound 12 in Scheme 3), and proline-amide-ureide-amidite (Compound 17 in Scheme 3) synthesized in Example A6 were used. Regarding the thus-synthesized respective RNAs, the amidites used for the synthesis of their linker moieties are shown in the table below.

TABLE 4

| ssRNA | Amidite used in Lx and Ly |
|---|---|
| PK-0004 | L-proline-diamide-amidite (Compound 10 in Scheme 3) |
| PK-0006 | prolinol-urethane-amidite (Compound 6 in Scheme 7) |
| PK-0010 | proline-amide-amine-amidite (Compound 12 in Scheme 3) |
| PK-0012 | proline-amide-ureide-amidite (Compound 17 in Scheme 3) |
| PK-0016 | prolinol-ureide-amidite (Compound 7 in Scheme 7) |

(1.2) Inhibition of Gene Expression

Transfection into HCT116 cells, culture, collection of RNA, synthesis of cDNA, and PCR were carried out in the same manner as in Example B4, except that each of the above RNAs wad used, and the relative expression level of the GAPDH gene was determined.

(2) Results

Figure 10:
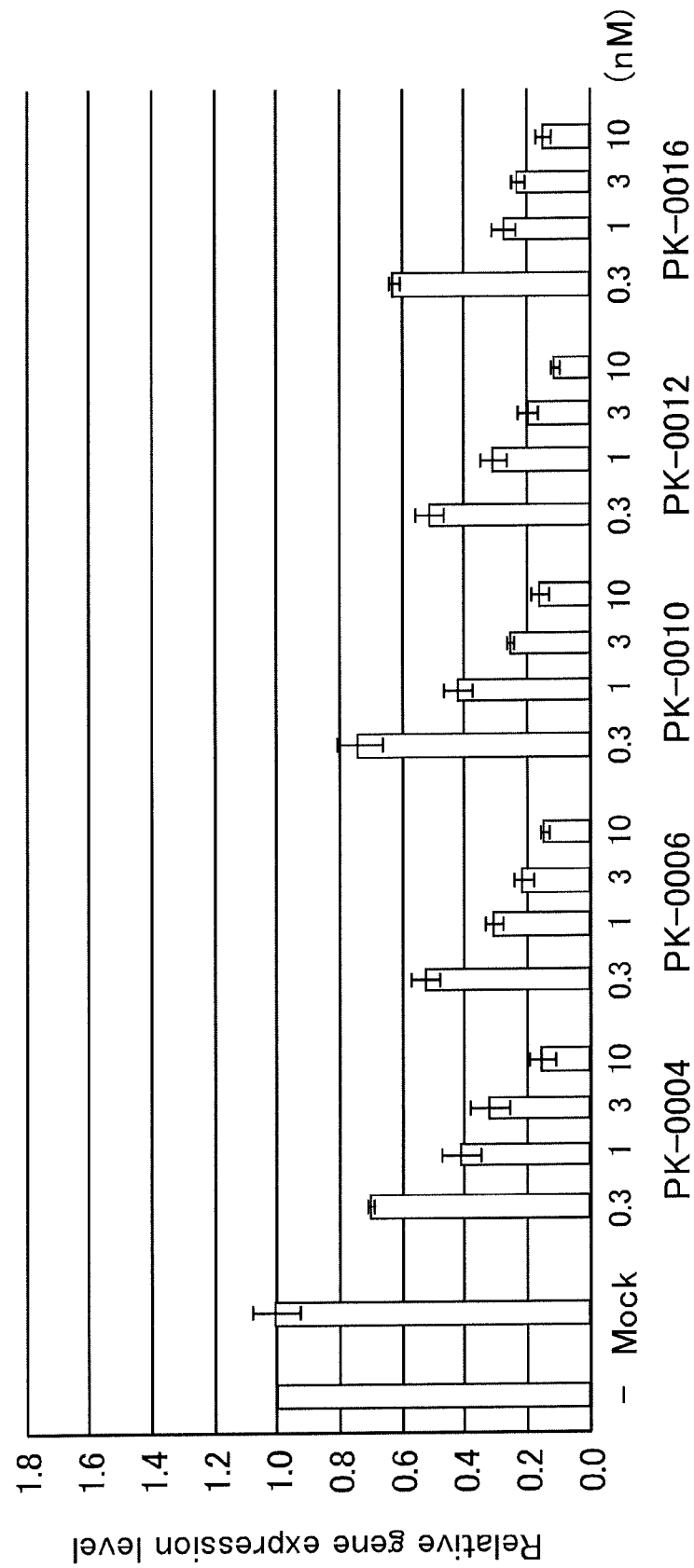
FIG. 10 is a graph showing the relative expression level of the GAPDH gene in HCT116 cells in still another example of the present invention

The results thereof are shown in FIG. 10. FIG. 10 is a graph showing the relative expression level of the GAPDH gene in the HCT116 cells. As can be seen from FIG. 10, it was found that the ssRNAs including proline or prolinol (PK-0004, PK-0006, PK-0010, PK-0012, and PK-0016) each exhibit a potent inhibitory activity, and that they each exhibit the inhibitory activity in a concentration-dependent manner.

Example B8

Inhibitory Effect on the GAPDH Gene Expression in HCT116 Cells

Using ssRNA having undergone substitution with a linker having proline, the inhibitory effect on the GAPDH gene in HCT116 cells was examined.

(1) Materials and Method
(1.1) Solid-Phase Synthesis of ssRNA

As RNA of the present example (Ex ssRNA), the same Ex ssRNA as used in Example B4 was synthesized. The RNA was synthesized in the same manner as in Example B4, unless otherwise stated.

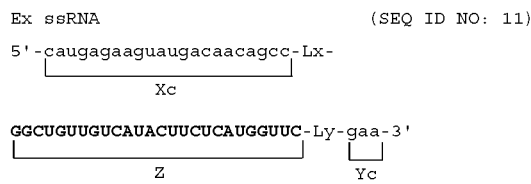

```
Ex ssRNA                               (SEQ ID NO: 11)
5'-caugagaaguaugacaacagcc-Lx-
                          Xc GGCUGUUGCAUACUUCUCAUGGUUC-Ly-gaa-3'
            Z                  Yc
```

As amidites for linker synthesis, D-proline-diamide-amidite (Compound 9 in Scheme 3) synthesized in Example A3-1 and proline-diamide-amidite (type B) (Compound 22 in Scheme 4) synthesized in Example A4 were used. Regarding the thus-synthesized respective RNAs, the amidites used for the synthesis of their linker moieties are shown in the table below.

TABLE 5

| ssRNA | Amidite used in Lx and Ly |
|---|---|
| PK-0034 | D-proline-diamide-amidite (Compound 9 in Scheme 3) |
| PK-0036 | proline-diamide-amidite (type B) (Compound 22 in Scheme 4) |
| PK-0004 | L-proline-diamide-amidite (Compound 10 in Scheme 3) |

(1.2) Inhibition of Gene Expression

Transfection into HCT116 cells, culture, collection of RNA, synthesis of cDNA, and PCR were carried out in the same manner as in Example B4, except that each of the above RNAs wad used, and the relative expression level of the GAPDH gene was determined.

(2) Results

Figure 11:
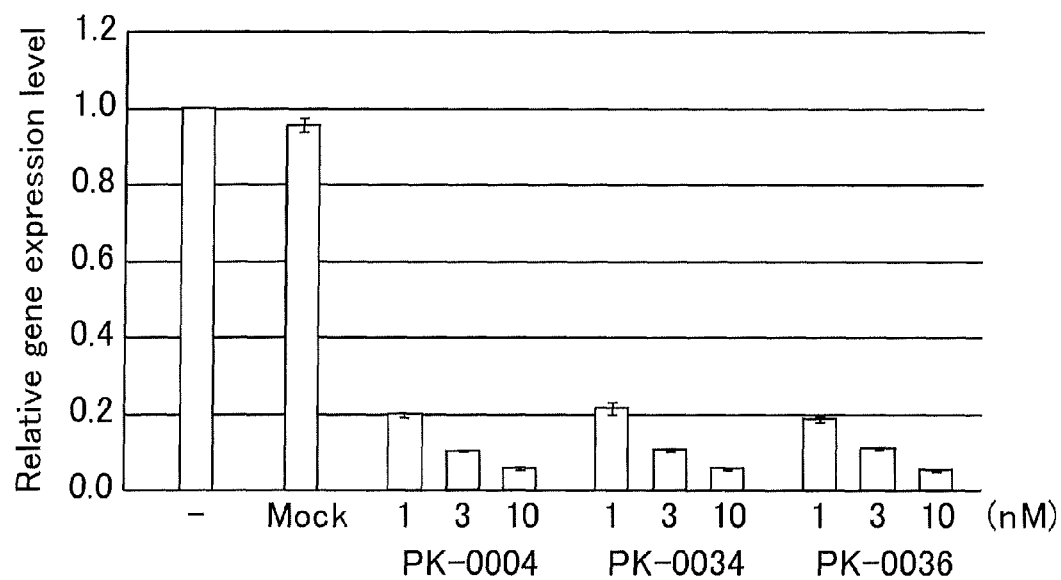
FIG. 11 is a graph showing the relative expression level of the GAPDH gene in HCT116 cells in still another example of the present invention.

The results thereof are shown in FIG. 11. FIG. 11 is a graph showing the relative expression level of the GAPDH gene in the HCT116 cells. As can be seen from FIG. 11, it was found that the ssRNAs including proline (PK-0004, PK-0034, and PK-0036) each exhibit a potent inhibitory activity, and that they each exhibit the inhibitory activity in a concentration-dependent manner.

Example B9

Inhibitory Effect on the TGF-β1 Gene Expression in Vitro

Using ssRNAs having undergone substitution with a linker having proline, the inhibitory effect on the TGF-β1 gene expression in Hepa1-6 cells was examined.

(1) Materials and Method
(1.1) Solid-Phase Synthesis of Ssrna

As RNAs of the present example, PK-0007, PK-0026, PK-0027, and PK-0028 shown below were synthesized. The RNAs were synthesized in the same manner as in Example B4, unless otherwise stated. As amidites for linker synthesis, L-proline-diamide-amidite (Compound 10 in Scheme 3) synthesized in Example A3-1 was used. Each of the RNAs includes the following 21-mer sequence that inhibits the expression of the TGF-β1 gene. This sequence was designed based on the siRNA used by Cheng et al. (*Mol. Pharm.*, 2009, 6, pp. 772-779). In the following sequences, "*" indicates an unpaired base.

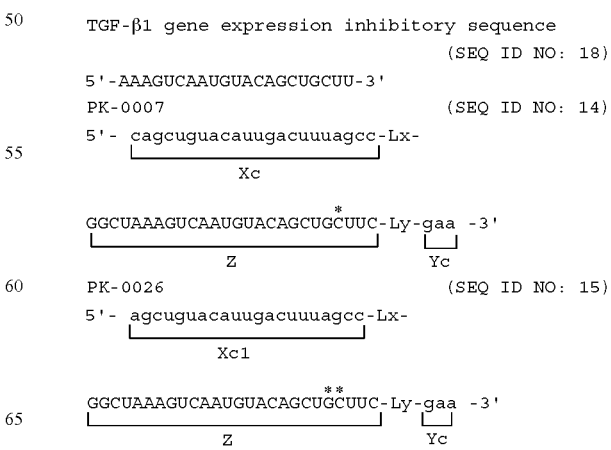

```
TGF-β1 gene expression inhibitory sequence
                                        (SEQ ID NO: 18)
5'-AAAGUCAAUGUACAGCUGCUU-3'
PK-0007                                 (SEQ ID NO: 14)
5'- cagcuguacauugacuuuagcc-Lx-
                         Xc
                                  *
GGCUAAAGUCAAUGUACAGCUGCUUC-Ly-gaa -3'
              Z                    Yc
PK-0026                                 (SEQ ID NO: 15)
5'- agcuguacauugacuuuagcc-Lx-
                         Xc1
                                  **
GGCUAAAGUCAAUGUACAGCUGCUUC-Ly-gaa -3'
              Z                    Yc
```

```
PK-0027                                           (SEQ ID NO: 16)
5'- agcagcuguacauugacuuuagcc-Lx-
    |_____|
               Xc

*
GGCUAAAGUCAAUGUACAGCUGCUUC-Ly-g  -3'
|_____|    |_|
            Z                  Yc

PK-0028                                           (SEQ ID NO: 17)
5'-gcagcuguacauugacuuuagcc-Lx-
   |_____|
             Xc

**
GGCUAAAGUCAAUGUACAGCUGCUUC-Ly-g  -3'
|_____|    |_|
            Z                  Yc
```

(1.2) Inhibition of Gene Expression

RNA solution was prepared by dissolving each of the RNAs that had been cryopreserved in distilled water for injection (Otsuka Pharmaceutical Co., Ltd.) so as to achieve a concentration of 20 μmol/l.

Hepa1-6 cells (The RIKEN BioResource Center) were used as cells, and a 10% FBS-containing DMEM (Invitrogen) was used as a medium. The culture conditions were set to 37° C. and 5% $CO_2$.

First, the Hepa1-6 cells were cultured in the medium, and were dispensed to a 24-well plate so that each well contained 400 μl of the medium to achieve a density of $3 \times 10^4$ cells/well. Then, transfection of the ssRNA to the Hepa1-6 cells, collection of the RNA, and synthesis of cDNA were carried out in the same manner as in Example B4, except that the above RNA solution was used. In the transfection, the final concentration of the RNA in the well was set to 1 nmol/l. Then, PCR was carried out in the same manner as in Example B4, except that the following PCR primer set for the TGF-β1 gene and the following primer set for the β-actin gene were used as primers, and the expression level of the TGF-β1 gene and that of the β-actin gene as an internal standard were measured. The expression level of the TGF-β1 gene was corrected with reference to the expression level of the β-actin gene.

```
PCR Primer set for TGF-β1 gene (SEQ ID NO: 19)
5'-CCATTGCTGTCCCGTGCAGAGCTG-3'

(SEQ ID NO: 20)
5'-ATGGTAGCCCTTGGGCTCGTGGATC-3'

Primer set for β-actin gene (SEQ ID NO: 21)
5'-GTCGTACCACAGGCATTGTGATGG-3'
```

```
                                                  (SEQ ID NO: 22)
5'-GCAATGCCTGGGTACATGGTGG-3'
```

As to each of the control (−) and the control (mock), the gene expression level was measured in the same manner as in Example B4. Then, the corrected expression level of the TGF-β1 gene in the control (−) was set as 1, and that in the cells transfected with each RNA was presented as the relative value to that in the control.

(2) Results

Figure 12:
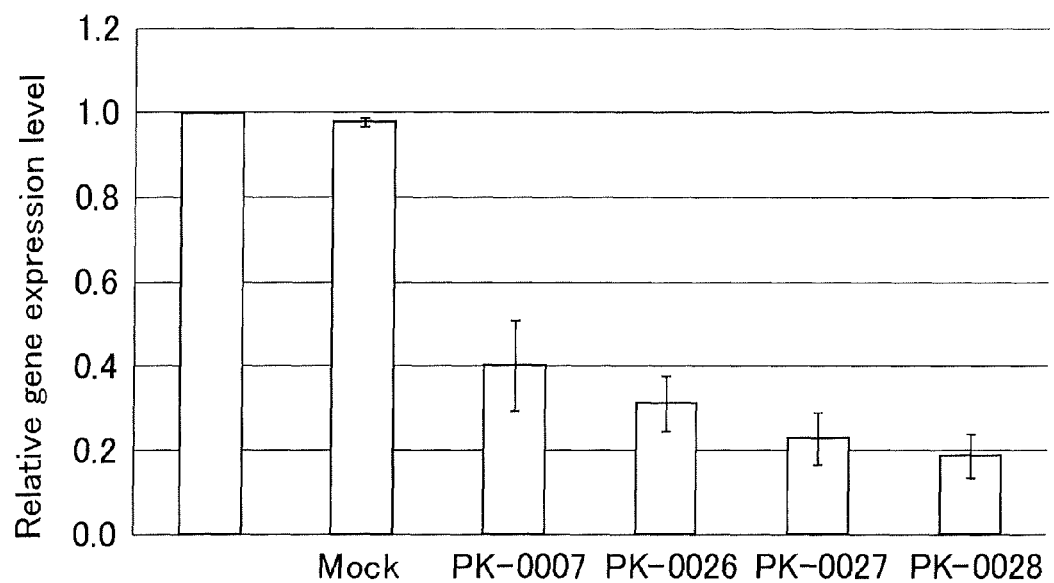
FIG. 12 is a graph showing the relative expression level of the TGF-β1 gene in still another example of the present invention.

The results thereof are shown in FIG. 12. FIG. 12 is a graph showing the relative expression level of the TGF-β1 gene. As can be seen in FIG. 12, the ssRNAs containing proline all exhibited potent inhibitory activities.

Among them, PK-0027 and PK-0028 in which the 2nd base and the 3rd base from the 3' end of the inner region (Z) are the unpaired bases, respectively, exhibited higher inhibitory activities than PK-0007 and PK-0026 in which the 4th base and the 5th base from the 3' end of the inner region (Z) are the unpaired bases, respectively. From these results, it was found that, by settting the position of the unpaired base in the inner region (Z) so as to be closer to the 3' side with respect to the middle of the inner region, it is possible to improve the inhibitory activity. Also, it has already been confirmed that the inhibitory activity can be improved by setting the position of the unpaired base in the inner region (Z) so as to be closer to the 5' side with respect to the middle of the inner region. Such a relationship between the position of the unpaired base and the inhibitory activity exhibited a similar behavior as those exhibited in reference examples to be described below.

Example B10

Inhibitory Effect on the TGF-β1 Gene Expression and Acute Lung Injury in Vivo

Using ssRNA having undergone substitution with a linker having proline, inhibitory effects on the gene expression and the acute lung injury in vivo were examined. These effects were examined according to the method described in Takagi et al. (*J. Thromb Hemost* 2009; 7: pp. 2053-2063).

(B10-1) Inhibitory Effect on the TGF-β1 Gene Expression in Vivo

Using ssRNA having undergone substitution with a linker having proline, the inhibitory effect on the TGF-β1 gene expression in vivo was examined.

(1) Materials and Method
(1.1) Administration of RNAs to Mice with Acute Lung Injury As RNA (Ex) of the present example, ssRNA (PK-0007) of Example B9 was used. Used as RNAs of a comparative example were: ssRNA (PK-0008) as a negative control (Nc); ssRNA (NK-0033) as a positive control (Pc) and ssRNA (NK-0035) as a negative control (Nc) therefor; and dsRNA (NI-0030) as a positive control (Pc) and dsRNA (NI-0031) as a negative control (Nc) therefor, which are all shown below.

```
PK-0007                                                                           (SEQ ID NO 14)

5'-cagcuguacauugacuuuagcc-Lx-GGCUAAAGUCAAUGUACAGCUGCUUC-Ly-gaa-3'
   |_____|    |_____|    |_|
            Xc                           Z                  Yc PK-0008                                                                           (SEQ ID NO 23)

5'-ugucagugcucauuuacaagcc-Lx-GGCUUGUAAAUGAGCACUGACACUUC-Ly-gaa-3'
   |_____|    |_____|    |_|
            Xc                           Z                  Yc
```

-continued

```
NK-0033                                                        (SEQ ID NO: 24)

5'-cagcuguacauugacuuuagccCCACACCGGCUAAAGUCAAUGUACAGCUGCUUCUUCGgaa-3'
   |_____|      |_____||___|
            Xc                              Z                 Yc

NK-0035                                                        (SEQ ID NO: 25)

5'-ugucagugcucauuuacaagccCCACACCGGCUUGUAAAUGAGCACUGACACUUCUUCGgaa-3'
   |_____|      |_____||___|
            Xc                              Z                 Yc

NI-0030

5'-  GCAGCUGUACAUUGACUUUAG-3'    (SEQ ID NO: 26)

3'-UUCGUCGACAUGUAACUGAAA  -5'    (SEQ ID NO: 27)

NI-0031

5'-  GUGUCAGUGCUCAUUUACAAG-3'    (SEQ ID NO: 28)

3'-UUCACAGUCACGAGUAAAUGU  -5'    (SEQ ID NO: 29)
```

RNA solution was prepared by dissolving 100 μg of each of the RNAs in 75 μl of sterile physiological saline. On the other hand, an LPS solution was prepared by dissolving 100 μg of lipopolysaccharide (LPS) in 50 μl of sterile physiological saline.

First, 80 μl of the RNA solution was instilled in tracheae of mice. Then, 1 hour after the instillation, 50 μl of the LPS solution was instilled in the tracheae of the mice to induce lung injury.

As a negative control for the LPS, 50 μl of sterile physiological saline containing no LPS was used instead of the LPS solution. Also, as a negative control for the RNA solution, 80 μl of sterile physiological saline was used.

The administration groups are shown below. In each administration group, four to six mice were used.

Administration group 1:
5 minutes after the administration of 75 μl of sterile physiological saline, 50 μl of sterile physiological saline was administered.

Administration group 2:
5 minutes after the administration of 75 μl of sterile physiological saline, 50 μl of the LPS solution was administered.

Administration group 3:
5 minutes after the administration of 75 μl of the RNA solution (PK-0007), 50 μl of the LPS solution was administered.

Administration group 4:
5 minutes after the administration of 75 μl of the RNA solution (PK-0008), 50 μl of the LPS solution was administered.

Administration group 5:
5 minutes after the administration of 75 μl of the RNA solution (NK-0033), 50 μl of the LPS solution was administered.

Administration group 6:
5 minutes after the administration of 75 μl of the RNA solution (NK-0035), 50 μl of the LPS solution was administered.

Administration group 7:
5 minutes after the administration of 75 μl of the RNA solution (NI-0030), 50 μl of the LPS solution was administered.

Administration group 8:
5 minutes after the administration of 50 μl of the RNA solution (NI-0031), 50 μl of the LPS solution was administered.

(1.2) Sampling of Bronchoalveolar Lavage Fluid (BALF)

24 hours after the instillation of the LPS solution or sterile physiological saline (negative control for LPS), the mice were euthanized by administering an excess of pentobarbital to their abdominal cavities. Their lungs were collected and used as samples.

Regarding each lung sample of the mice, the expression level of the TGF-β1 gene per unit lung weight was measured using a TGF-β1 Quantikine Colorimetric Sandwich ELISA (trade name, R&D Systems).

(2) Results

Figure 13:
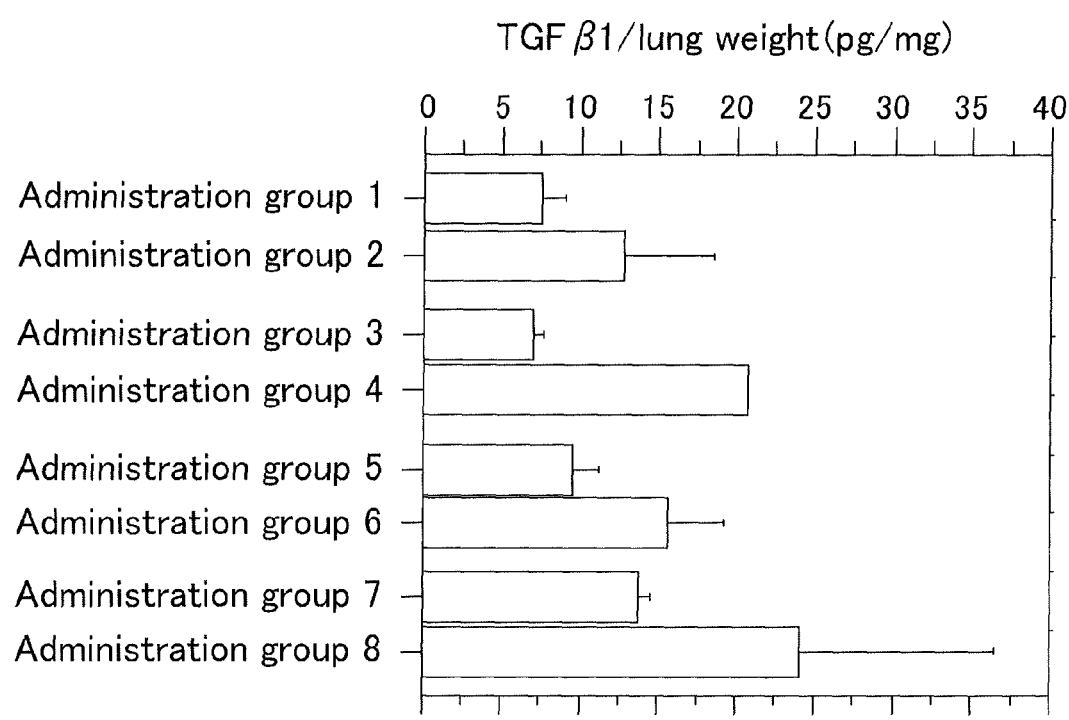
FIG. 13 is a graph showing the expression level of TGF-β1 per unit lung weight in each administration group in still another example of the present invention.

The results thereof are shown in FIG. 13. FIG. 13 is a graph showing the expression level of the TGF-β1 gene per unit lung weight in each administration group, and the horizontal axis indicates the amount of the TGF-β1 protein expressed. In the administration group 3 (LPS(+)/PK-0007 (+)), the expression level of the TGF-β1 gene was inhibited markedly as compared with that in the administration group 2 (LPS (+)/ssRNA (−)). It was found that this inhibitory effect was stronger than those in the administration group 5 (LPS (+)/positive control NK-0033 (+)) and the administration group 7 (LPS (+)/positive control NI-0030). In the administration group 4 (negative control PK-0008 (+)), the administration group 6 (negative control NK-0035 (+)), and the administration group 8 (negative control NI-0031 (+)), no inhibitory effect was observed.

(A10-2) Off-Target Effect In Vivo

Using ssRNA having undergone substitution with a linker having proline, the off-target effect in vivo was examined and the side effect was evaluated.

As RNA of the present example, the ssRNA (PK-0007) of Example B9 was used. As RNA of a comparative example, ssRNA (PK-0008) as an RNAi negative control (Nc) shown in Example A10-1 was used. RNA solution was prepared by dissolving 100 μg of each of the RNAs in 75 μl of sterile physiological saline.

The administration groups are shown below. In each administration group, two to four mice were used.

Administration group 1:
75 μl of sterile physiological saline was administered.

Administration group 2:
75 μl of the RNA solution (PK-0007) was administered.

Administration group 3:
75 μl of the RNA solution (PK-0008) was administered.

Then, 24 hours after the administration, the mice were euthanized in the same manner as in Example B10-1. Blood samples were collected by puncturing the hearts of the mice.

Each blood sample was added to a test tube containing a 3.8% aqueous solution of sodium citrate. The amount (volume) of the aqueous solution of sodium citrate was set to 1/10 of the blood sample. The BALF (bronchoalveolar lavage fluid) sample was collected from this mixture in a manner described in Yasui et al. (Am J Respir Crit. Care Med 2001:163:1660-8). The amounts of TNF-α and IFN-β in the supernatant of the BALF sample were measured The amount of TNF-α and the amount of IFN-β in each supernatant were measured. The amount of TNF-α was quantified using a Mouse TNF set II (trade name, Beckton Dickinson and Company) in accordance with its instructions for use. The amount of IFN-β was quantified using a ELISA plate produced using Rabbit Anti-Mouse Interferon β (trade name, PBL Interferon Source) and Biotin Labeling Kit-NH2 (trade name, Dojindo Laboratories) in accordance with their instructions for use.

Figure 14A:
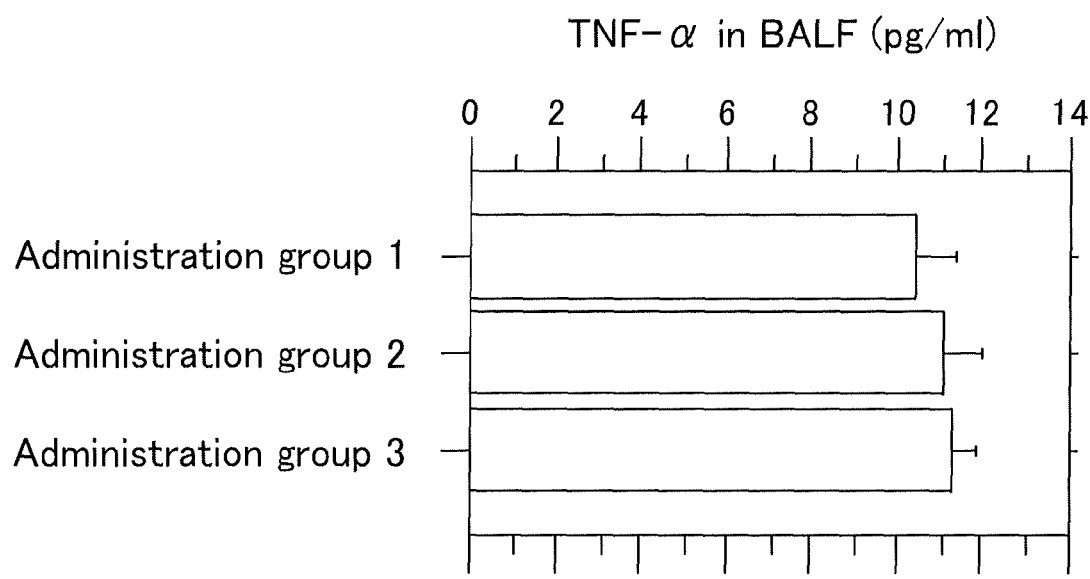
FIG. 14A is a graph showing the amount of TNF-αc in a BALF sample in each administration group in the example of the present invention.
Figure 14B:
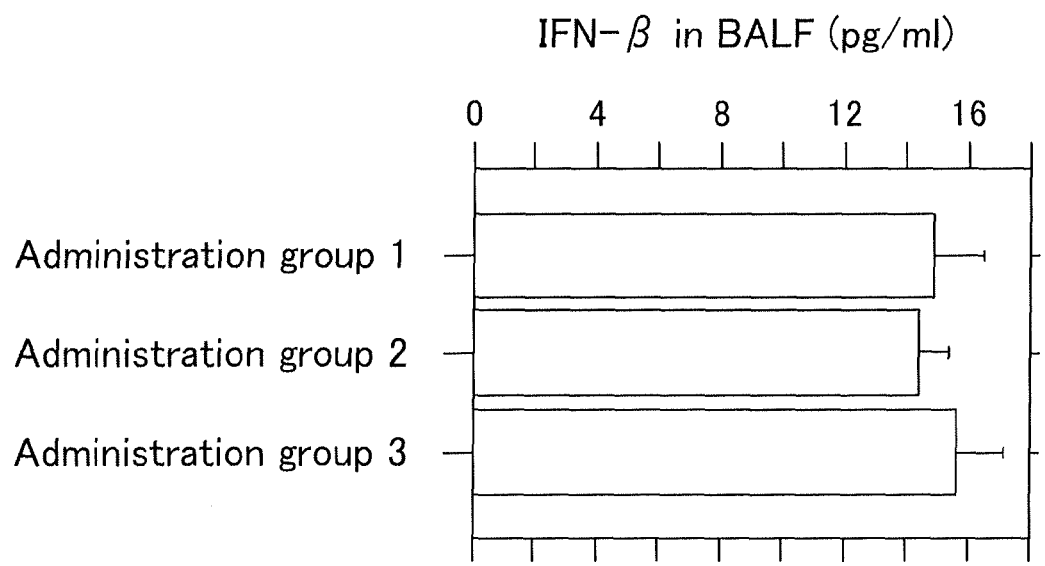
FIG. 14B is a graph showing the amount of IFN-β in a BALF sample in each administration group in the example of the present invention.

The results thereof are shown in FIG. 14. FIG. 14A is a graph showing the amount of TNF-α in the BALF sample in each administration group, and FIG. 14B is a graph showing the amount of IFN-β in the BALF sample in each administration group. In FIGS. 14A and 14B, the horizontal axes indicate the respective amounts. In the administration group 2 (PK-0007 (+)) according to the present example, expressions of TNF-α and IFN-β were not caused, as compared with the administration group 1 (ssRNA (−)).

Example B11

Ribonuclease Resistance

Regarding the ssRNA of the present invention, the resistance to ribonuclease was examined.

(1) Materials and Method

As RNA (Ex) of the present example, ssRNA (PK-0007) of Example B9 was used. Furthermore, as RNA of a comparative example, dsRNA (NI-0030) as a positive control (Pc) shown in Example B10-1 was used.

First, 60 pmol of each of the above RNAs, $5 \times 10^{-5}$ units of RNase A (Roche), and $5 \times 10^{-5}$ units of RNase T1 (trade name, Roche) were mixed with 20 mmol/l Tris-HCl (pH 8), and the resultant mixture was incubated at 37° C. 10 minutes, 20 minutes, and 30 minutes after the start of the incubation, the reaction of the RNases was terminated according to a conventional method. Then, the reaction solution was subjected to electrophoresis using 15% polyacrylamide gel. Thereafter, the gel was stained with SYBR Green II (trade name, Lonza) and then analyzed using an E-BOX-VX$^2$ (trade name, M & S Instruments Inc., Tokyo).

(2) Results

Figure 15:
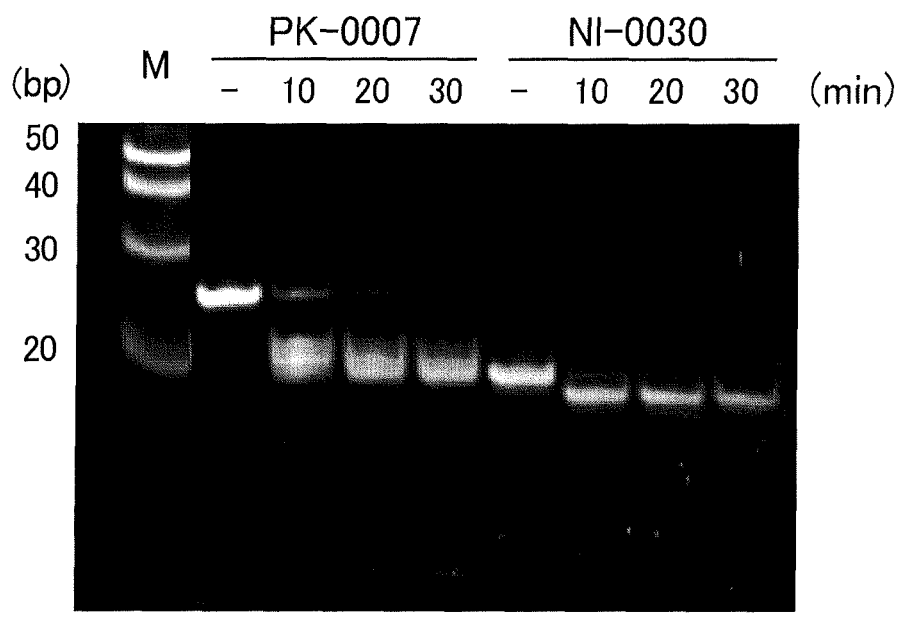
FIG. 15 is an electrophoretogram showing ribonuclease resistance in still another example of the present invention.

The results thereof are shown in FIG. 15. FIG. 15 is an electrophoretogram showing ribonuclease resistance. In FIG. 15, the lane "M" indicates a molecular weight marker, and "(min)" indicates the incubation time.

As can be seen from FIG. 15, NI-0030 of the comparative example composed of a natural nucleotide was degraded almost completely after 10 minutes of incubation. In contrast, PK-0007 of the example still remained even after 10 minutes of incubation. These results demonstrate that the ssRNA of the present invention is superior to dsRNA in ribonuclease resistance.

Example B12

Nuclease Resistance

Regarding the ssRNA of the present invention, the nuclease resistance was examined.

(1) Materials and Method

As RNA (Ex) of the present example, ssRNA (PK-0007) of Example B9 was used. As RNA of a comparative example, dsRNA (NI-0030) as an RNAi positive control (Pc) shown in Example B10-1 was used.

First, 60 pmol of each ssRNA and 0.5 units of S7 nuclease (Roche) were mixed with 50 mmol Tris-HCl (pH8) containing 5 mmol/l $CaCl_2$, and the resultant mixture was incubated at 37° C. 0.5 hours after the start of the incubation (0 h), the reaction of the S7 nuclease was terminated according to a conventional method. Then, the reaction solution was subjected to electrophoresis using 7M urea-15% polyacrylamide gel according to a conventional method. Thereafter, the gel was stained with SYBR Green II (trade name, Lonza) and then analyzed using an E-BOX-VX2 (trade name, M & S Instruments Inc.).

(2) Results

Figure 16:
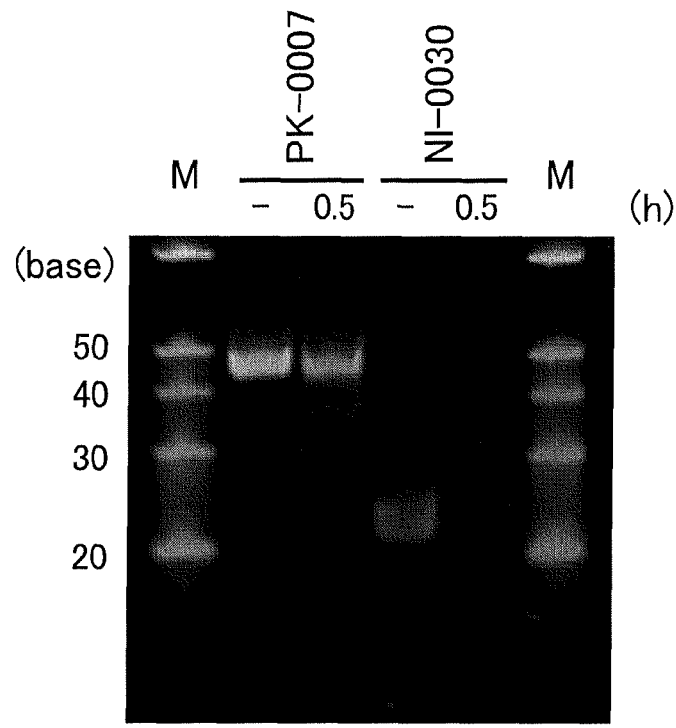
FIG. 16 is an electrophoretogram showing S7 nuclease resistance in still another example of the present invention.

The results thereof are shown in FIG. 16. FIG. 16 is an electrophoretogram showing S7 nuclease resistance. In FIG. 16, the lane "M" indicates a molecular weight marker, and "(h)" indicates the incubation time.

As can be seen from FIG. 16, NI-0030 of the comparative example composed of a natural nucleotide was degraded almost completely after 0.5 hours of incubation. In contrast, PK-0007 of the example still remained even after 0.5 hours of incubation. These results demonstrate that the ssRNA of the present invention is superior to dsRNA in S7 nuclease resistance.

From the respective results obtained in the Examples B, it was found that the ssPN of the present invention can be constructed regardless of the kind of a target gene, for example. Thus, it can be said that the ssPN molecule of the present invention is a novel versatile tool that can be used for inhibiting the expression of a target gene without depending on the kind of the target gene.

Reference Example 1

Using ssRNAs having an unpaired base at different positions, inhibition of the GAPDH gene expression in vitro was examined.

(1) Materials and Method

As RNAs, ssRNAs shown in FIG. 17 were used. In FIG. 17, the numbers on the right indicate sequence identification numbers. In FIG. 17, from the 5' side, a region indicated with underlined lower-case letters is the region (Xc); a region indicated with underlined capital letters is the inner region (Z); and a region indicated with underlined lower-case letters is the region (Yc). A region between Xc and Z is a linker region (Lx), and a region between Z and Yc is a linker region (Ly). Also, "Xc/Yc" indicates the ratio between the base length (Xc) of the region (Xc) and the base length (Yc) of the region (Yc). In FIG. 17, "*" indicates an unpaired base.

In each of the ssRNAs, the base length of the inner region (Z) was set to 26, the base length of the linker region (Lx) was set to 7, and the base length of the linker region (Ly) was set to 4. In NK-0036 and NK-0040, the total number of the bases (Xc+Yc) in the regions (Xc) and (Yc) was set to 26. In the ssRNAs other than NK-0036 and NK-0040, the total number of the bases (Xc+Ye) in the regions (Xc) and (Yc) was set to 25. Then, under these conditions, the base lengths of the regions (Xc) and (Yc) were changed. As a result, NK-0036 and NK-0040 became the molecules without unpaired bases. Furthermore, each of the ssRNAs other than NK-0036 and NK-0040 became the molecule in whcih the inner region (Z) includes only one unpaired base that does not form a double strand and the position of the unpaired base in the inner region (Z) was shifted from the 3' side to the 5' side.

Transfection into the HCT116 cells, culture, collection of RNA, synthesis of cDNA, and PCR were carried out in the same manner as in Example B2, except that each of the above RNAs wad used, and the relative expression level of the GAPDH gene was determined. The RNA concentration at the time of the transfection was set to 10 nmol/l.

(2) Results and Consideration

Figure 18:
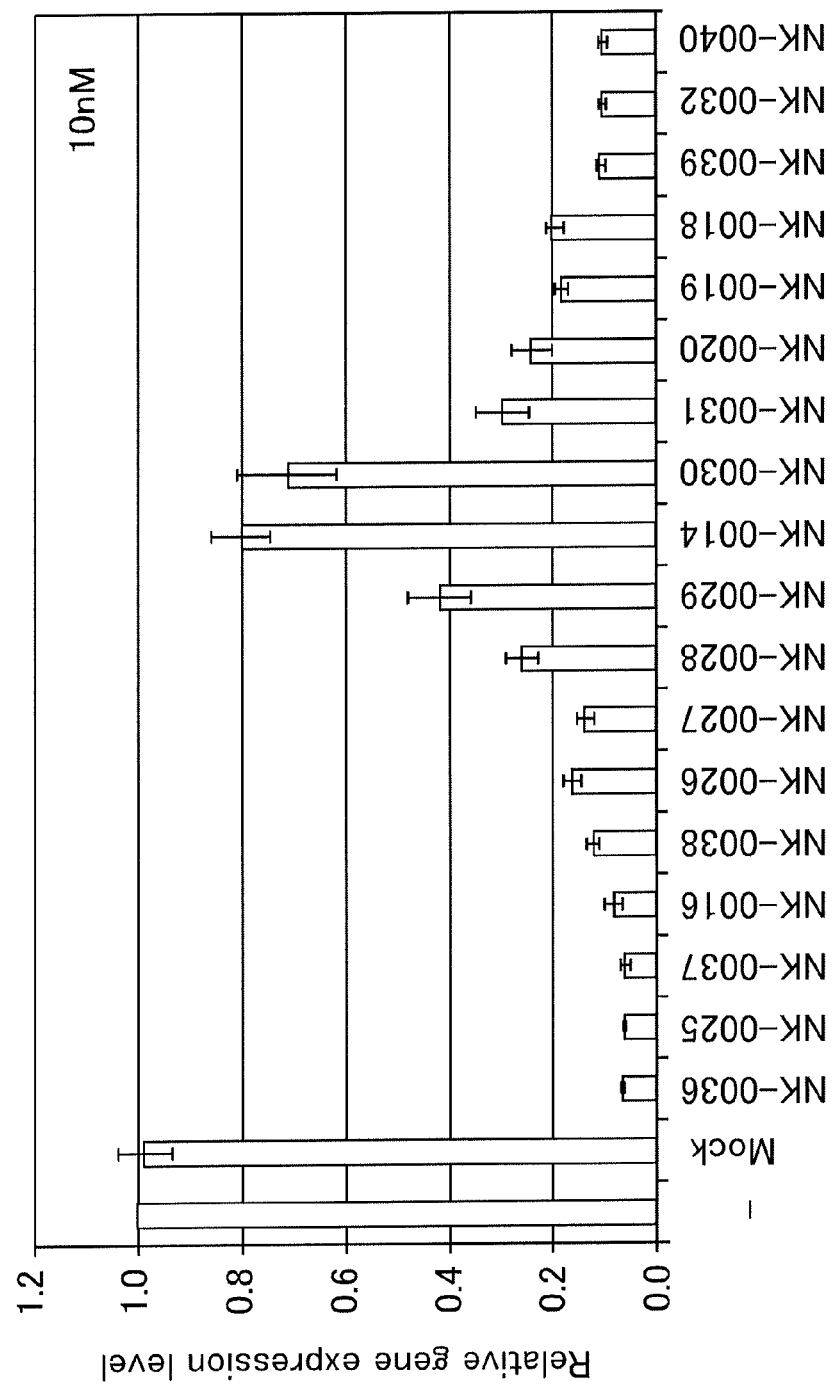
FIG. 18 is a graph showing the relative expression level of the GAPDH gene in the reference example.

The results thereof are shown in FIG. 18. FIG. 18 is a graph showing the relative expression level of the GAPDH gene when each of the RNAs was used at the final concentration of 10 nmol/l. As can be seen from FIG. 18, it was found that all the ssRNAs with the varied lengths of the 5' side region (Xc) and the 3' side region (Yc) inhibited the expression of the GAPDH gene.

In particular, it was found that, as the difference between the base length of the region (Xc) and the base length of the region (Yc) became greater, the expression level of the gene decreased relatively, i.e., the inhibitory activity increased. That is, it was found that, by setting the position of the unpaired base in the inner region (Z) so as to be closer to the 5' side or the 3' side with respect to the middle of the inner region, it is possible to improve the inhibitory activity.

Reference Example 2

Using ssRNAs having an unpaired base at different positions, inhibition of the TGF-β1 gene expression in vitro was examined.

(1) Materials and Method

As RNAs, ssRNAs shown below were used. In the following sequences, "*" indicates an unpaired base.

NK-0033 (SEQ ID NO: 49)

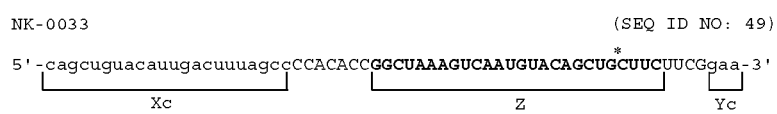

NK-0061 (SEQ ID NO: 50)

NK-0055 (SEQ ID NO: 51)

NK-0062 (SEQ ID NO: 52)

(1.2) Inhibition of Gene Expression

RNA solution was prepared by dissolving each of the RNAs that had been cryopreserved in distilled water for injection so as to achieve a concentration of 20 μmol/l. Then, transfection of the ssRNA to the Hepa1-6 cells, collection of RNA, synthesis of cDNA, PCR, and determination of the relative expression level of the TGF-β1 gene were carried out in the same manner as in Example B9, except that the above RNA solution was used. The RNA concentration at the time of the transfection was set to 1 nmol/l.

(2) Results

Figure 19:
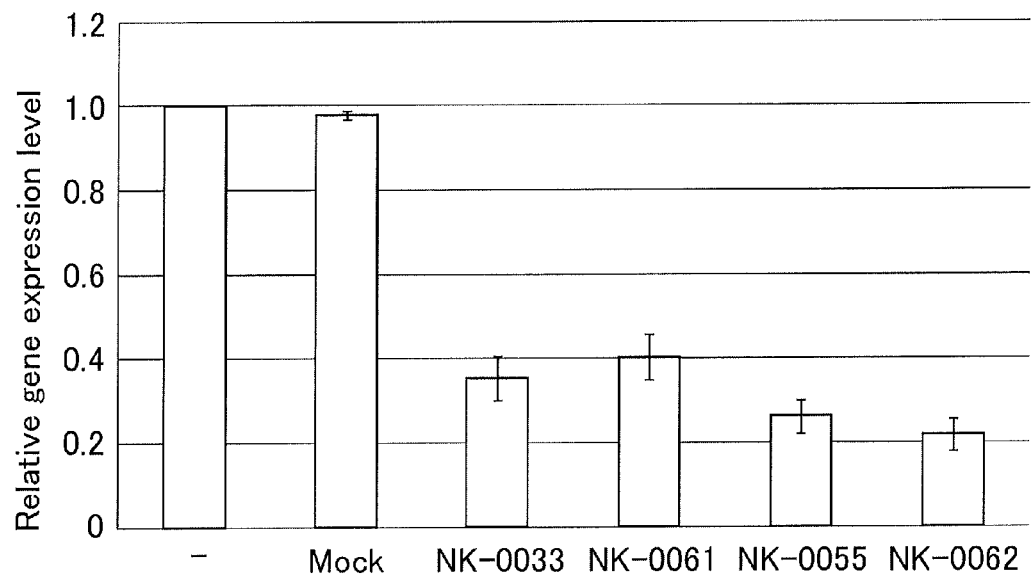
FIG. 19 is a graph showing the relative expression level of the TGF-β1 gene in another reference example.

The results thereof are shown in FIG. 19. FIG. 19 is a graph showing the relative expression level of the TGF-β1 gene. As can be seen from FIG. 19, these ssRNAs all exhibited inhibitory activities. Furthermore, NK-0055 and NK-0062 in which the 2nd base and the 3rd base from the 3' end of the inner region (Z) are the unpaired bases, respectively, exhibited higher inhibitory activities than NK-0033 and NK-0061 in which the 4th base and the 5th base from the 3' end of the inner region (Z) are the unpaired bases, respectively. These results agree with the behavior exhibited in Reference Example 1 directed to the different target gene.

Reference Example 3

Using ssRNAs having an unpaired base at different positions, inhibition of the LAMA1 gene expression in vitro was examined.

(1) Materials and Method

As RNAs, the following ssRNAs were used. In the following sequences, "*" indicates an unpaired base.

```
Primer set for LAMA1 gene
                                            (SEQ ID NO: 55)
5'-AAAGCTGCCAATGCCCCTCGACC-3'

(SEQ ID NO: 56)
5'-TAGGTGGGTGGCCCTCGTCTTG-3'
```

Regarding the control 1 (−) and the control 2 (mock), the expression amounts also were measured in the same manner as in Example B2. Then, the corrected expression level of the LAMA1 gene in the control (−) was set as 1, and that in the cells transfected with each RNA was presented as the relative value to that in the control.

(2) Results

Figure 20:
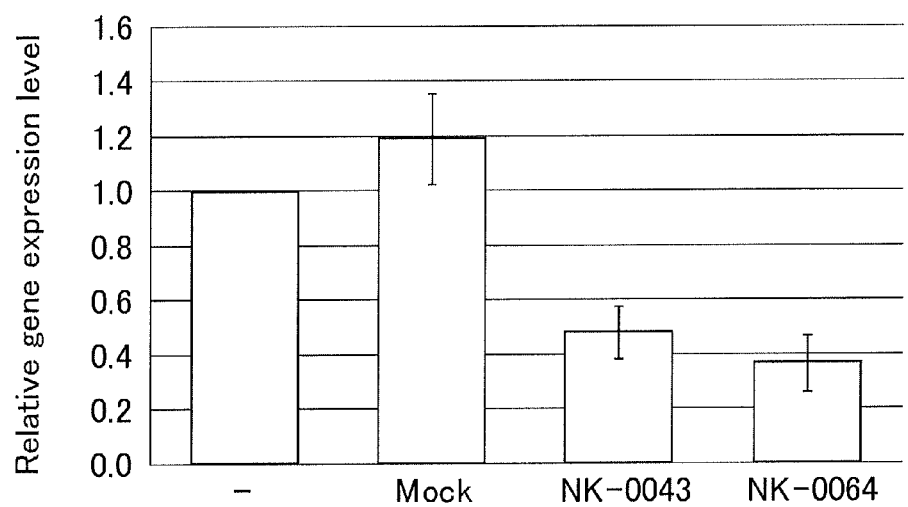
FIG. 20 is a graph showing the relative expression level of the LAMA1 gene in still another reference example.

The results thereof are shown in FIG. 20. FIG. 20 is a graph showing the relative expression level of the LAMA1 gene in the 293 cells. As can be seen from FIG. 20, these ssRNAs all exhibited inhibitory activities. Furthermore, NK-0064 in which the 2nd base from the 3' end of the inner region (Z) is the unpaired base exhibited a higher inhibitory activity than NK-0043 in which the 4th base from the 3' end of the inner region (Z) is the unpaired base. These results agree with the behaviors exhibited in Reference Examples 1 and 2 directed to different target genes.

Transfection to 293 cells was carried out in the same manner as in Example B6, except that each of the above RNAs was used, and the cells were cultured for 48 hours. The RNA concentration at the time of the transfection was set to 10 nmol/l. Then, collection of RNA, synthesis of cDNA, and PCR were carried out in the same manner as in Example B2, except that a primer set for the LAMA1 gene shown below was used, and the expression level of the LAMA1 gene and the that of the β-actin gene as an internal standard were measured. The expression level of the LAMA1 gene was corrected with reference to that of the G-actin gene as the internal standard.

Reference Example 4

Using ssRNAs having an unpaired base at different positions, inhibition of the LMNA gene expression in vitro was examined.

(1) Materials and Method

As RNAs, the following ssRNAs were used. In the following sequences, "*" indicates an unpaired base.

Transfection to A549 cells was carried out in the same manner as in Example B6, except that each of the above RNAs was used, and the cells were cultured for 48 hours. The RNA concentration at the time of the transfection was set to 3 nmol/l. Then, collection of RNA, synthesis of cDNA, and PCR were carried out in the same manner as in Example B2, except that a primer set for the LMNA gene shown below were used as a primer, and the expression level of the LMNA gene and that of the β-actin gene as an internal standard were measured. The expression level of the LMNA gene was corrected with reference to that of the β-actin gene as the internal standard.

```
Primer set for LMNA gene
                                      (SEQ ID NO: 59)
5'-CTGGACATCAAGCTGGCCCTGGAC-3'

(SEQ ID NO: 60)
5'-CACCAGCTTGCGCATGGCCACTTC-3'
```

Figure 21:
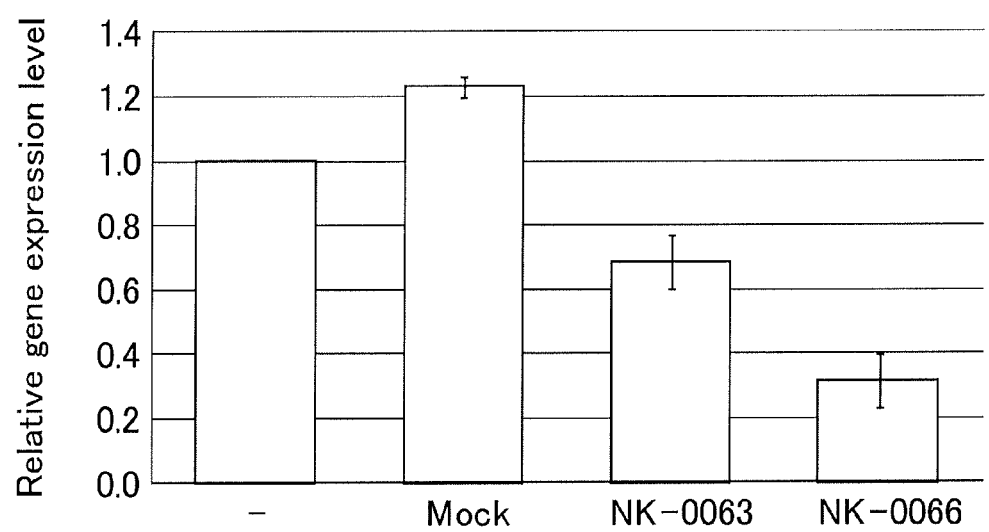
FIG. 21 is a graph showing the relative expression level of the LMNA gene in still another reference example.

Regarding the control 1 (−) and the control 2 (mock), the expression amounts also were measured in the same manner as in Example B2. Then, the corrected expression level of the LMNA gene in the control (−) was set as 1, and that in the cells transfected with each RNA was presented as the relative value to that in the control (2) Results The results thereof are shown in FIG. 21. FIG. 21 is a graph showing the relative expression level of the LMNA gene in the A549 cells. As can be seen from FIG. 21, these ssRNAs all exhibited inhibitory activities. Furthermore, NK-0066 in which the 2nd base from the 3' end of the inner region (Z) is the unpaired base exhibited a higher inhibitory activity than NK-0063 in which the 4th base from the 3' end of the inner region (Z) is the unpaired base. These results agree with the behaviors exhibited in Reference Examples 1 to 3 directed to different target genes.

From the results obtained in Reference Examples 1 to 4, it is clear that, for example, regarding the position of the unpaired base, similar behaviors are exhibited regardless of the kind of a target gene and an expression inhibitory sequence for the target gene. Furthermore, it has already been described above that Example B9 exhibited a similar behavior to those of the reference examples.

Reference Example 5

Using ssRNAs with the length of each of the inner 5' side region (X), the 5' side region (Xc), the inner 3' side region (Y), and the 3' side region (Yc) being varied, inhibition of the GAPDH gene expression in vitro was examined.

(1) Materials and Method

As RNAs, ssRNAs shown in FIG. 22 were used. In FIG. 22, the numbers on the right indicate sequence identification numbers. In FIG. 22, from the 5' side, a region indicated with underlined lower-case letters is the region (Xc); a region indicated with underlined capital letters is the inner region (Z); and a region indicated with underlined lower-case letters is the region (Yc). Also, "Xc+Yc/X+Y" indicates the ratio between the total base length of the regions (Xc) and (Yc) and the total base length of the regions (X) and (Y). In FIG. 22, "*" indicates an unpaired base.

In each of the ssRNAs, the base length of the linker region (Lx) was set to 7, the base length of the linker region (Ly) was set to 4, the base length of the region (Yc) was set to 1, and the 2nd base from the 3' side of the inner region (Z) was set to be an unpaired base. Then, the base length of the inner region (Z) and the base length of the region (Xc) were changed.

Unless otherwise stated, transfection of each of the RNAs into HCT116 cells, culture, collection of the RNA, synthesis of cDNA, and PCR were carried out in the same manner as in Example B2, and the relative expression level of the GAPDH gene was calculated. The transfection was carried out by setting the composition per well to be the same as that shown in Table 2 in Example B4.

(2) Results and Consideration

Figure 23:
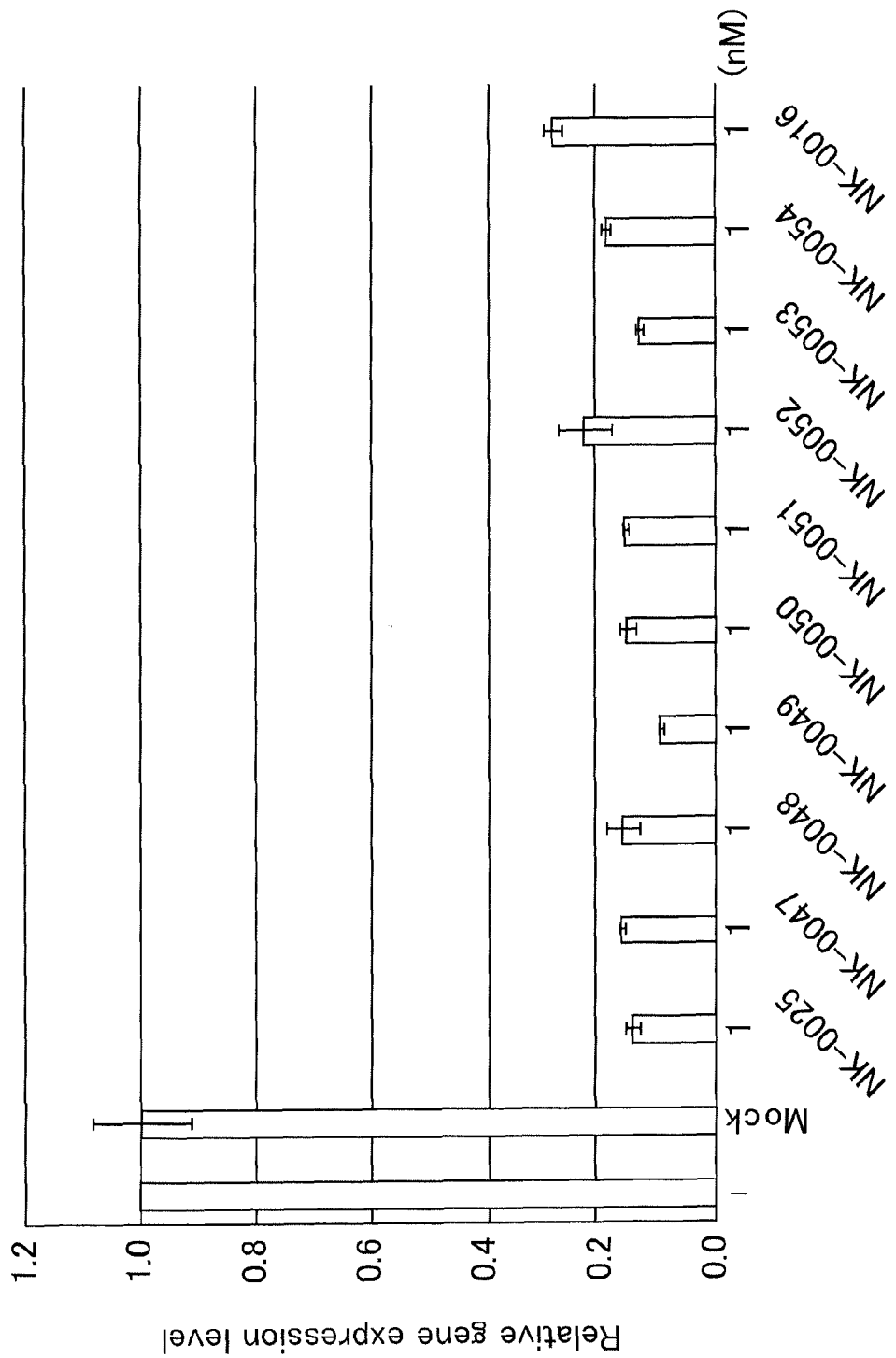
FIG. 23 is a graph showing the relative expression level of the GAPDH gene in the reference example.

The results thereof are shown in FIG. 23. FIG. 23 is a graph showing the relative expression level of the GAPDH gene when each of the RNAs was used at the final concentration of 1 nmol/l. As can be seen from FIG. 23, it was found that all the ssRNAs having various lengths of the regions (X), (Xc), (Y), and (Yc) inhibited the expression of the GAPDH gene.

While the present invention has been described above with reference to illustrative embodiments and examples, the present invention is by no means limited thereto. Various changes and modifications that may become apparent to those skilled in the art may be made in the configuration and specifics of the present invention without departing from the scope of the present invention.

This application claims priority from: Japanese Patent Application No. 2010-174915 filed on Aug. 3, 2010; Japanese Patent Application No. 2010-230806 filed on Oct. 13, 2010; Japanese Patent Application No. 2010-269823 filed on Dec. 2, 2010; and Japanese Patent Application No. 2011-152381 filed on Jul. 8, 2011. The entire disclosures of these Japanese Patent Applications are incorporated herein by reference.

INDUSTRIAL APPLICABILITY

According to the ssPN molecule of the present invention, it is possible to inhibit the expression of a gene. Furthermore, since the ssPN molecule is not circular, it can be synthesized easily. Also, since the ssPN molecule is a single strand, an annealing step as required in the production of a double strand is not necessary, so that it can be produced efficiently. Moreover, since the linker region includes the non-nucleotide residue(s), not only conventional alterations to nucleotide residues, for example, but also alterations such as modification in the linker region become possible, for example. As described above, since the ssPN molecule of the present invention can inhibit the expression of a target gene, it is useful as, for example, a pharmaceutical, a diagnostic agent, an agricultural chemical, and a tool for conducting research on agricultural chemicals, medical science, life science, and the like.

[Sequence Listing]

TF11004WO.ST25.txt

SEQUENCE LISTING

```
<160> NUMBER OF SEQ ID NOS: 69

<210> SEQ ID NO 1
<211> LENGTH: 25
<212> TYPE: RNA
<213> ORGANISM: Artificial
<220> FEATURE:
```

```
<223> OTHER INFORMATION: nucleic acid molecule

<400> SEQUENCE: 1
ggcuguuguc auacuucuca ugguu                                          25

<210> SEQ ID NO 2
<211> LENGTH: 23
<212> TYPE: RNA
<213> ORGANISM: Artificial
<220> FEATURE:
<223> OTHER INFORMATION: nucleic acid molecule

<400> SEQUENCE: 2
ccaugagaag uaugacaaca gcc                                            23

<210> SEQ ID NO 3
<211> LENGTH: 48
<212> TYPE: RNA
<213> ORGANISM: Artificial
<220> FEATURE:
<223> OTHER INFORMATION: nucleic acid molecule

<400> SEQUENCE: 3
ccaugagaag uaugacaaca gccggcuguu gucauacuuc ucaugguu                 48

<210> SEQ ID NO 4
<211> LENGTH: 19
<212> TYPE: RNA
<213> ORGANISM: Artificial
<220> FEATURE:
<223> OTHER INFORMATION: nucleic acid molecule

<400> SEQUENCE: 4
guugucauac uucucaugg                                                 19

<210> SEQ ID NO 5
<211> LENGTH: 55
<212> TYPE: RNA
<213> ORGANISM: Artificial
<220> FEATURE:
<223> OTHER INFORMATION: nucleic acid molecule

<400> SEQUENCE: 5
ccaugagaag uaugacaaca gccccacacc ggcuguuguc auacuucuca ugguu         55

<210> SEQ ID NO 6
<211> LENGTH: 19
<212> TYPE: RNA
<213> ORGANISM: Artificial
<220> FEATURE:
<223> OTHER INFORMATION: nucleic acid molecule

<400> SEQUENCE: 6
auuguaacga gacaaacac                                                 19

<210> SEQ ID NO 7
<211> LENGTH: 23
<212> TYPE: DNA
<213> ORGANISM: Artificial
<220> FEATURE:
<223> OTHER INFORMATION: primer

<400> SEQUENCE: 7
ggagaaggct ggggctcatt tgc                                            23

<210> SEQ ID NO 8
```

```
<211> LENGTH: 23
<212> TYPE: DNA
<213> ORGANISM: Artificial
<220> FEATURE:
<223> OTHER INFORMATION: primer

<400> SEQUENCE: 8
tggccagggg tgctaagcag ttg                                              23

<210> SEQ ID NO 9
<211> LENGTH: 23
<212> TYPE: DNA
<213> ORGANISM: Artificial
<220> FEATURE:
<223> OTHER INFORMATION: primer

<400> SEQUENCE: 9
gccacggctg cttccagctc ctc                                              23

<210> SEQ ID NO 10
<211> LENGTH: 25
<212> TYPE: DNA
<213> ORGANISM: Artificial
<220> FEATURE:
<223> OTHER INFORMATION: primer

<400> SEQUENCE: 10
aggtctttgc ggatgtccac gtcac                                            25

<210> SEQ ID NO 11
<211> LENGTH: 51
<212> TYPE: RNA
<213> ORGANISM: Artificial
<220> FEATURE:
<223> OTHER INFORMATION: nucleic acid molecule

<400> SEQUENCE: 11
caugagaagu augacaacag ccggcuguug ucauacuucu caugguucga a               51

<210> SEQ ID NO 12
<211> LENGTH: 51
<212> TYPE: RNA
<213> ORGANISM: Artificial
<220> FEATURE:
<223> OTHER INFORMATION: nucleic acid molecule

<400> SEQUENCE: 12
ccaucaacga uaagugaaag ccggcuuuca cuuaucguug auggcuucga a               51

<210> SEQ ID NO 13
<211> LENGTH: 62
<212> TYPE: RNA
<213> ORGANISM: Artificial
<220> FEATURE:
<223> OTHER INFORMATION: nucleic acid molecule

<400> SEQUENCE: 13
caugagaagu augacaacag ccccacaccg gcuguuguca uacuucucau gguucuucgg      60
aa                                                                     62

<210> SEQ ID NO 14
<211> LENGTH: 51
<212> TYPE: RNA
<213> ORGANISM: Artificial
<220> FEATURE:
<223> OTHER INFORMATION: nucleic acid molecule
```

<400> SEQUENCE: 14
cagcuguaca uugacuuuag ccggcuaaag ucaauguaca gcugcuucga a                51

<210> SEQ ID NO 15
<211> LENGTH: 50
<212> TYPE: RNA
<213> ORGANISM: Artificial
<220> FEATURE:
<223> OTHER INFORMATION: nucleic acid molecule

<400> SEQUENCE: 15
agcuguacau ugacuuuagc cggcuaaagu caauguacag cugcuucgaa                 50

<210> SEQ ID NO 16
<211> LENGTH: 51
<212> TYPE: RNA
<213> ORGANISM: Artificial
<220> FEATURE:
<223> OTHER INFORMATION: nucleic acid molecule

<400> SEQUENCE: 16
agcagcugua cauugacuuu agccggcuaa agucaaugua cagcugcuuc g               51

<210> SEQ ID NO 17
<211> LENGTH: 50
<212> TYPE: RNA
<213> ORGANISM: Artificial
<220> FEATURE:
<223> OTHER INFORMATION: nucleic acid molecule

<400> SEQUENCE: 17
gcagcuguac auugacuuua gccggcuaaa gucaauguac agcugcuucg                 50

<210> SEQ ID NO 18
<211> LENGTH: 21
<212> TYPE: RNA
<213> ORGANISM: Artificial
<220> FEATURE:
<223> OTHER INFORMATION: nucleic acid molecule

<400> SEQUENCE: 18
aaagucaaug uacagcugcu u                                                21

<210> SEQ ID NO 19
<211> LENGTH: 24
<212> TYPE: DNA
<213> ORGANISM: Artificial
<220> FEATURE:
<223> OTHER INFORMATION: primer

<400> SEQUENCE: 19
ccattgctgt cccgtgcaga gctg                                             24

<210> SEQ ID NO 20
<211> LENGTH: 25
<212> TYPE: DNA
<213> ORGANISM: Artificial
<220> FEATURE:
<223> OTHER INFORMATION: primer

<400> SEQUENCE: 20
atggtagccc ttgggctcgt ggatc                                            25

<210> SEQ ID NO 21
<211> LENGTH: 24
<212> TYPE: DNA

```
<213> ORGANISM: Artificial
<220> FEATURE:
<223> OTHER INFORMATION: primer

<400> SEQUENCE: 21
gtcgtaccac aggcattgtg atgg                                              24

<210> SEQ ID NO 22
<211> LENGTH: 22
<212> TYPE: DNA
<213> ORGANISM: Artificial
<220> FEATURE:
<223> OTHER INFORMATION: primer

<400> SEQUENCE: 22
gcaatgcctg ggtacatggt gg                                                22

<210> SEQ ID NO 23
<211> LENGTH: 51
<212> TYPE: RNA
<213> ORGANISM: Artificial
<220> FEATURE:
<223> OTHER INFORMATION: nucleic acid molecule

<400> SEQUENCE: 23
ugucagugcu cauuuacaag ccggcuugua aaugagcacu gacacuucga a                51

<210> SEQ ID NO 24
<211> LENGTH: 62
<212> TYPE: RNA
<213> ORGANISM: Artificial
<220> FEATURE:
<223> OTHER INFORMATION: nucleic acid molecule

<400> SEQUENCE: 24
cagcuguaca uugacuuuag ccccacaccg gcuaaaguca auguacagcu gcuucuucgg       60
aa                                                                      62

<210> SEQ ID NO 25
<211> LENGTH: 62
<212> TYPE: RNA
<213> ORGANISM: Artificial
<220> FEATURE:
<223> OTHER INFORMATION: nucleic acid molecule

<400> SEQUENCE: 25
ugucagugcu cauuuacaag ccccacaccg gcuuguaaau gagcacugac acuucuucgg       60
aa                                                                      62

<210> SEQ ID NO 26
<211> LENGTH: 21
<212> TYPE: RNA
<213> ORGANISM: Artificial
<220> FEATURE:
<223> OTHER INFORMATION: sense

<400> SEQUENCE: 26
gcagcuguac auugacuuua g                                                 21

<210> SEQ ID NO 27
<211> LENGTH: 21
<212> TYPE: RNA
<213> ORGANISM: Artificial
<220> FEATURE:
<223> OTHER INFORMATION: antisense
```

```
<400> SEQUENCE: 27
aaagucaaug uacagcugcu u                                          21

<210> SEQ ID NO 28
<211> LENGTH: 21
<212> TYPE: RNA
<213> ORGANISM: Artificial
<220> FEATURE:
<223> OTHER INFORMATION: sense

<400> SEQUENCE: 28
gugucagugc ucauuuacaa g                                          21

<210> SEQ ID NO 29
<211> LENGTH: 21
<212> TYPE: RNA
<213> ORGANISM: Artificial
<220> FEATURE:
<223> OTHER INFORMATION: antisense

<400> SEQUENCE: 29
uguaaaugag cacugacacu u                                          21

<210> SEQ ID NO 30
<211> LENGTH: 19
<212> TYPE: RNA
<213> ORGANISM: Artificial
<220> FEATURE:
<223> OTHER INFORMATION: nucleic acid molecule

<400> SEQUENCE: 30
uugcgcuuuu uggugacgc                                             19

<210> SEQ ID NO 31
<211> LENGTH: 62
<212> TYPE: RNA
<213> ORGANISM: Artificial
<220> FEATURE:
<223> OTHER INFORMATION: nucleic acid molecule

<400> SEQUENCE: 31
aaccaugaga aguaugacaa cagccccaca ccggcuguug ucauacuucu caugguucuu    60
cg                                                                  62

<210> SEQ ID NO 32
<211> LENGTH: 62
<212> TYPE: RNA
<213> ORGANISM: Artificial
<220> FEATURE:
<223> OTHER INFORMATION: nucleic acid molecule

<400> SEQUENCE: 32
accaugagaa guaugacaac agccccacac cggcuguugu cauacuucuc augguucuuc    60
gg                                                                  62

<210> SEQ ID NO 33
<211> LENGTH: 62
<212> TYPE: RNA
<213> ORGANISM: Artificial
<220> FEATURE:
<223> OTHER INFORMATION: nucleic acid molecule

<400> SEQUENCE: 33
ccaugagaag uaugacaaca gccccacacc ggcuguuguc auacuucuca ugguucuucg    60
```

```
ga                                                               62

<210> SEQ ID NO 34
<211> LENGTH: 62
<212> TYPE: RNA
<213> ORGANISM: Artificial
<220> FEATURE:
<223> OTHER INFORMATION: nucleic acid molecule

<400> SEQUENCE: 34
caugagaagu augacaacag ccccacaccg gcuguuguca uacuucucau gguucuucgg   60
aa                                                               62

<210> SEQ ID NO 35
<211> LENGTH: 62
<212> TYPE: RNA
<213> ORGANISM: Artificial
<220> FEATURE:
<223> OTHER INFORMATION: nucleic acid molecule

<400> SEQUENCE: 35
augagaagua ugacaacagc cccacaccgg cuguugucau acuucucaug guucuucgga   60
ac                                                               62

<210> SEQ ID NO 36
<211> LENGTH: 62
<212> TYPE: RNA
<213> ORGANISM: Artificial
<220> FEATURE:
<223> OTHER INFORMATION: nucleic acid molecule

<400> SEQUENCE: 36
ugagaaguau gacaacagcc ccacaccggc uguugucaua cuucucaugg uucuucggaa   60
cc                                                               62

<210> SEQ ID NO 37
<211> LENGTH: 62
<212> TYPE: RNA
<213> ORGANISM: Artificial
<220> FEATURE:
<223> OTHER INFORMATION: nucleic acid molecule

<400> SEQUENCE: 37
agaaguauga caacagcccc acaccggcug uugucauacu ucucaugguu cuucggaacc   60
au                                                               62

<210> SEQ ID NO 38
<211> LENGTH: 62
<212> TYPE: RNA
<213> ORGANISM: Artificial
<220> FEATURE:
<223> OTHER INFORMATION: nucleic acid molecule

<400> SEQUENCE: 38
aaguaugaca acagccccac accggcuguu gucauacuuc ucaugguucu ucggaaccau   60
ga                                                               62

<210> SEQ ID NO 39
<211> LENGTH: 62
<212> TYPE: RNA
<213> ORGANISM: Artificial
<220> FEATURE:
<223> OTHER INFORMATION: nucleic acid molecule
```

```
<400> SEQUENCE: 39
guaugacaac agccccacac cggcuguugu cauacuucuc augguucuuc ggaaccauga    60
ga                                                                  62

<210> SEQ ID NO 40
<211> LENGTH: 62
<212> TYPE: RNA
<213> ORGANISM: Artificial
<220> FEATURE:
<223> OTHER INFORMATION: nucleic acid molecule

<400> SEQUENCE: 40
augacaacag ccccacaccg gcuguuguca uacuucucau gguucuucgg aaccaugaga    60
ag                                                                  62

<210> SEQ ID NO 41
<211> LENGTH: 62
<212> TYPE: RNA
<213> ORGANISM: Artificial
<220> FEATURE:
<223> OTHER INFORMATION: nucleic acid molecule

<400> SEQUENCE: 41
acaacagccc cacaccggcu guugucauac uucucauggu ucuucggaac caugagaagu    60
au                                                                  62

<210> SEQ ID NO 42
<211> LENGTH: 62
<212> TYPE: RNA
<213> ORGANISM: Artificial
<220> FEATURE:
<223> OTHER INFORMATION: nucleic acid molecule

<400> SEQUENCE: 42
aacagcccca caccggcugu ugucauacuu cucaugguuc uucggaacca ugagaaguau    60
ga                                                                  62

<210> SEQ ID NO 43
<211> LENGTH: 62
<212> TYPE: RNA
<213> ORGANISM: Artificial
<220> FEATURE:
<223> OTHER INFORMATION: nucleic acid molecule

<400> SEQUENCE: 43
cagccccaca ccggcuguug ucauacuucu caugguucuu cggaaccaug agaaguauga    60
ca                                                                  62

<210> SEQ ID NO 44
<211> LENGTH: 62
<212> TYPE: RNA
<213> ORGANISM: Artificial
<220> FEATURE:
<223> OTHER INFORMATION: nucleic acid molecule

<400> SEQUENCE: 44
agccccacac cggcuguugu cauacuucuc augguucuuc ggaaccauga gaaguaugac    60
aa                                                                  62

<210> SEQ ID NO 45
<211> LENGTH: 62
<212> TYPE: RNA
```

<213> ORGANISM: Artificial
<220> FEATURE:
<223> OTHER INFORMATION: nucleic acid molecule

<400> SEQUENCE: 45
gccccacacc ggcuguuguc auacuucuca ugguucuucg aaccaugag aaguaugaca    60
ac                                                                  62

<210> SEQ ID NO 46
<211> LENGTH: 62
<212> TYPE: RNA
<213> ORGANISM: Artificial
<220> FEATURE:
<223> OTHER INFORMATION: nucleic acid molecule

<400> SEQUENCE: 46
ccccacaccg gcuguguca uacuucucau gguucuucgg aaccaugaga aguaugacaa    60
ca                                                                  62

<210> SEQ ID NO 47
<211> LENGTH: 62
<212> TYPE: RNA
<213> ORGANISM: Artificial
<220> FEATURE:
<223> OTHER INFORMATION: nucleic acid molecule

<400> SEQUENCE: 47
cccacaccgg cuguugucau acuucucaug guucuucgga accaugagaa guaugacaac    60
ag                                                                  62

<210> SEQ ID NO 48
<211> LENGTH: 62
<212> TYPE: RNA
<213> ORGANISM: Artificial
<220> FEATURE:
<223> OTHER INFORMATION: nucleic acid molecule

<400> SEQUENCE: 48
ccacaccggc uguugucaua cuucucaugg uucuucggaa ccaugagaag uaugacaaca    60
gc                                                                  62

<210> SEQ ID NO 49
<211> LENGTH: 62
<212> TYPE: RNA
<213> ORGANISM: Artificial
<220> FEATURE:
<223> OTHER INFORMATION: nucleic acid molecule

<400> SEQUENCE: 49
cagcuguaca uugacuuuag ccccacaccg gcuaaaguca auguacagcu gcuucuucgg    60
aa                                                                  62

<210> SEQ ID NO 50
<211> LENGTH: 61
<212> TYPE: RNA
<213> ORGANISM: Artificial
<220> FEATURE:
<223> OTHER INFORMATION: nucleic acid molecule

<400> SEQUENCE: 50
agcuguacau ugacuuuagc cccacaccgg cuaaagucaa uguacagcug cuucuucgga    60
a                                                                   61

<210> SEQ ID NO 51
<211> LENGTH: 62
<212> TYPE: RNA
<213> ORGANISM: Artificial
<220> FEATURE:
<223> OTHER INFORMATION: nucleic acid molecule

<400> SEQUENCE: 51
agcagcugua cauugacuuu agccccacac cggcuaaagu caauguacag cugcuucuuc    60
gg    62

<210> SEQ ID NO 52
<211> LENGTH: 61
<212> TYPE: RNA
<213> ORGANISM: Artificial
<220> FEATURE:
<223> OTHER INFORMATION: nucleic acid molecule

<400> SEQUENCE: 52
gcagcuguac auugacuuua gccccacacc ggcuaaaguc aauguacagc ugcuucuucg    60
g    61

<210> SEQ ID NO 53
<211> LENGTH: 62
<212> TYPE: RNA
<213> ORGANISM: Artificial
<220> FEATURE:
<223> OTHER INFORMATION: nucleic acid molecule

<400> SEQUENCE: 53
uguuugucuc guuacaauau ccccacaccg gauauuguaa cgagacaaac acuccuucgg    60
ga    62

<210> SEQ ID NO 54
<211> LENGTH: 62
<212> TYPE: RNA
<213> ORGANISM: Artificial
<220> FEATURE:
<223> OTHER INFORMATION: nucleic acid molecule

<400> SEQUENCE: 54
aguguuuguc ucguuacaau auccccacac cggauauugu aacgagacaa acacuccuuc    60
gg    62

<210> SEQ ID NO 55
<211> LENGTH: 23
<212> TYPE: DNA
<213> ORGANISM: Artificial
<220> FEATURE:
<223> OTHER INFORMATION: primer

<400> SEQUENCE: 55
aaagctgcca atgcccctcg acc    23

<210> SEQ ID NO 56
<211> LENGTH: 22
<212> TYPE: DNA
<213> ORGANISM: Artificial
<220> FEATURE:
<223> OTHER INFORMATION: primer

<400> SEQUENCE: 56
taggtgggtg gccctcgtct tg    22

```
<210> SEQ ID NO 57
<211> LENGTH: 62
<212> TYPE: RNA
<213> ORGANISM: Artificial
<220> FEATURE:
<223> OTHER INFORMATION: nucleic acid molecule

<400> SEQUENCE: 57
cgucaccaaa aagcgcaauu ccccacaccg gaauugcgcu uuuggugac gcuucuucgg    60 aa                                                                 62

<210> SEQ ID NO 58
<211> LENGTH: 62
<212> TYPE: RNA
<213> ORGANISM: Artificial
<220> FEATURE:
<223> OTHER INFORMATION: nucleic acid molecule

<400> SEQUENCE: 58
agcgucacca aaaagcgcaa uuccccacac cggaauugcg cuuuuuggug acgcuucuuc    60
gg                                                                  62

<210> SEQ ID NO 59
<211> LENGTH: 24
<212> TYPE: DNA
<213> ORGANISM: Artificial
<220> FEATURE:
<223> OTHER INFORMATION: primer

<400> SEQUENCE: 59
ctggacatca agctggccct ggac                                          24

<210> SEQ ID NO 60
<211> LENGTH: 24
<212> TYPE: DNA
<213> ORGANISM: Artificial
<220> FEATURE:
<223> OTHER INFORMATION: primer

<400> SEQUENCE: 60
caccagcttg cgcatggcca cttc                                          24

<210> SEQ ID NO 61
<211> LENGTH: 64
<212> TYPE: RNA
<213> ORGANISM: Artificial
<220> FEATURE:
<223> OTHER INFORMATION: nucleic acid molecule

<400> SEQUENCE: 61
aaccaugaga aguaugacaa cagccccaca ccggcuguug ucauacuucu caugguucgu    60
ucgc                                                                64

<210> SEQ ID NO 62
<211> LENGTH: 62
<212> TYPE: RNA
<213> ORGANISM: Artificial
<220> FEATURE:
<223> OTHER INFORMATION: nucleic acid molecule

<400> SEQUENCE: 62
accaugagaa guaugacaac agccccacac cggcuguugu cauacuucuc augguucuuc    60
gg                                                                  62
```

<210> SEQ ID NO 63
<211> LENGTH: 60
<212> TYPE: RNA
<213> ORGANISM: Artificial
<220> FEATURE:
<223> OTHER INFORMATION: nucleic acid molecule

<400> SEQUENCE: 63
accaugagaa guaugacaac agcccacacc gcuguuguca uacuucucau gguucuucgg    60

<210> SEQ ID NO 64
<211> LENGTH: 58
<212> TYPE: RNA
<213> ORGANISM: Artificial
<220> FEATURE:
<223> OTHER INFORMATION: nucleic acid molecule

<400> SEQUENCE: 64
ccaugagaag uaugacaaca gcccacaccg cuguugucau acuucucaug guuucga    58

<210> SEQ ID NO 65
<211> LENGTH: 58
<212> TYPE: RNA
<213> ORGANISM: Artificial
<220> FEATURE:
<223> OTHER INFORMATION: nucleic acid molecule

<400> SEQUENCE: 65
accaugagaa guaugacaac agccacaccc uguugucaua cuucucaugg uucuucgg    58

<210> SEQ ID NO 66
<211> LENGTH: 56
<212> TYPE: RNA
<213> ORGANISM: Artificial
<220> FEATURE:
<223> OTHER INFORMATION: nucleic acid molecule

<400> SEQUENCE: 66
ccaugagaag uaugacaaca gccacacccu guugucauac uucucauggu uuucga    56

<210> SEQ ID NO 67
<211> LENGTH: 54
<212> TYPE: RNA
<213> ORGANISM: Artificial
<220> FEATURE:
<223> OTHER INFORMATION: nucleic acid molecule

<400> SEQUENCE: 67
caugagaagu augacaacag ccacacccug uugcauacu ucucaugguu ucga    54

<210> SEQ ID NO 68
<211> LENGTH: 54
<212> TYPE: RNA
<213> ORGANISM: Artificial
<220> FEATURE:
<223> OTHER INFORMATION: nucleic acid molecule

<400> SEQUENCE: 68
ccaugagaag uaugacaaca ccacaccugu ugcauacuu cucaugguuu ucga    54

<210> SEQ ID NO 69
<211> LENGTH: 52
<212> TYPE: RNA
<213> ORGANISM: Artificial
<220> FEATURE:
<223> OTHER INFORMATION: nucleic acid molecule

```
<400> SEQUENCE: 69
caugagaagu augacaacac cacaccuguu gucauacuuc ucaugguuuc ga            52
```

The invention claimed is:

1. A single-stranded nucleic acid molecule comprising:
an expression inhibitory sequence that inhibits expression of a target gene, wherein
the single-stranded nucleic acid molecule comprises: a region (X); a linker region (Lx); a region (Xc), a region (Y); a region (Yc); and a linker region (Ly) linked between the region (Y) and the region (Yc), the 5' end and the 3' end of the single-stranded nucleic acid molecule are not linked to each other,
the linker region (Lx) is linked between the regions (X) and (Xc),
the region (X) and the region (Y) are linked to each other,
an inner region (Z) consists of the region (X) and the region (Y), and has 19 to 30 bases,
the region (Xc) is complementary to the region (X), and has 1 to 29 bases,
the region (Yc) is complementary to the region (Y), and has 1 to 29 bases,
the inner region (Z) comprises the expression inhibitory sequence, the expression inhibitory sequence is a ribonucleic acid (RNA) molecule, and
the linker region (Lx) comprises a non-nucleotide structure comprising at least one of a pyrrolidine skeleton and a piperidine skeleton.

2. The single-stranded nucleic acid molecule according to claim 1, wherein the linker region (Lx) is represented by the following formula (I):

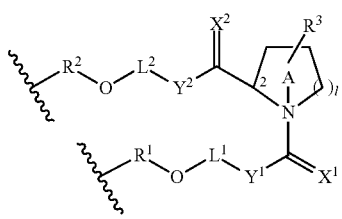

where:
X$^1$ and X$^2$ are each independently H$_2$, O, S, or NH;
Y$^1$ and Y$^2$ are each independently a single bond, CH$_2$, NH, O, or S;
R$^3$ is a hydrogen atom or substituent that is bound to C-3, C-4, C-5, or C-6 on a ring A;
L$^1$ is an alkylene chain composed of n atoms, and a hydrogen atom on an alkylene carbon atom may or may not be substituted with OH, OR$^a$, NH$_2$, NHR$^a$, NR$^a$R$_b$, SH, or SR$^a$, or,
L$^1$ is a polyether chain obtained by substituting at least one carbon atom on the alkylene chain with an oxygen atom, provided that: when Y$^1$ is NH, O, or S, an atom bound to Y$^1$ in L$^1$ is carbon, an atom bound to OR$^1$ in L$^1$ is carbon, and oxygen atoms are not adjacent to each other;
L$^2$ is an alkylene chain composed of m atoms, and a hydrogen atom on an alkylene carbon atom may or may not be substituted with OH, OR$^c$, NH$_2$, NHR$^c$, NR$^c$R$^d$, SH, or SR$^c$, or L$^2$ is a polyether chain obtained by substituting at least one carbon atom on the alkylene chain with an oxygen atom, provided that: when Y$^2$ is NH, O, or S, an atom bound to Y$^2$ in L$^2$ is carbon, an atom bound to OR$^2$ in L$^2$ is carbon, and oxygen atoms are not adjacent to each other;
R$^a$, R$^b$, R$^c$, and R$^d$ are each independently a substituent or a protecting group;
l is 1 or 2;
m is an integer in the range from 0 to 30;
n is an integer in the range from 0 to 30;
on the ring A, one carbon atom other than C-2 may be substituted with nitrogen, oxygen, or sulfur;
the ring A may comprise a carbon-carbon double bond or a carbon-nitrogen double bond;
the regions (Xc) and (X) are each linked to the linker region (Lx) via —OR$^1$— or —OR$^2$—; and
R$^1$ and R$^2$ may or may not be present, and when they are present, R$^1$ and R$^2$ are each independently a nucleotide residue or the structure of the formula (I).

3. The single-stranded nucleic acid molecule according to claim 1, wherein the number of bases (X) in the region (X) and the number of bases (Xc) in the 5' side region (Xc) satisfy a condition of Expression (3) or (5):

$$X > Xc \quad (3)$$

$$X = Xc \quad (5).$$

4. The single-stranded nucleic acid molecule according to claim 3, wherein the number of bases (X) in the region (X) and the number of bases (Xc) in the 5' side region (Xc) satisfy a condition of Expression (11):

$$X - Xc = 1, 2, \text{ or } 3 \quad (11).$$

5. The single-stranded nucleic acid molecule according to claim 1, wherein
the linker region (Ly) comprises a non-nucleotide structure comprising at least one of a pyrrolidine skeleton and a piperidine skeleton.

6. The single-stranded nucleic acid molecule according to claim 5, wherein the linker region (Ly) is represented by the following formula (I):

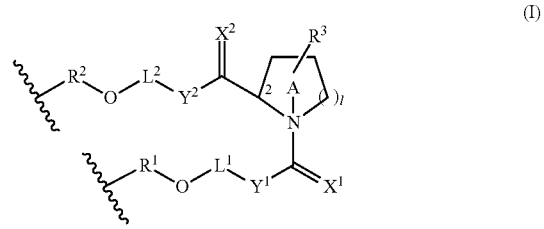

where:
X$^1$ and X$^2$ are each independently H$_2$, O, S, or NH;
Y$^1$ and Y$^2$ are each independently a single bond, CH$_2$, NH, O, or S;
R$^3$ is a hydrogen atom or substituent that is bound to C-3, C-4, C-5, or C-6 on a ring A;

L¹ is an alkylene chain composed of n atoms, and a hydrogen atom on an alkylene carbon atom may or may not be substituted with OH, OR$^a$, NH$_2$, NHR$^a$, NR$^a$R$^b$, SH, or SR$^a$, or, L¹ is a polyether chain obtained by substituting at least one carbon atom on the alkylene chain with an oxygen atom, provided that: when Y¹ is NH, O, or S, an atom bound to Y¹ in L¹ is carbon, an atom bound to OR¹ in L¹ is carbon, and oxygen atoms are not adjacent to each other;

L² is an alkylene chain composed of m atoms, and a hydrogen atom on an alkylene carbon atom may or may not be substituted with OH, OR$^c$, NH$_2$, NHR$^c$, NR$^c$R$^d$, SH, or SR$^c$, or L² is a polyether chain obtained by substituting at least one carbon atom on the alkylene chain with an oxygen atom, provided that: when Y² is NH, O, or S, an atom bound to Y² in L² is carbon, an atom bound to OR² in L² is carbon, and oxygen atoms are not adjacent to each other;

R$^a$, R$^b$, R$^c$, and R$^d$ are each independently a substituent or a protecting group;

l is 1 or 2;
m is an integer in the range from 0 to 30;
n is an integer in the range from 0 to 30;
on the ring A, one carbon atom other than C-2 may be substituted with nitrogen, oxygen, or sulfur;
the ring A may comprise a carbon-carbon double bond or a carbon-nitrogen double bond;
the regions (Xc) and (X) are each linked to the linker region (Lx) via —OR¹— or —OR²—; and
R¹ and R² may or may not be present, and when they are present, R¹ and R² are each independently a nucleotide residue or the structure of the formula (I).

7. The single-stranded nucleic acid molecule according to claim 6, wherein
linking of the regions (Xc) and (X) to the structure of the linker region (Lx) represented by the formula (I), and
linking of the regions (Yc) and (Y) to the structure of the linker region (Ly) represented by the formula (I) satisfy any one of conditions (1) to (4):

Condition (1):
the regions (Xc) and (X) are linked to the structure of the formula (I) via —OR²— and —OR¹—, respectively; and
the regions (Yc) and (Y) are linked to the structure of the formula (1) via —OR¹— and —OR²—, respectively, Condition (2):
the regions (Xc) and (X) are linked to the structure of the formula (I) via —OR²— and —OR¹—, respectively; and
the regions (Yc) and (Y) are linked to the structure of the formula (I) via —OR²— and —OR¹—, respectively, Condition (3):
the regions (Xc) and (X) are linked to the structure of the formula (I) via —OR¹— and —OR²—, respectively; and
the regions (Yc) and (Y) are linked to the structure of the formula (I) via —OR¹— and —OR²—, respectively, Condition (4):
the regions (Xc) and (X) are linked to the structure of the formula (I) via —OR¹— and —OR²—, respectively; and
the regions (Yc) and (Y) are linked to the structure of the formula (I) via —OR²— and —OR¹—, respectively.

8. The single-stranded nucleic acid molecule according to claim 2, wherein, in the formula (I), L¹ is the polyether chain, and the polyether chain is polyethylene glycol.

9. The single-stranded nucleic acid molecule according to claim 2, wherein, in the formula (I), the total (m+n) of the number of atoms (n) in L¹ and the number of atoms (m) in L² is in the range from 0 to 30.

10. The single-stranded nucleic acid molecule according to claim 2, wherein
the structure of the formula (I) is any one of the following formulae (I-1) to (I-9), and
in the formulae (I-1) to (I-9), n is an integer from 0 to 30, m is an integer from 0 to 30, and q is an integer from 0 to 10:

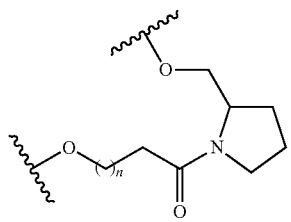
(I-1)

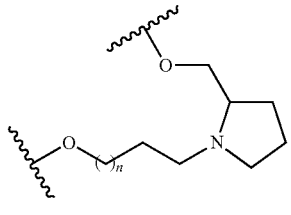
(I-2)

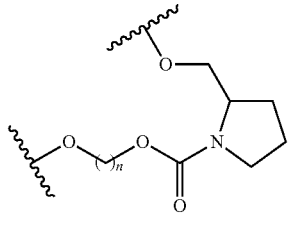
(I-3)

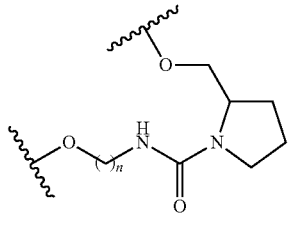
(I-4)

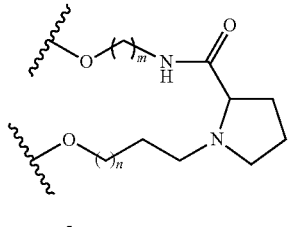
(I-5)

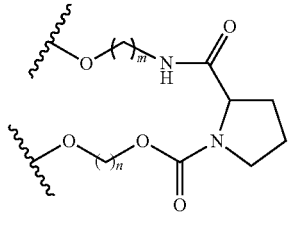
(I-6)

-continued

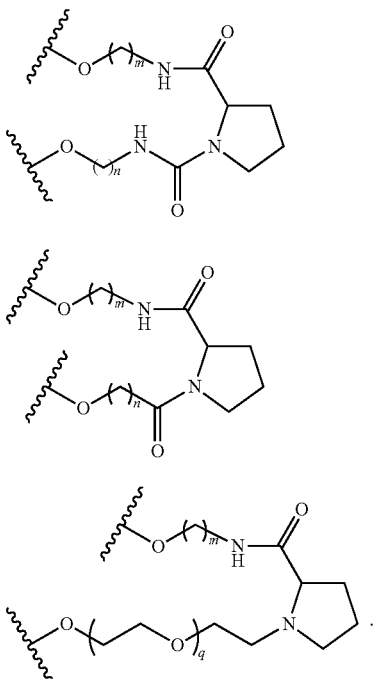

(I-7)

(I-8)

(I-9)

11. The single-stranded nucleic acid molecule according to claim 10, wherein:
in the formula (I-1), n=8;
in the formula (I-2), n=3;
in the formula (I-3), n=4 or 8;
the formula (I-4), n=7 or 8;
in the formula (I-5), n=3 and m=4;
in the formula (I-6), n=8 and m=4;
in the formula (I-7), n=8 and m=4;
in the formula (I-8), n=5 and m=4; and
in the formula (I-9), q=1 and m=4.

12. The single-stranded nucleic acid molecule according to claim 11, wherein the formula (I-4) is the following formula (I-4-a), and the formula (I-8) is the following formula (I-8a):

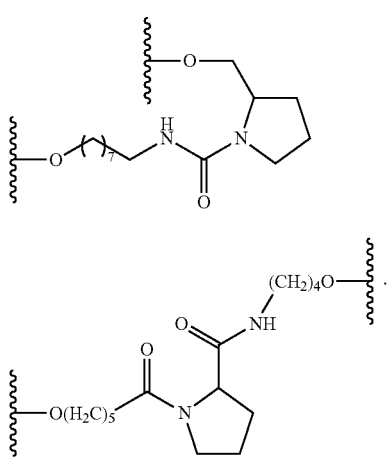

(I-4a)

(I-8a)

13. The single-stranded nucleic acid molecule according to claim 1, wherein the number of bases (X) in the region (X), the number of bases (Y) in the region (Y), the number of bases (Xc) in the region (Xc), and the number of bases (Yc) in the region (Yc) satisfy a condition of Expression (2):

$$Z > Xc + Yc \quad (2).$$

14. The single-stranded nucleic acid molecule according to claim 1, wherein the number of bases (X) in the region (X), the number of bases (Xc) in the region (Xc), the number of bases (Y) in the region (Y), and the number of bases (Yc) in the region (Yc) satisfy any one of conditions (a) to (d):

(a) Conditions of Expressions (3) and (4) are satisfied;

$$X > Xc \quad (3)$$

$$Y = Yc \quad (4)$$

(b) Conditions of Expressions (5) and (6) are satisfied;

$$X = Xc \quad (5)$$

$$Y > Yc \quad (6)$$

(c) Conditions of Expressions (7) and (8) are satisfied;

$$X > Xc \quad (7)$$

$$Y > Yc \quad (8)$$

(d) Conditions of Expressions (9) and (10) are satisfied;

$$X = Xc \quad (9)$$

$$Y = Yc \quad (10).$$

15. The single-stranded nucleic acid molecule according to claim 14, wherein, in the conditions (a) to (d), the difference between the number of bases (X) in the region (X) and the number of bases (Xc) in the region (Xc), and the difference between the number of bases (Y) in the region (Y) and the number of bases (Yc) in the region (Yc) satisfy the following conditions:

(a) Conditions of Expressions (11) and (12) are satisfied;

$$X - Xc = 1, 2, \text{ or } 3 \quad (11)$$

$$Y - Yc = 0 \quad (12)$$

(b) Conditions of Expressions (13) and (14) are satisfied;

$$X - Xc = 0 \quad (13)$$

$$Y - Yc = 1, 2, \text{ or } 3 \quad (14)$$

(c) Conditions of Expressions (15) and (16) are satisfied;

$$X - Xc = 1, 2, \text{ or } 3 \quad (15)$$

$$Y - Yc = 1, 2, \text{ or } 3 \quad (16)$$

(d) Conditions of Expressions (17) and (18) are satisfied;

$$X - Xc = 0 \quad (17)$$

$$Y - Yc = 0 \quad (18).$$

16. The single-stranded nucleic acid molecule according to claim 1, wherein the number of bases (Xc) in the region (Xc) is 1 to 11.

17. The single-stranded nucleic acid molecule according to claim 16, wherein the number of bases (Xc) in the region (Xc) is 1 to 7.

18. The single-stranded nucleic acid molecule according to claim 16, wherein the number of bases (Xc) in the region (Xc) is 1 to 3.

19. The single-stranded nucleic acid molecule according to claim 1, wherein the number of bases (Yc) in the region (Yc) is 1 to 11.

20. The single-stranded nucleic acid molecule according to claim 19, wherein the number of bases (Yc) in the region (Yc) is 1 to 7.

21. The single-stranded nucleic acid molecule according to claim 19, wherein the number of bases (Yc) in the region (Yc) is 1 to 3.

22. The single-stranded nucleic acid molecule according to claim 1, wherein the single-stranded nucleic acid molecule comprises at least one modified residue.

23. The single-stranded nucleic acid molecule according to claim 1, further comprising a labeling substance.

24. The single-stranded nucleic acid molecule according to claim 1, further comprising a stable isotope.

25. The single-stranded nucleic acid molecule according to claim 1, which is an RNA molecule.

26. The single-stranded nucleic acid molecule according to claim 1, wherein the total number of bases in the single-stranded nucleic acid molecule is 50 or more.

27. The single-stranded nucleic acid molecule according to claim 1, wherein expression of the gene is inhibited by RNA interference.

28. A composition for inhibiting expression of a target gene, the composition comprising: the single-stranded nucleic acid molecule according to claim 1.

29. A pharmaceutical composition comprising the single-stranded nucleic acid molecule according to claim 1.

30. A method for inhibiting expression of a target gene, the method comprising the step of: using the single-stranded nucleic acid molecule according to claim 1.

31. The method according to claim 30, comprising the step of: administering the single-stranded nucleic acid molecule to a cell, a tissue, or an organ.

32. The method according to claim 31, wherein the single-stranded nucleic acid molecule is administered in vivo or in vitro.

33. The method according to claim 30, wherein expression of the gene is inhibited by RNA interference.

34. A method for inducing RNA interference that inhibits expression of a target gene, the method comprising the step of:
    using the single-stranded nucleic acid molecule according to claim 1.

35. A method of treating an acute lung injury, the method comprising:
    administering the single-stranded nucleic acid molecule according to claim 1 to a patient,
    wherein the single-stranded nucleic acid molecule comprises, as the expression inhibitory sequence, a sequence that inhibits expression of a gene expressed during an acute lung injury.

36. The single-stranded nucleic acid molecule according to claim 1, wherein the linker region (Lx) and/or the linker region (Ly) further comprise 3 to 50 bases.

37. The single-stranded nucleic acid molecule according to claim 1, wherein the expression inhibitory sequence that inhibits expression of a GAPDH gene, TGF-β1 gene, LAMA1 gene, or LMNA gene.

* * * * *

UNITED STATES PATENT AND TRADEMARK OFFICE
CERTIFICATE OF CORRECTION

PATENT NO. : 8,691,782 B2
APPLICATION NO. : 13/254159
DATED : April 8, 2014
INVENTOR(S) : Tadaaki Ohgi et al.

It is certified that error appears in the above-identified patent and that said Letters Patent is hereby corrected as shown below:

On the Title Page
Item (57), Abstract, line 8, "regions (Xc) and (Xc)" should be changed to --regions (X) and (Xc)--.

In the Specification
Column 2, lines 6-7, "regions (Xc) and (Xc)" should be changed to --regions (X) and (Xc)--.
Column 3, line 22, "TNF-αc" should be changed to --TNF-α--; line 56, "regions (Xc) and (Xc)" should be changed to --regions (X) and (Xc)--.
Column 19, line 16, "region (Ye)" should be changed to --region (Yc)--; line 21, "Z-(Xc+Ye)" should be changed to --Z-(Xc+Yc)--; lines 22-23, "Z-(Xc+Ye)" should be changed to --Z-(Xc+Yc)--.
Column 22, line 23, "TGF-β31" should be changed to --TGF-β1--.
Column 24, line 36, "R3Si" should be changed to --$R_3Si$--.
Column 31, line 46, "bought" should be changed to --brought--.
Column 64, line 41, "NI-I-0001" should be changed to --NH-0001--.
Column 81, line 66, "G-actin" should be changed to --β-actin--.
Column 84, lines 55-56, delete "[Sequence Listing] TF11004WO.ST25.txt.".

Signed and Sealed this
Ninth Day of September, 2014

Michelle K. Lee
*Deputy Director of the United States Patent and Trademark Office*